US012653834B1

(12) United States Patent
Flesher et al.

(10) Patent No.: US 12,653,834 B1
(45) Date of Patent: Jun. 16, 2026

(54) METHODS OF SELECTIVELY TREATING COMPLEX REGIONAL PAIN SYNDROME TYPE I (CRPS-I) USING BISPHOSPHONATE DERIVATIVES

(71) Applicant: Ambros Therapeutics, Inc., Irvine, CA (US)

(72) Inventors: Gregory J. Flesher, Irvine, CA (US); Gail Cawkwell, Irvine, CA (US)

(73) Assignee: Ambros Therapeutics, Inc., Irvine, CA (US)

( * ) Notice: Subject to any disclaimer, the term of this patent is extended or adjusted under 35 U.S.C. 154(b) by 0 days.

(21) Appl. No.: 19/272,505

(22) Filed: Jul. 17, 2025

Related U.S. Application Data

(60) Provisional application No. 63/814,250, filed on May 29, 2025.

(51) Int. Cl.
*A61K 31/663* (2006.01)
*A61K 9/00* (2006.01)

(52) U.S. Cl.
CPC .......... *A61K 31/663* (2013.01); *A61K 9/0019* (2013.01)

(58) Field of Classification Search
None
See application file for complete search history.

(56) References Cited

U.S. PATENT DOCUMENTS

| | | | |
|---|---|---|---|
| 5,854,227 | A | 12/1998 | Hartmann et al. |
| 7,704,977 | B2 | 4/2010 | Leonard |
| 9,211,257 | B2 | 12/2015 | Tabuteau et al. |
| 9,216,153 | B2 | 12/2015 | Tabuteau et al. |
| 9,289,384 | B2 | 3/2016 | Tabuteau et al. |
| 9,289,385 | B2 | 3/2016 | Tabuteau et al. |
| 9,655,908 | B2 | 5/2017 | Tabuteau |
| 9,675,626 | B2 | 6/2017 | Tabuteau |
| 9,707,245 | B2 | 7/2017 | Tabuteau |
| 9,770,457 | B2 | 9/2017 | Tabuteau |
| 9,782,421 | B1 | 10/2017 | Tabuteau |
| 9,795,622 | B2 | 10/2017 | Tabuteau |
| 9,820,999 | B2 | 11/2017 | Tabuteau |
| 9,844,559 | B2 | 12/2017 | Tabuteau |
| 9,867,839 | B2 | 1/2018 | Tabuteau |
| 9,884,069 | B2 | 2/2018 | Tabuteau |
| 9,931,352 | B2 | 4/2018 | Tabuteau |
| 9,956,234 | B2 | 5/2018 | Tabuteau |
| 9,999,628 | B2 | 6/2018 | Tabuteau |
| 10,039,773 | B2 | 8/2018 | Tabuteau |
| 10,039,774 | B2 | 8/2018 | Tabuteau |
| 10,052,338 | B2 | 8/2018 | Tabuteau |
| 10,080,765 | B2 | 9/2018 | Tabuteau |
| 10,117,880 | B2 | 11/2018 | Tabuteau |
| 10,350,227 | B2 | 7/2019 | Tabuteau |
| 10,413,561 | B2 | 9/2019 | Tabuteau |
| 10,493,085 | B2 | 12/2019 | Tabuteau |
| 2004/0063670 | A1 | 4/2004 | Fox et al. |
| 2019/0216832 | A1 | 7/2019 | Tabuteau |
| 2019/0328755 | A1 | 10/2019 | Lange et al. |
| 2024/0108641 | A1 | 4/2024 | Tabuteau |

FOREIGN PATENT DOCUMENTS

| | | | |
|---|---|---|---|
| EP | 0494844 | A1 | 7/1992 |
| EP | 0203649 | B1 | 8/1995 |
| EP | 2816354 | B1 | 9/2016 |
| WO | 2011/014781 | A1 | 2/2011 |

OTHER PUBLICATIONS

Varenna et al. (Varenna 2013) "Treatment of complex regional pain syndrome type I with neridronate: a randomized, double-blind, placebo-controlled study," Rheumatology 2013; 52: 534-542 (Year: 2013).*

Varenna et al. (Varenna 2018) "Bisphosphonates in the treatment of complex regional pain syndrome: is bone the main player at early stage of the disease?" Rheumatology International (2018) 38:1959-1962. (Year: 2018).*

Howard et al. "Utility of Radionuclide Bone Scintigraphy in Complex Regional Pain Syndrome," Current Pain and Headache Reports (2018) 22: 7. (Year: 2018).*

Galer et al. "Course of Symptoms and Quality of Life Measurement in Complex Regional Pain Syndrome: A Pilot Survey," Journal of Pain and Symptom Management vol. 20 No. Oct. 4, 2000. (Year: 2000).*

T.J. Coderre, et al., "A Hypothesis for the Cause of Complex Regional Pain Syndrome-Type I (Reflex Sympathetic Dystrophy): Pain Due to Deep-Tissue Microvascular Pathology", Pain Medicine 2010; 11: 1224-1238.

S. P. Cohen, "Rethinking Pharmacological Treatment of CRPS", presentation from the Pain Medicine Meeting 2024, 20 pages.

M.S. Cooper, et al., "Diagnosis and management of hypocalcaemia", BMJ 2008; 336: 1298-1302.

A. Corrado, et al., "Successful treatment of avascular bone necrosis of the knee with neridronate: a case report", Rheumatol Int (2007) 27: 891-893.

B. Cortet, et al., "Treatment of Severe, Recalcitrant Reflex Sympathetic Dystrophy: Assessment of Efficacy and Safety of the Second Generation Bisphosphonate Pamidronate", Clinical rheumatology, 1997, 16, No. 1, 51-56.

L. Cossins, et al., "Treatment of complex regional pain syndrome in adults: A systematic review of randomized controlled trials published from Jun. 2000 to Feb. 2012", Eur J Pain 17 (2013),158-173.

S.C.L.M. Cremers, et al., Pharmacokinetics/Pharmacodynamics of Bisphosphonates—Use of Optimisation of Intermittant Therapy for Osteoporosis, Clin Pharmacokinet 2005; 44 (6): 551-570.

F. Crozier, et al., "Magnetic resonance imaging in reflex sympathetic dystrophy syndrome of the foot", Joint Bone Spine 70 (2003) 503-508.

(Continued)

*Primary Examiner* — Jeffrey S Lundgren
*Assistant Examiner* — Michael J Schmitt
(74) *Attorney, Agent, or Firm* — Venable LLP

(57) ABSTRACT

Methods of selectively treating Complex Regional Pain Syndrome ("CRPS") Type 1 using aminobisphosphonates.

2 Claims, 2 Drawing Sheets

(56) References Cited

OTHER PUBLICATIONS

A.P.C. de Castro, et al., "Zoledronic acid to treat complex regional pain syndrome type I in adult. Case report*", Rev Dor. Sao Paulo, Jan.-Mar. 2011; 12(1): 71-73.
M. de Mos, et al., "Medical history and the onset of complex regional pain syndrome (CRPS)", Pain 139 (2009) 458-466.
M. de Mos, et al., "Outcome of the Complex Regional Pain Syndrome", Clin J Pain 2009; 25: 590-597.
M. de Mos, et al., "The incidence of complex regional pain syndrome: A population-based study", Pain 129 (2007) 12-20.
J.R. deJong, et al., "Pain-Related Fear, Perceived Harmfulness of Activities, and Functional Limitations in Complex Regional Pain Syndrome Type I", The Journal of Pain, vol. 12, No. 12 Dec. 2011, 1209-1218.
P.D. Delmas, et al., "Beneficial Effects of Aminohexane Diphosphonate in Patients with Paget's Disease of Bone Resistant to Sodium Etidronate", The American Journal of Medicine, vol. 83, pp. 276-282 (1987).
J. Demangeat, et al., "Three-Phase Bone Scanning in Reflex Sympathetic Dystrophy of the Hand", J Nucl. Med 29: 26-32 (1988).
D.W. Dempster, et al., "Standardized Nomenclature, Symbols, and Units for Bone Histomorphometry: A 2012 Update of the Report of the ASBMR Histomorphometry Nomenclature Committee", Journal of Bone and Mineral Research, vol. 28, No. 1, pp. 1-16 (2013).
A. Diamanti, et al., "Efficacy and safety of intravenous neridronate in pediatric bone loss associated to Crohn's disease: a case report", Clin Exp Rheumatol. 2009; 27(1): 165.
J. Diepold, et al., "Comparison of Epidemiological Data of Complex Regional Pain Syndrome (CRPS) Patients in Relation to Disease Severity—A Retrospective Single-Center Study", Int. J. Environ. Res. Public Health 2023, 20, 946.
V. Dimova, et al., "Clinical phenotypes and classification algorithm for complex regional pain syndrome", Neurology 2020; 94:e357-e367.
N. Djokanovic, et al., "Does Treatment with Bisphosphonates Endanger the Human Pregnancy?", J Obstet Gynaecol Can 2008; 30(12):1146-1148.
F.A. dos Reis, et al., "Analysis of the Figure-of-Eight method and volumetry reliability for ankle edema measurement", Rev Bras Med Esporte, vol. 10, No. 6, pp. 472-474 (2004).
G.S.E. Dowd, et al., "Complex regional pain syndrome with special emphasis on the knee", J Bone Joint Surg [Br] 2007; 89-B:285-290.
M.T. Drake, et al., "Bisphosphonates: Mechanism of Action and Role in Clinical Practice", Mayo Clin Proc., Sep. 2008, vol. 83(9): 1032-1045.
P.D. Drummond, et al., "Complex regional pain syndrome: intradermal injection of phenylephrine evokes pain and hyperalgesia in a subgroup of patients with upregulated a1-adrenoceptors on dermal nerves", Pain 159 (2018) 2296-2305.
P.D. Drummond, "Sensory Disturbances in Complex Regional Pain Syndrome: Clinical Observations, Autonomic Interactions, and Possible Mechanisms", Pain Medicine 2010; 11: 1257-1266.
R.S. D'Souza, et al., "Global Burden of Complex Regional Pain Syndrome in At-Risk Populations: Estimates of Prevalence From 35 Countries Between 1993 and 2023", Anesth Analg 2025; XXX:00-00.
R.H. Dworkin, et al., "Interpreting the Clinical Importance of Treatment Outcomes in Chronic Pain Clinical Trials: IMMPACT Recommendations", The Journal of Pain, vol. 9, No. 2, 105-121 (2008).
R.H. Dworkin, et al., "Core outcome measures for chronic pain clinical trials: IMMPACT recommendations", Pain 113 (2005) 9-19.
R.H. Dworkin, et al., "Interpreting the clinical importance of group differences in chronic pain clinical trials: IMMPACT recommendations", Pain 146 (2009) 238-244.
B.J. Edwards, et al., "Acute Kidney Injury and Bisphosphonate Use in Cancer: A Report From the Research on Adverse Drug Events and Reports (RADAR) Project", Journal of Oncology Practice, vol. 9, iss. 2, pp. 101-107 (2013).
J.T. Farrar, et al., "Clinical importance of changes in chronic pain intensity measured on an 11-point numerical pain rating scale", Pain 94 (2001) 149-158.
A. Fassio, et al., "Pharmacological treatment in adult patients with CRPS-I: a systematic review and meta-analysis of randomized controlled trials", Rheumatology 2022, vol. 61, 3534-3546.
D.K. Fast, et al., "The Effects of Diphosphonates on the Growth and Glycolysis of Connective-Tissue Cells in Culture", Biochem. J. (1978) vol. 172, 97-107.
S. Ferlito, et al., "Treatment of bisphosphonate-related osteonecrosis of the jaws: presentation of a protocol and an observational longitudinal study of an Italian series of cases", British Journal of Oral and Maxillofacial Surgery 50 (2012) 425-429.
M.C. Ferraro, et al., "Interventions for treating pain and disability in adults with complex regional pain syndrome—an overview of systematic reviews (Review)", Cochrane Database of Systematic Reviews 2023, Issue 6. Art. No. CD009416.
H. Fleisch, "Bisphosphonates: Mechanisms of Action", Endocrine Reviews 19(1): 80-100 (1998).
H. Fleisch, "Bisphosphonates in osteoporosis", Eur Spine J (2003) 12 (Suppl. 2): S142-S146.
T. Forouzanfar, et al., "What Is a Meaningful Pain Reduction in Patients With Complex Regional Pain Syndrome Type 1?", The Clinical Journal of Pain 19: 281-285 (2003).
C. Gaggiano, et al., "Neridronate for transient osteoporosis of the hip in a child", Osteoporosis International (2022) 33: 1619-1624.
M. Gallizzi, et al., "Medication Quantificatoin Scale Version III: Internal Validation of Detrimenet Weights Using a Chronic Pain Population", Pain Practice, vol. 8, iss. 1, 1-4 (2008).
L. Gamalero, et al., "Efficacy and safety of neridronate in paediatric type I complex regional pain syndrome: a multicentre experience", Clinical and Experimental Rheumatology 2025; 43: 533-537.
D. Gatti, et al., "Management of patients with complex regional pain syndrome type I", Osteoporos Int (2016).
D. Gatti, et al., "Intravenous Neridronate in Children With Osteogenesis Imperfecta: A Randomized Controlled Study", J Bone Miner Res (2005); 20:758-763.
D. Gatti, et al., "Neridronic acid for the treatment of bone metabolic diseases", Expert Opin. Drug Metab. Toxicol. (2009) 5(10): 1305-1311.
D. Gatti, et al., "Intravenous Bisphosphonate Therapy Increases Radial Width in Adults with Osteogenesis Imperfecta", J Bone Miner Res 2005; 20:1323-1326.
L. Gedmintas, et al., "Bisphosphonates and Risk of Subtrochanteric, Femoral Shaft, and Atypical Femur Fracture: A Systematic Review and Meta-Analysis", J Bone Miner Res (2013) 28:1729-1737.
J.H.B. Geertzen, et al., "Relationship between impairments, disability and handicap in re flex sympathetic dystrophy patients: a long-term follow-up study", Clinical Rehabilitation 1998; 12: 402-412.
C. Gharibo, et al., "Diagnostic Guidance for Chronic Complex Regional Pain Syndrome Type I and Type II from the American Society of Interventional Physicians (ASIPP)", Pain Physician 2025; 28:E287-E327.
A. Giusti, et al., "Treatment of complex regional pain syndrome type I with bisphosphonates", RMD Open 2015, 1:e000056.
A. Giusti, et al., "Atypical fractures and bisphosphonate therapy: A cohort study of patients with femoral fracture with radiographic adjudication of fracture site and features", Bone 48 (2011) 966-971.
F.H. Glorieux, et al., "Cyclic Administration of Pamidronate in Children With Severe Osteogenesis Imperfecta", The New England Journal of Medicine, vol. 339, No. 14, 947-952.
A. Goebel, "Complex regional pain syndrome in adults", Rheumatology 2011; 50: 1739-1750.
A. Goebel, et al., "Standards for the diagnosis and management of complex regional pain syndrome: Results of a European Pain Federation task force", Eur J Pain. 2019; 23: 641-651.
A. Goebel, et al., "Complex regional pain syndrome, prototype of a novel kind of autoimmune disease", Autoimmunity Reviews 12 (2013) 682-686.
A. Goebel, et al., "The Valencia consensus-based adaptation of the IASP complex regional pain syndrome diagnostic criteria", Pain 162 (2021) 2346-2348.

(56) References Cited

OTHER PUBLICATIONS

L. Gong, et al., "Bisphosphonates pathway", Pharmacogenetics and Genomics 2011, 21: 50-53.
G. Gradl, et al., "Sympathetic dysfunction as a temporary phenomenon in acute posttraumatic CRPS I", Clin Auton Res (2005) 15: 29-34.
J.S. Grider, "CRPS—Autonomic, Sensory and Motor Function", presentation from the Pain Medicine Meeting 2024, 13 pages.
S. Grieve, et al., "Recommendations for a first Core Outcome Measurement set for complex regional PAin syndrome Clinical sTudies (COMPACT)", Pain 2017 158(6): 1083-1090.
S. Grieve, et al., "An international study to explore the feasibility of collecting standardised outcome data for Complex Regional Pain Syndrome: recommendations for an international clinical research registry", British Journal of Pain 2023, vol. 17(5): 468-478.
T. Guo, et al., "Substance P signaling contributes to the vascular and nociceptive abnormalities observed in a tibial fracture rat model of complex regional pain syndrome type I", Pain 108 (2004) 95-107.
W. Guy, ECDEU Assessment Manual for Psychopharmacology, revised 1976, U.S. Department of Health, Education and Welfare.
F.H. Hant, et al., "Drugs that may harm bone: Mitigating the risk", Cleveland Clinic Journal of Medicine, vol. 83, No. 4, 281-288 (2016).
R.N. Harden, et al., "Proposed New Diagnostic Criteria for Complex Regional Pain Syndrome", Pain Medicine (2007), vol. 8, No. 4, 326-331.
R.N. Harden, et al., "Development of a severity score for CRPS", Pain 151 (2010) 870-876.
R.N. Harden, et al., "Complex Regional Pain Syndrome: Practical Diagnostic and Treatment Guidelines, 5th Edition", Pain Medicine 23(S1), 2022, S1-S53.
R.N. Harden, et al., "Complex Regional Pain Syndrome: Practical Diagnostic and Treatment Guidelines, 4th Edition", Pain Medicine 2013; 14: 180-229.
R.N. Harden, et al., "A prospective, multisite, international validation of the Complex Regional Pain Syndrome Severity Score", Pain 158 (2017) 1430-1436.
R.N. Harden, et al., "Validation of proposed diagnostic criteria (the "Budapest Criteria") for Complex Regional Pain Syndrome", Pain Aug. 2010; 150(2): 268-274.
R.N. Harden, et al., "Complex regional pain syndrome: are the IASP diagnostic criteria valid and sufficiently comprehensive?", Pain 83 (1999) 211-219.
R.N. Harden, et al., "Medication Quantification Scale Version III: Update in Medication Classes and Revised Detriment Weights by Survey of American Pain Society Physicians", The Journal of Pain, vol. 6, No. 6, pp. 364-371 (2005).
M.A. Harnick, et al., "Bone metabolism in complex regional pain syndrome", Pain Reports 9 (2024) e1217.
M.A. Harnik, et al., "Complex Regional Pain Syndrome (CRPS) and the Value of Early Detection", Current Pain and Headache Reports (2023) 27: 417-427.
B. Hartmannsberger, et al., "Transient immune activation without loss of intraepidermal innervation and associated Schwann cells in patients with complex regional pain syndrome", Journal of Neuroinflammation (2024) 21:23.
C.M. Hedrich, et al., "A clinical and pathomechanistic profile of chronic nonbacterial osteomyelitis/chronic recurrent multifocal osteomyelitis and challenges facing the field", Expert Review of Clinical Immunology, 9:9, 845-854.
A.O. Hoff, et al., "Frequency and Risk Factors Associate with Osteonecrosis of the Jaw in Cancer Patients Treated with Intravenous Bisphosphonates", J Bone Miner Res 2008; 23: 826-836.
T. Hospach, et al., "Spinal involvement in chronic recurrent multifocal osteomyelitis (CRMO) in childhood and effect of pamidronate", Eur J Pediatr (2010) 169: 1105-1111.
B.A. Howard, et al., " Utility of Radionuclide Bone Scintigraphy in Complex Regional Pain Syndrome", Current Pain and Headache Reports (2018) 22:7.
V. Huge, et al., "Interaction of Hyperalgesia and Sensory Loss in Complex Regional Pain Syndrome Type I (CRPS I)", PLoS One 3(7): e2742 (2008).
C. Hunt, "Pathophysiology of CRPS: Defining Treatment Targets", presentation from the Pain Medicine Meeting 2024, 13 pages.
L. Idolazzi, et al., "Treatment with neridronate in children and adolescents with osteogenesis imperfecta: Data from open-label, not controlled, three-year Italian study", Bone 103 (2017) 144-149.
G. Iolascon, et al., "The Rationale for Using Neridronate in Musculoskeletal Disorders: From Metabolic Bone Diseases to Musculoskeletal Pain", Int. J. Mol. Sci. 2022, 23, 6921.
W. Janig, et al., "Complex regional pain syndrome: mystery explained? ", Lancet Neurol 2003; 2: 687-697.
W.S.S. Jee, et al., "Overview: animal models of osteopenia and osteoporosis", J Musculoskel Neuron Interact 2001; 1(3): 193-207.
S. Johnson, et al. "Complex regional pain syndrome what is the outcome?—a systematic review of the course and impact of CRPS at 12 months from symptom onset and beyond", Eur J Pain 2022; 26: 1203-1220.
C.M. Jones, et al., "Use of Medication for Opioid Use Disorder Among Adults With Past-Year Opioid Use Disorder in the US, 2021", JAMA Network Open 2023; 6(8): e2327488.
L. Kapural, et al., Create-1 study: a randomized, double-blind, placebo-controlled study to assess the efficacy and safety of AXS-02 (disodium zoledronate tetrahydrate) administered orally to subjects with Complex Regional Pain Syndrome Type I (CRPS-1), The Journal of Pain Abstracts, S81-S82 (2016).
H. Kaur, et al., "Complex Regional Pain Syndrome Diagnosed with Triple-Phase Bone Scanning", J Nucl Med Technol 2017; 45:243-244.
A. Kawabata, et al., "Antiallodynic effect of etidronate, a bisphosphonate, in rats with adjuvant-induced arthritis: Involvement of ATP-sensitive Kplus channels", Neuropharmacology 51 (2006) 182-190.
S. Keller, et al., "Validity of the Brief Pain Inventory for Use in Documenting the Outcomes of Patients with Noncancer Pain", Clin J Pain 2004; 20: 309-318.
K.A. Kennel, et al., "Adverse Effects of Bisphosphonates: Implications for Osteoporosis Management", Mayo Clin Proc. 2009: 84(7): 632-638.
C. Kerrison, et al., "Pamidronate in the treatment of childhood SAPHO syndrome", Rheumatology 2004; 43: 1246-1251.
S.A. Khan, et al., "Elimination and Biochemical Responses to Intravenous Alendronate in Postmenopausal Osteoporosis", J Bone Miner Res 1997; 12: 1700-1707.
S. Khosla, et al., "Benefits and Risks of Bisphosphonate Therapy for Osteoporosis", J Clin Endocrinol Metab, 97:2272-2282 (2012).
J. Kim, et al., "Clinical implication of regional osteopenia in complex regional pain syndrome: a retrospective comparative study", Reg Anesth Pain Med 2025; 0:1-7.
Y. Kim, et al., "Diagnosis of complex regional pain syndrome", Ann Clin Neurophysiol 2022; 24(2): 35-45.
W.S. Kingery, et al., "A substance P receptor (NK1) antagonist can reverse vascular and nociceptive abnormalities in a rat model of complex regional pain syndrome type II", Pain 104 (2003) 75-84.
L. Knudsen, et al., "Subtypes of complex regional pain syndrome—a systematic review of the literature", Pain Reports 8 (2023) e1111.
G. Kollman, et al., "The role of the bone in complex regional pain syndrome 1—A systematic review", Eur J Pain 2023; 27:794-804.
H.H. Kramer, et al., "TNF-alpha in CRPS and 'normal' trauma—Significant differences between tissue and serum", Pain 152 (2011) 285-290.
H.H. Kramer, et al., "Osteoprotegerin: A new biomarker for impaired bone metabolism in complex regional pain syndrome?", Pain 155 (2014) 889-895.
I. Kubalek, et al., "Treatment of reflex sympathetic dystrophy with pamidronate: 29 cases", Rheumatology 2001; 40:1394-1397.
A. Kuttikat, et al., "Neurocognitive and Neuroplastic Mechanisms of Novel Clinical Signs in CRPS", Front. Hum. Neurosci. 10:16 (2016).

(56) References Cited

OTHER PUBLICATIONS

H.W. Kwon, et al.,"Diagnostic Performance of Three-Phase Bone Scan for Complex Regional Pain Syndrome Type 1 with Optimally Modified Image Criteria", Nucl Med Mol Imaging (2011) 45:261-267.
G. La Montagna, et al., "Successful neridronate therapy in transient osteoporosis of the hip", Clin Rheumatol (2005) 24: 67-69.
L.L. Laslett, et al., "Zoledronic acid reduces knee pain and bone marrow lesions over 1 year: a randomised controlled trial", Ann Rheum Dis 2012; 71: 1322-1328.
M.A. Lawson, et al., "Differences Between Bisphosphonates in Binding Affinities for Hydroxyapatite", J Biomed Mater Res Part B: Appl Biomater 92B: 149-155 (2010).
J.S. Leard, et al., "Reliability and Concurrent Validity of the Figure-of-Eight Method of Measuring Hand Size in Patients with Hand Pathology", J Orthop Sports Phys Ther 2004; 34:335-340.
J. Lee, et al., "Early aggressive treatment improves prognosis in complex regional pain syndrome", Practioner 2011; 255(1736): 23-26, abstract.
M. Lenz, et al., "Local cytokine changes in complex regional pain syndrome type I (CRPS I) resolve after 6 months", Pain 154 (2013) 2142-2149.
T.W. Leonard, et al., "Studies of Bioavailability and Food Effects of MER-101 Zoledronic Acid Tablets in Postmenopausal Women", poster 317, ASCO Breast Cancer Symposium, San Francisco, CA, Oct. 2009.
Y. Liu, et al., "Animal Models of Complex Regional Pain Syndrome Type I", Journal of Pain Research 2021; 14: 3711-3721.
K.W. Lyles, et al., "Zoledronic Acid in Reducing Clinical Fracture and Mortality after Hip Fracture", N Engl J Med. 2007; 357.
S.E. Mackinnon, et al., "The use of three-phase radionuclide bone scanning in the diagnosis of reflex sympathetic dystrophy", J Hand Surg 9A: 556-563 (1984).
J.F. Maillefert, et al., "Treatment of refractory reflex sympathetic dystrophy with pamidronate", Ann Rheum Dis 1995 54:687.
E. Maines, et al., "Children and adolescents treated with neridronate for osteogenesis imperfecta show no evidence of any osteonecrosis of the jaw", J Bone Miner Metab (2012) 30:434-438.
T. Mainka, et al., "Comparison of muscle and joint pressure-pain thresholds in patients with complex regional pain syndrome and upper limb pain of other origin", Pain 155 (2014) 591-597.
W.P. Maksymowych, "Bisphosphonates—Anti-Inflammatory Properties", Curr. Med. Chem.—Anti-Inflammatory & Anti-Allergy Agents, 2002, 1, 15-28.
M. Manfredi, et al., "Bishphosphonate-related osteonecrosis of the jaws: a case series of 25 patients affected by osteoporosis", Int. J. Oral Maxillofac. Surf. 2011; 40:277-284.
T.J.P. Mangnus, et al., "From a Symptom-Based to a Mechanism-Based Pharmacotherapeutic Treatment in Complex Regional Pain Syndrome", Drugs (2022) 82:511-531.
T.J.P. Mangnus, et al., "Is there an association between serum soluble interleukin-2 receptor levels and syndrome severity in persistent Complex Regional Pain Syndrome?", Pain Medicine, 2023, 24, 1234-1243.
D. Manicourt, et al., "Role of Alendronate in Therapy for Post-traumatic Complex Regional Pain Syndrome Type I of the Lower Extremity", Arthritis & Rheumatism, vol. 50, No. 11, Nov. 2004, pp. 3690-3697.
D.C. Manning, et al., "Lenalidomide for Complex Regional Pain Syndrome Type 1: Lack of Efficacy in a Phase II Randomized Study", The Journal of Pain, vol. 15, No. 12 Dec. 2014, pp. 1366-1376.
C. Martin, "Bisphosphonates as Treatment for Complex Regional Pain Syndrome (CRPS)", WorkSafeBC Evidence-Based Practice Group, Nov. 2017, 28 pages.
R. Mattie, et al., "Spinal cord stimulation for the treatment of complex regional pain syndrome: A systematic review of randomized controlled trials", Interventional Pain Medicine 3 (2024) 100527.
M. Mazzantini, et al., "Single infusion of neridronate (6-amino-1-hydroxy-hexylidene-1,1-bisphosphonate) in patients with active rheumatoid arthritis: Effects on disease activity and bone resorption markers", Aging 14: 197-201 (2002).
G.K. Mbizvo, et al., "Placebo Responses in Long-Standing Complex Regional Pain Syndrome: A Systematic Review and Meta-Analysis", The Journal of Pain, vol. 16, No. 2 Feb. 2015: 99-115.
E.V. McCloskey, et al., "Comparative Effects of Intravenous Disphosphonates on Calcium and Skeletal Metabolism in Man", Bone, 8, Supp. 1, S35-S41 (1987).
L.M. McCracken, et al., "A short version of the Pain Anxiety Symptoms Scale (PASS-20): Preliminary development and validity", Pain Res Manage 2002; 7(1):45-50.
K. Mehling, et al., "Bilateral deficiency of Meissner corpuscles and papillary microvessels in patients with acute complex regional pain syndrome", Pain 165 (2024) 1613-1624.
R.P. Merkow, et al., "Reporting Guidelines: The Consolidated Standards of Reporting Trials (CONSORT) Framework", JAMA Surg. Sep. 1, 2021, 156(9): 877-878.
H. Merskey, et al., Classification of Chronic Pain, 2d edition, IASP Press, Seattle (1994).
P.D. Miller, et al., "Renal Safety in Patients Treated with Bisphosphonates for Osteoporosis: A Review", J Bone Miner Res, vol. 28, No. 10, pp. 2049-2059 (2013).
D.H. Minsker, et al., "Effects of the Bisphosphonate, Alendronate, on Parturition in the Rat", Toxicol. Appl. Pharmacol. 121, 217-233 (1993).
E.S. Molloy, et al., "Microsomal prostaglandin E2 synthase 1 expression in basic calcium phosphate crystal-stimulated fibroblasts: role of prostaglandin E2 and the EP4 receptor", Osteoarthritis and Cartilage (2009) 17, 686-692.
J.Y. Moon, et al., "Analysis of patterns of three-phase bone scintigraphy for patients with complex regional pain syndrome diagnosed using the proposed research criteria (the 'Budapest Criteria')", British Journal of Anaesthesia 108(4): 655-661 (2012).
H. Morbach, et al., "Autoinflammatory bone disorders", Clinical Immunology (2013) 147: 185-196.
A. Moretti, et al., "Effectiveness of Neridronate in the Management of Bone Loss in Patients with Duchenne Muscular Dystrophy: Results from a Pilot Study", Adv Ther (2022).
A. Moretti, et al., Complex Regional Pain Syndrome Type I Following Non-Orthopedic Surgery: Case Report and Narrative Review, Diagnostics 2021, 11, 1596.
R.J. Munnikes, et al., "Intermediate Stage Complex Regional Pain Syndrome Type 1 Is Unrelated to Proinflammatory Cytokines", Mediators of Inflammation 2005; 6: 366-372.
M. Muratore, et al., "Uso Del Neridronato Nel Trattamento Dell'Algodistrofia Simpatica Riflessa", Reumatismo 2002, PB-16, vol. 54, No. 3, (suppln. N. 2), 2 pages.
M. Muratore, et al., "Il neridronato nel trattamento dell'algodistrofia simpatice riflessa dell'anca: confront in aperto con il clodronato", Progressi in Reumatologia, vol. 5, suppl. 1, p. 89 (2004).
H. Mussawy, et al., "Evaluation of bone microstructure in CRPS-affected upper limbs by HR-pQCT", Clinical Cases in Mineral and Bone Metabolism 2017; 14(1): 54-59.
A.L. Naleway, et al., "Epidemiology of Upper Limb Complex Regional Pain Syndrome in a Retrospective Cohort of Persons Aged 9-30 Years, 2002-2017", Perm J 2023; 27: 22.170.
G.H. Nancollas, et al., "Novel insights into actions of bisphosphonates on bone: Differences in interactions with hydroxyapatite", Bone 38 (2006) 617-627.
M. Neves, et al., "Synthesis, characterization and biodistribution of bisphosphonates Sm-153 complexes: correlation with molecular modeling interaction studies", Nuclear Medicine and Biology 29 (2002) 329-338.
M.K. Nicholas, "The pain self-efficacy questionnaire: Taking pain into account", European Journal of Pain 11 (2007) 153-163.
J. Nijs, et al., "Treatment of central sensitization in patients with 'unexplained' chronic pain: what options do we have?", Expert Opinion on Pharmacotherapy 12:7, 1087-1098 (2011).
A.L. Oaklander, et al., "The complex regional pain syndrome", Handbook of Clinical Neurology, vol. 131, chapter 27, pp. 481-503 (2015).

(56) References Cited

OTHER PUBLICATIONS

N.E. O'Connell, et al., "Interventions for treating pain and disability in adults with complex regional pain syndrome (Protocol)", Cochrane Database of Systematic Reviews 2011, Issue 11, Art. No. CD009416.
S. Walker, et al., "Implications of a Local Overproduction of Tumor Necrosis Factor-a in Complex Regional Pain Syndrome", Pain Medicine 2011; 12: 1784-1807.
L. Wang, et al., "Bisphosphonates inhibit pain, bone loss, and inflammation in a rat tibia fracture model of complex regional pain syndrome", Anesth Analg. Oct. 2016; 123(4): 1033-1045.
A. Wardley, et al., "Zoledronic acid significantly improves pain scores and quality of life inbreast cancer patients with bone metastases: a randomised, crossover study of community vs hospital bisphosphonate administration", British Journal of Cancer (2005) 92, 1869-1876.
J.E. Ware, et al., "SF-36 Health Survey Update", Spine vol. 25, No. 24, pp. 3130-3139 (2000).
H. Waring, et al., "A malevolent force: A qualitative exploration of perceptions of changes in bodily function and sensations in complex regional pain syndrome", Journal of Pain 29 (2025) 105354.
G. Wasner, et al., "Vascular Abnormalities in Acute Reflux Sympathetic Dystrophy (CRPS I)", Arch Neurol. 1999; 56: 613-620.
G. Wasner, et al., "Vascular Abnormalities in Acute Reflux Sympathetic Dystrophy (CRPS I): Mechanisms and Diagnostic Value", Brain (2001); 124: 587-599.
T. Wei, et al., "Acute versus chronic phase mechanisms in a rat model of CRPS", Journal of Neuroinflammation (2016).
B. Wen, et al., "The Role of Neuroinflammation in Complex Regional Pain Syndrome: A Comprehensive Review", Journal of Pain Research 2023; 16: 3061-3073.
R. Werner, et al., "Factors affecting the sensitivity and specificity of the three-phase technetium bone scan in the diagnosis of reflex sympathetic dystrophy syndrome in the upper extremity", J Hand Surg 1989; 14A: 520-523.
M.M. Wertli, et al., "Rational Pain Management in ComplexRegional Pain Syndrome 1 (CRPS 1)—A Network Meta-Analysis", Pain Medicine 2014; 15: 1575-1589.
M.M. Wertli, et al., "Usefulness of bone scintigraphy for the diagnosis of Complex Regional Pain Syndrome 1: A systematic review and Bayesian meta-analysis", PLoS One 12(3): e0173688 (2017).
G. Wheater, et al., "The clinical utility of bone marker measurements in osteoporosis", Journal of Translational Medicine 2013, 11:201.
S. Woo, et al., "Systematic Review: Bisphosphonates and Osteonecrosis of the Jaws", Ann Intern Med. 2006; 144: 753-761.
C.J. Woolf, "What is this thing called pain?", J Clin Invest. 2010; 120(11): 3742-3744.
T.J. Wronski, et al., "Temporal Relationship between Bone Loss and Increased Bone Turnover in Ovariectomized Rats", Calcif Tissue Int (1988) 43:179-183.
N. Wuppenhorst, et al., "Sensitivity and Specificity of 3-phase Bone Scintigraphy in the Diagnosis of Complex Regional Pain Syndrome of the Upper Extremity", Clin J Pain 2010; 26: 182-189.
J. Yanow, et al., "Complex Regional Pain Syndrome (CRPS/RSD) and Neuropathic Pain: Role of Intravenous Bisphosphonates as Analgesics", The Scientific World Journal (2008) 8, 229-236.
Y. Yao, et al., "Alendronate Attenuates Spinal Microglial Activation and Neuropathic Pain", The Journal of Pain, vol. 17, No. 8 Aug. 2016: pp. 889-903.
H.E. Young, et al., "Pamidronate effect compared with a steroid on complex regional pain syndrome type I: Pilot randomised trial", The Netherlands Journal of Medicine, Jan. 2016, vol. 74, No. 1, pp. 30-35.
A. Zalewski, et al., "Clinical and Molecular Barriers to Understanding the Pathogenesis, Diagnosis, and Treatment of Complex Regional Pain Syndrome (CRPS)", Int. J. Mol. Sci. 2025; 26:2514.
A. Zangrandi, et al., "Complex Regional Pain Syndrome. A Comprehensive Review on Neuroplastic Changes Supporting the Use of Non-invasive Neurostimulation in Clinical Settings", Front. Pain Res. 2:732343.
J. Zaspel, et al., "Treating CRPS I in the early stage—cortisone (methyl prednisolone) versus bisphosphonate (zoledronic acid)", German Congress for Orthopedics and Trauma Surgery, 71st Annual Conference of the German Association for Trauma Surgery, 93rd Annual Conference of the German Association for Orthopedics and Orthopedic Surgery, and the 48th Annual Conference of the Professional Association of Specialists in Orthopedics and Trauma Surgery, meeting abstract (2007).
G. Zou, et al., "A Modified Poisson Regression Approach to Prospective Studies with Binary Data", Am J Epidemiol 2004; 159(7): 702-706.
A. Zyluk, et al., "Functional impairment of the extremities in patients who got over Complex Regional Pain Syndrome", Folia Medica Cracoviensia, vol. LXIV, No. 3, 119-127 (2024).
Fosamax® Drug Label, Merck Sharp & Dohme Corp. (Dec. 2013).
Zometa® Drug Label, Novartis Pharma. Corp. (Apr. 2014).
R.J. Schwartzman, et al., "The Natural History of Complex Regional Pain Syndrome", Clin J Pain 2009; 25: 273-280.
A. Schwarzer, et al., "Complex Regional Pain Syndrome", Guide to Pain Management in Low-Resource Settings, IASP, Seattle, chapter 33, pp. 249-254 (2010).
O. Semler, et al., "Reshaping of Vertebrae during Treatment with Neridronate or Pamidronate in Children with Osteogenesis Imperfecta", Horm Res Paediatr 2011; 76:321-327.
E. Shane, et al., "Atypical Subtrochanteric and Diaphyseal Femoral Fractures: Second Report of a Task Force of the American Society for Bone and Mineral Research", J Bone Miner Res, vol. 29, No. 1, pp. 1-23 (2014).
D. Sharma, et al., "Bisphosphonate-related osteonecrosis of jaw (BRONJ): diagnostic criteria and possible pathogenic mechanisms of an unexpected anti-angiogenic side effect", Vascular Cell 2013, 5:1.
S. Shermon, et al., "Prescription Trends in Complex Regional Pain Syndrome: A Retrospective Case-Control Study", Brain Sci. 2023, 13, 1012.
N. Sieweke, et al., "Patterns of hyperalgesia in complex regional pain syndrome", Pain 80 (1999) 171-177.
S.L. Silverman, et al., "Effect of acetaminophen and fluvastatin on post-dose symptoms following infusion of zoledronic acid", Osteoporos Int (2011) 22: 2337-2345.
K. Siminoski, et al., "Intravenous Pamidronate for Treatment of Reflex Sympathetic Dystrophy During Breast Feeding", J Bone Miner Res 2000; 15: 2052-2055.
P.J. Simm, et al., "Bisphosphonate Treatment in Chronic Recurrent Multifocal Osteomyelitis", J Pediatr 2008: 152: 571-575.
S.H. Sindrup, et al., "Venlafaxine versus imipramine in painful polyneuropathy—A randomized, controlled study", Neurology 2003; 60:1284-1289.
K.M. Smart, et al., "Physiotherapy for pain and disability in adults with complex regional pain syndrome (CRPS) types I and II", Cochrane Database of Systematic Reviews 2022, Issue 5, Art. No. CD010853.
M.G. Sobeeh, et al.,"Impact of different CRPS phenotypes and diagnostic criteria on quantitative sensory testing outcomes: systematic review and meta-analysis", Pain Medicine 2024; 25: 211-225.
M. Sorel, et al., "Three-phase Bone Scintigraphy Can Predict the Analgesic Efficacy of Ketamine Therapy in CRPS", Clin J Pain 2018; 34: 831-837.
M. Stanton-Hicks, et al., "Reflex sympathetic dystrophy: changing concepts and taxonomy", Pain 63 (1995) 127-133.
I.P. Stathopoulos, et al., "The use of bisphosphonates in women prior to or during pregnancy and lactation", Hormones 2011, 10(4): 280-291.
A.A. Stone, et al., "Intensive momentary reporting of pain with an electronic diary: reactivity, compliance, and patient satisfaction", Pain 104 (2003) 343-351.

(56) References Cited

OTHER PUBLICATIONS

A.A. Stone, et al., "Understanding recall of weekly pain from a momentary assessment perspective: absolute agreement, between- and within-person consistency, and judged change in weekly pain", Pain 107 (2004) 61-69.
P. Sudeck, et al., "On Acute (Trophoneurotic) Bone Atrophy Following Inflammations and Injuries of the Extremities", Deutsche Medicinische Wochenschrift, No. 19, pp. 336-338 (1902).
M.J.L. Sullivan, et al., "The Pain Catastrophizing Scale: Development and Validation", Psychological Assessment 1995, vol. 7, No. 4, pp. 524-532.
S. Taylor, et al., "Complex Regional Pain Syndrome: A Comprehensive Review", Pain Ther (2021) 10: 875-892.
D. Thiebaud, et al., "An In Vitro and In Vivo Study of Cytokines in the Acute-Phase Response Associated with Bisphosphonates", Calcif Tissue Int (1997) 61:386-392.
N.D. Toussaint, et al., "Bisphosphonates in Chronic Kidney Disease; Balancing Potential Benefits and Adverse Effects on Bone and Soft Tissue", Clin J Am Soc Nephrol 4: 221-233 (2009).
D.Q.H. Tran, et at., "Treatment of complex regional pain syndrome: a review of the evidence", Can J Anesth (2010); 57: 149-166.
J. Turner, et al., "Emergency management of acute hypocalcaemia in adult patients", Endocrine Connections (2019) 8, X1.
L. Turner-Stokes, et al., "Complex regional pain syndrome in adults: concise guidance", Clinical Medicine 2011, vol. 11, No. 6, pp. 596-600.
T.M. Tzschentke, "Pharmacology of bisphosphonates in pain", Br J Pharmacol. 2021; 178: 1973-1994.
N. Uceyler, et al., "Differential expression patterns of cytokines in complex regional pain syndrome", Pain 132 (2007) 195-205.
K. Vahtsevanos, et al., "Longitudinal Cohort Study of Risk Factors in Cancer Patients of Bisphosphonate-Related Osteonecrosis of the Jaw", J Clin Oncol 27: 5356-5362 (2009).
M.P.V. Valdes, et al., "Identification of two biological subgroups of complex regional pain syndrome type 1 by transcriptomic profiling of skin and blood in women", Molecular Medicine (2025) 31(94).
M. Vaneker, et al., "Impairments as measured by ISS do not greatly change between one and eight years after CRPS 1 diagnosis", European Journal of Pain 10 (2006) 639-644.
G.A.J. vanVelzen, et al., "Sex matters in complex regional pain syndrome", Eur J Pain. 2019; 23: 1108-1116.
M. Varenna, et al., Intravenous Clodronate in the Treatment of Reflex Sympathetic Dystrophy Syndrome. A Randomized, Double Blind, Placebo Controlled Study. J Rheumatol Jun. 2000;27(6):1477-1483, abstract.
M. Varenna, et al. "Neridronato Endovenoso Nel Trattamento Della Sindrome Algodistrofica", Reumatismo, vol. 56, No. 3 (No. sp. 3), P60, 2004, 3 pages.
M. Varenna, et al., "Treatment of complex regional pain syndrome type I with neridronate: a randomized, double-blind, placebo-controlled study", Rheumatology 2013, vol. 52, pp. 534-542.
M. Varenna, et al., "Bisphosphonates in Complex Regional Pain syndrome type I: how do they work?", Clin Exp Rheumatol 2014; 32: 451-454.
M. Varenna, "The Clinical Framework of Algodystrophy (Complex Regional Pain Syndrome Type I). An Update", GIOT, 2011; 37:227-234.
M. Varenna, et al., "Is CRPS-1 a Chronic Disabling Disease? A Long-term, Real-Life Study on Patients Treated with Neridronate", Clinical Medicine Insights: Arthritis and Musculoskeletal Disorders, vol. 17, pp. 1-8 (2024).
M. Varenna, "Bisphosphonates beyond their anti-osteoclastic properties", Rheumatology 2014; 53: 965-967.
M. Varenna, et al., "Predictors of Responsiveness to Bisphosphonate Treatment in Patients with Complex Regional Pain Syndrome Type I: A Retrospective Chart Analysis", Pain Medicine 2017; 18: 1131-1138.
M. Varenna, et al., "Intramuscular neridronate for the treatment of complex regional pain syndrome type 1: a randomized, double-blind, placebo-controlled study", Ther Adv Musculoskel Dis 2021, vol. 13, pp. 1-12.
M. Varenna, et al., "Long-term efficacy and safety of neridronate treatment in patients with complex regional pain syndrome type 1: a pre-specified, open-label, extension study", Ther Adv Musculoskelet Dis 2022, vol. 14: 1-12.
M. Varenna, et al., "Osteoclast in CRPS: an alleged guilty fully acquitted", Osteoporosis International 2025.
M. Varenna, et al., "Bone Turnover Markers and Wnt Signaling Modulators in Early Complex Regional Pain Syndrome. A Pre-specified Observational Study", Calcified Tissue International (2024) 115: 251-259.
M. Varenna, et al., "Targeting the bone in the treatment of complex regional pain syndrome: In depth—The truth?", Journal of Orthopaedics Trauma Surgery and Related Research, 3 pages (2018).
S.D. Vasikaran, "Bisphosphonates: an overview with special reference to alendronate", Ann Clin Biochem 2001; 38: 608-623.
P.H.J.M. Veldman, et al., "Signs and symptoms of reflex sympathetic dystrophy: prospective study of 829 patients", Lancet 1993; 342:1012-1016.
M.K. Vernon, et al., "Reliability, Validity, and Responsiveness of the Daily Sleep Interference Scale Among Diabetic Peripheral Neuropathy and Postherpetic Neuralgia Patients", J Pain Symptom Manage 2008; 36: 54-68.
O. Viapiana, et al., "Bisphosphonates vs infliximab in ankylosing spondylitis treatment", Rheumatology 2014; 53:90-94.
K. Walker, et al., "Disease modifying and anti-nociceptive effects of the bisphosphonate zoledronic acid in a model of bone cancer pain", Pain 100 (2002) 219-229.
J.P. O'Donoghue, et al., "Three-Phase Bone Scintigraphy—Asymmetric Patterns in the Upper Extremities of Asymptomatic Normals and Reflex Sympathetic Dystrophy Patients", Clinical Nuclear Medicine, vol. 18, No. 10, pp. 829-836 (1993).
N. Oehler, et al., "Bone microstructure is significantly altered in CRPS-affected distal tibiae as detected by HR-pQCT: a retrospective cross-sectional study", J Bone Mineral Metabolism (2019); 37: 741-748.
H.M. Oerlemans, et al., "Impairment Level SumScore in Reflex Sympathetic Dystrophy of One Upper Extremity", Arch Phys Med Rehabil 1998; 79:979-990.
K. Olson, et al., "Significance and impact of bisphosphonate-induced acute phase responses", J Oncol Pharm Practice (2007); 13: 223-229.
I.A. Orlova, et al., "MicroRNA modulation in complex regional pain syndrome", Journal of Translational Medicine 2011, 9: 195.
S. Palmer, et al., "Sensory Function and Pain Experience in Arthritis, Complex Regional Pain Syndrome, Fibromyalgia Syndrome, and Pain-Free Volunteers", Clin J Pain 2019; 35: 894-900.
A. Pankaj, et al., "Diagnosis of post-traumatic complex regional pain syndrome of the hand: current role of sympathetic skin response and three-phase bone scintigraphy",Journal of Orthopaedic Surgery 2006; 14(3): 284-90.
P.D. Papapetrou, "Bisphosphonate-associated adverse events", Hormones 2009; 8(2): 96-110.
A. Parinder, et al., "Associated factors, triggers and longterm outcome in Complex Regional Pain Syndrome (CRPS) in the upper limb—A descriptive cross-sectional study", PLoS One 20(3): e0320263 (2025).
J. Park, et al., "Time since last intravenous bisphosphonate and risk of osteonecrosis of the jaw in osteoporotic patients", Nature Communications (2025) 16:4367.
S. Park, et al., "Patterns of Three-Phase Bone Scintigraphy According to the Time Course of Complex Regional Pain Syndrome Type I After a Stroke or Traumatic Brain Injury", Clin Nucl Med 2009; 34: 773-776.
M. Pazanias, et al., "Eliminating the need for fasting with oral administration of bisphosphonates", Therapeutics and Clinical Risk Management 2013: 9 395-402.
G.L. Pellecchia, "Figure-of-eight Method of Measuring Hand Size: Reliability and Concurrent Validity", J Hand Ther. 2003; 16:300-304.

(56) References Cited

OTHER PUBLICATIONS

M.A. Perazella, et al., "Bisphosphonate neprotoxicity", Kidney International (2008) 74, 1385-1393.
R. Perez, et al., "Impairment level SumScore for lower extremity Complex Regional Pain Syndrome type I", Disability and Rehabilitation, 25:17, 984-991 (2003).
R.S.G.M. Perez, et al., "The treatment of complex regional pain syndrome type I with free radical scavengers: a randomized controlled study", Pain 102 (2003) 297-307.
T. Pfister, et al., "Acute Renal Effects of Intravenous Bisphosphonates in the Rat", Basic & Clinical Pharmacology & Toxicology 2005, 97, 374-381.
G. Pillai, et al., "Population pharmacokinetics of ibandronate in Caucasian and Japanese healthy males and postmenopausal females", International Journal of Clinical Pharmacology and Therapeutics, vol. 44, No. 12, pp. 655-667 (2006).
C. Pirri, et al., "An Emerging Perspective on the Role of Fascia in Complex Regional Pain Syndrome: A Narrative Review", Int. J. Mol. Sci. 2025; 26: 2826.
S.A. Polyzos, et al., "Paget's Disease of Bone and Calcium Homeostasis: Focus on Bisphosphonate Treatment", Exp Clin Endocrinol Diabetes 2011; 119: 519-524.
T. Pons, et al., "Potential Risk Factors for the Onset of Complex Regional Pain Syndrome Type 1: A Systematic Literature Review", Anesthesiology Research and Practice, vol. 2015, Article ID 956539, 15 pages.
A.G. Porras, et al., "Pharmacokinetics of Alendronate", Clin Pharmacokinet 1999; 36 (5) 315-328.
L.S. Radloff, "The CES-D Scale: A Self-Report Depression Scale for Research in the General Population", Applied Psychological Measurement, vol. 1, No. 3, pp. 385-401 (1977).
S. Ratcliffe, et al., "Randomized controlled study to evaluate the efficacy and safety of soticlestat as adjunctive therapy in adults with complex regional pain syndrome", Pain Medicine 2023; 24: 872-880.
I.R. Reid, et al., "Characterization of and Risk Factors for the Acute-Phase Response after Zoledronic Acid", J Clin Endocrinol Metab 95: 4380-4387 (2010).
I.R. Reid, et al., "Osteonecrosis of the jaw—Who gets it, and why?", Bone 44 (2009) 4-10.
M.C. Reilly, et al., "The Validity and Reproducibility of a Work Productivity and Activity Impairment Instrument", PharmacoEconomics 4(5): 353-365 (1993).
M. Ri, et al., "Ab Initio Investigation of Adsorption Characteristics of Bisphosphonates on Hydroxyapatite Surface"; The Royal Society of Chemistry, 1-8 (2010).
J.D. Ringe, et al., "A review of bone pain relief with ibandronate and other bisphosphonates in disorders of increased bone turnover", Clin Exp Rheumatol 2007; 25: 766-774.
R. Ringer, et al., "Concordance of qualitative bone scintigraphy results with presence of clincial complex regional pain syndrome 1: Meta-analysis of test accuracy studies", Eur J Pain 16 (2012) 1347-1356.
J.N. Robinson, et al., "Efficacy of Pamidronate in Complex Regional Pain Syndrome Type I", Pain Medicine vol. 5, No. 3, pp. 276-280 (2004).
G.A. Rodan, et al., "Bisphosphonate Mechanism of Action", Current Molecular Medicine 2002, 2, 571-577.
M. Roderick, et al., "Efficacy of pamidronate therapy in children with chronic non-bacterial osteitis: disease activity assessment by whole body magnetic resonance imaging", Rheumatology 2014; 53: 1973-1976.
M.J. Rogers, et al., "Molecular mechanisms of action of bisphosphonates and new insights into their effects outside the skeleton", Bone 139 (2020) 115493.
C.J. Rosen, et al., "IOM Committee Members Respond to Endocrine Society Vitamin D Guideline", J Clin Endocrinol Metab 97: 1146-1152 (2012).
J. Rosenstock, et al., "Pregabalin for the treatment of painful diabetic peripheral neuropathy: a double-blind, placebo-controlled trial", Pain 110 (2004) 628-638.
A.C. Ross, et al., "The 2011 Report on Dietary Reference Intakes for Calcium and Vitamin D from the Institute of Medicine: What Clinicians Need to Know", J Clin Endocrinol Metab, 96: 53-58 (2011).
S.L. Ruggiero, et al., "Bisphosphonate-related osteonecrosis of the jaw: background and guidelines for diagnosis, staging and management", OOOOE, vol. 102 No. 4 Oct. 2006, pp. 433-441.
S.L. Ruggiero, "Bisphosphonate-related osteonecrosis of the jaw: an overview", Ann. N.Y. Acad. Sci. 1218 (2011) 38-46.
M. Russo, et al., "A new hypothesis for the pathophysiology of complex regional pain syndrome", Medical Hypotheses 119 (2018) 41-53.
I. Ruza, et al., "Clinical experience with intravenous zoledronic acid in the treatment of male osteoporosis: evidence and opinions", Ther Adv Musculoskel Dis (2013) 5(4) 182-198.
P. Sandroni, et al., "Complex regional pain syndrome type I: incidence and prevalence in Olmsted county, a population-based study", Pain 103 (2003) 199-207.
G. Saviola, et al., "Clodronate and hydroxychloroquine in erosive osteoarthritis: a 24-month open randomized pilot study", Mod Rheumatol (2012) 22:256-263.
A. Sawicki, et al., "Influence of Calcitonin Treatment on the Osteocalcin Concentration in the Algodystrophy Bone", Clinical rheumatology, 1992, 11(3): 346-350.
A. Sayyad, et al., "Complex Regional Pain Syndrome Severity Score: Development of a Clinical Tool for Monitoring Disease Evolution", PM&R, vol. 3, Iss. 10S1, S281, poster 314 (2011).
R. Scala, et al., "Bisphosphonates Targeting Ion Channels and Musculoskeletal Effects", Front. Pharmacol. 13:837534 (2022).
C. Schinkel, et al., "Inflammatory Mediators are Altered in the Acute Phase of Posttraumatic Complex Regional Pain Syndrome", Clin J Pain 2006, 22: 235-239.
T. Schlereth, et al., "Inflammation in CRPS: Role of the sympathetic supply", Autonomic Neuroscience: Basic and Clinical 182 (2014) 102-107.
G.D. Schott, "Bisphosphonates for pain relief in reflex symapthetic dystrophy?", Lancet, vol. 350, p. 1117 (1997).
M. Schurmann, et al., "Peripheral sympathetic function as a predictor of complex regional pain syndrome type I (CRPS I) in patients with radial fracture", Autonomic Neuroscience: Basic and Clinical 86 (2000) 127-134.
Y. Abe, et al., "Improvement of pain and regional osteoporotic changes in the foot and ankle by low-dose bisphosphonate therapy for complex regional pain syndrome type I: a case series", Journal of Medical Case Reports 2011, 5:349.
S. Adami, et al., "Intravenous Neridronate in Adults with Osteogenesis Imperfecta", Journal of Bone and Mineral Research, vol. 18, No. 1, pp. 126-130 (2003).
S. Adami, et al., "Bisphosphonate therapy of reflex sympathetic dystrophy syndrome", Annals of the Rheumatic Diseases 1997; 56: 201-204.
G. Adami, et al., "Long-term effectiveness and predictors of bisphosphonate treatment in type I complex regional pain syndrome"; Clinical and Experimental Rheumatology 2024; 42: 961-966.
G. M. Alexander, et al., "Changes in cerebrospinal fluid levels of pro-inflammatory cytokines in CRPS", Pain 116 (2005) 213-219.
A. AlSharif, et al., "Is there a correlation between symptoms and bone scintigraphic findings in patients with complex regional pain syndrome?", Ann Nucl Med (2012) 26:665-669.
A. AlSharif, et al., "Standardization of quantitative single photon emission computed tomography in control individuals and in patients with condylar hyperplasia", Nuclear Medicine Communications 2014, 00:000-000.
M. Anitescu, "Novel Interventional Treatments in CRPS", presentation from the Pain Medicine Meeting 2024, 46 pages.
F. Antoniazzi, et al., "Early Bisphosphonate Treatment in Infants with Severe Osteogenesis Imperfecta", J. Pediatr 2006; 149:174-179.

(56) References Cited

OTHER PUBLICATIONS

R.M. Atkins, et al., "Aminohexane Diphosphonate in the Treatment of Paget's Disease of Bone", Journal of Bone and Mineral Research, vol. 2, No. 4, pp. 273-279 (1987).
R. M. Atkins, et al., "Quantitave Bone Scintigraphy in Reflex Sympathetic Dystrophy", British Journal of Rheumatology 1993; 32: 41-45.
T.M. Atkinson, et al., "The Brief Pain Inventory and Its 'Pain at Its Worst in the Last 24 Hours' Item: Clinical Trial Endpoint Considerations", Pain Medicine 2010; 11:337-346.
C.M. Bagi, et al., "Comparative Bone Anatomy of Commonly Used Laboratory Animals: Implications for Drug Discovery", Comparative Medicine, vol. 61, No. 1, pp. 76-85 (2011).
J. Barrett, et al., "Ibandronate: A Clinical Pharmacological and Pharmacokinetic Update", Journal of Clinical Pharmacology, 2004; 44:951-965.
B. Bazika-Gerasch, et al., "Compared to limb pain of other origin, ultrasonographic osteodensitometry reveals loss of bone density in complex regional pain syndrome", Pain 160 (2019) 1261-1269.
D.J. Bean, et al., "The efficacy of an interdisciplinary pain management program for complex regional pain syndrome compared to low back pain and chronic widespread pain: an observational study", Pain Medicine, 2025, 00, 1-9.
D.J. Bean, et al.; "Extent of recovery in the first 12 months of complex regional pain syndrome type-1: A prospective study", Eur J Pain 20 (2016) 884-894.
D.J. Bean, et al., "The Outcome of Complex Regional Pain Syndrome Type 1: A Systematic Review", The Journal of Pain, vol. 15, No. 7 Jul. 2014: 677-690.
A. Beerthuizen, et al.; "Demographic and medical parameters in the development of complex regional pain syndrome type 1 (CRPS1): Prospective study on 596 patients with a fracture", Pain 153 (2012) 1187-1192.
L.Z. Benet, et al., "Changes in plasma protein binding have little clinical relevance", Clinical Pharmacology & Therapeutics, vol. 71, No. 3, pp. 115-121 (2002).
M. Bernateck, et al., "The First Scintigraphic Detection of Tumor Necrosis Factor-Alpha in Patients with Complex Regional Pain Syndrome Type 1", Anesth Analg 2010; 110: 211-215.
F. Bertoldo, et al., "Definition, Assessment, and Management of Vitamin D Inadequacy: Suggestions, Recommendations, and Warnings from the Italian Society for Osteoporosis, Mineral Metabolism and Bone Diseases (SIOMMMS)", Nutrients 2022, 14, 4148.
K.D. Bharwani, et al., "Complex regional pain syndrome: diagnosis and treatment", BJA Education, vol. 17(8): 262-268 (2017).
K.D. Bharwani, et al., "Highlighting the Role of Biomarkers of Inflammation in the Diagnosis and Management of Complex Regional Pain Syndrome", Molecular Diagnosis & Therapy (2019) 23: 615-626.
F. Birklein et al., "Complex regional pain syndrome—phenotypic characteristics and potential biomarkers", Nat Rev Neurol. May 2018 ; 14(5): 272-284.
F. Birklein, et al., "Activation of Cutaneous Immune Responses in Complex Regional Pain Syndrome", The Journal of Pain, vol. 15, No. 5 May 2014: 485-495.
A. Borzutsky, et al., "Pediatric Chronic Nonbacterial Osteomyelitis", Pediatrics, vol. 130, No. 5, 1190-1197 (2012).
B.F. Boyce, et al., "Focal Osteomalacia Due to Low-Dose Diphosphonate Therapy in Paget's Disease", Lancet, pp. 821-824 (Apr. 14, 1984).
V. Braga, et al., "Bone mineral density is associated with pre-treatment pain levels of complex regional pain syndrome type 1 and predicts the response to N-containing bisphosphonates", Clinical and Experimental Rheumatology 2025; 43: 000-000.
S. Bruehl, et al., "An Update on the Pathophysiology of Complex Regional Pain Syndrome", Anesthesiology 2010; 113: 713-25.
S. Bruehl, et al., "Complex regional pain syndrome: evidence for warm and cold subtypes in a large prospective clinical sample", Pain, vol. 157, No. 8 (2016) 1674-1681.
S. Bruehl, et al., "Preoperative Predictors of Complex Regional Pain Syndrome Outcomes in the 6 Months Following Total Knee Arthroplasty", J Pain. Oct. 2022; 23(10): 1712-1723.
S. Bruehl, et al., "Complex regional pain syndrome", BMJ 2015, 350: h2730.
S. Bruehl, "Complex Regional Pain Syndrome: Outcomes and Subtypes", Clin J Pain 2009; 25: 598-599.
S. Bruehl, et al., "External validation of IASP diagnostic criteria for Complex Regional Pain Syndrome and proposed research diagnostic criteria", Pain 81 (1999) 147-154.
S. Bruehl, et al., "How common is complex regional pain syndrome—Type I?", Pain 129 (2007) 1-2.
F. Brunner, et al., "Bisphosphonates for the therapy of complex regional pain syndrome I—Systematic review", European Journal of Pain 13 (2009) 17-21.
L.D. Carbonare, et al., "Safety and tolerability of zoledronic acid and other bisphosphonates in osteoporosis management", Drug, Healthcare and Patient Safety 2010: 2 121-137.
S. Carda, et al., "Neridronate Treatment of Algodystrophy", 37th Congresso Nazionale Campobasso, Societa Italiana di Medicina Fisicae Riabilitativa, abstracts, p. 33 (2009).
S.A. Cave, et al., "Anxiety, Disability, and Pain Predict Outcomes of Complex Regional Pain Syndrome: An 8-year Follow-up of a Prospective", The Journal of Pain, vol. 24, No. 11 Nov. 2023: 1957-1967.
D. Cella, et al., "The Patient-Reported Outcomes Measurement Information System (PROMIS)—Progress of an NIH Roadmap Cooperative Group During its First Two Years", Med Care 2007; 45: S3-S11.
C. Chang, et al., "Complex regional pain syndrome Autoimmune or functional neurologic syndrome", Journal of Translational Autoimmunity 4 (2021) 100080.
N.A. Chartrand, et al., "Ocular Side Effects of Bisphosphonates: A Review of Literature", Journal of Ocular Pharmacology and Therapeutics, vol. 39, No. 1, pp. 3-16 (2023).
T. Chen, et al., "Pharmacokinetics and Pharmacodynamics of Zoledronic Acid in Cancer Patients with Bone Metastases", J Clin Pharmacol 2002; 42: 1228-1236.
W.K. Cheung, et al., "Pharmacokinetics of Pamidronate Disodium in Cancer Patients After a Single Intravenous Infusion of 30-, 60- or 90-mg Dose Over 4 or 24 Hours", American Journal of Therapeutics 1, 228-235 (1994).
J.H. Choi, et al., "Relationship Between HbA1c and Complex Regional Pain Syndrome in Stroke Patients With Type 2 Diabetes Mellitus", Ann Rehabil Med 2016; 40(5): 779-785.
S.W. Choi, et al., "PROsetta Stone Analysis Report—A Rosetta Stone for Patient Reported Outcomes", vol. 1, 273 pages (2015).
J. Ciaffi, et al., "Benign Evolution of Complex Regional Pain Syndrome (CRPS) Type 1 in Patients Treated with Intravenous Neridronate: A Single-Center Real-Life Experience", Pharmaceuticals 2024, vol. 17, 1500.
J.D. Clark, et al., "Autoinflammatory and autoimmune contributions to complex regional pain syndrome", Molecular Pain, vol. 14: 1-13 (2018).
V. Cocquyt, et al., "Pharmacokinetics of Intravenous Alendronate", Journal of Clinical Pharmacology, 1999; 39:385-393.
A. Mailis-Gagnon, "How Are Bone Scans Used in the Diagnosis and Treatment of CRPS?", 2015, https://rsds.org/how-are-bone-scans-used-in-the-diagnosis-and-treatment-of-crps/ 1/, retrieved Nov. 19, 2025.
ClinicalTrials.gov entry for NCT02402530, U.S. National Library of Medicine, Nov. 2018.
ClinicalTrials.gov entry for NCT03560986, U.S. National Library of Medicine, Nov. 2018.
ClinicalTrials.gov, Study Details for NCT02504008, U.S. National Library of Medicine, Mar. 2018.

* cited by examiner

| Left 150° | Right 150° |
|-----------|------------|
| Degrees | Degrees |

| Left | |
|------|--|
| Plantar 40° | Dorsal 20° |
| Degrees | Degrees |
| Right | |
| Plantar 40° | Dorsal 20° |
| Degrees | Degrees |

| Left | |
|---|---|
| Extension 0° | Flexion 150° |
| Degrees | Degrees |
| Right | |
| Extension 0° | Flexion 150° |
| Degrees | Degrees |

| Left | |
|---|---|
| Extension 60° | Flexion 60° |
| Degrees | Degrees |
| Right | |
| Extension 60° | Flexion 60° |
| Degrees | Degrees |

METHODS OF SELECTIVELY TREATING COMPLEX REGIONAL PAIN SYNDROME TYPE I (CRPS-I) USING BISPHOSPHONATE DERIVATIVES

The present application claims the benefit of U.S. Provisional Application No. 63/814,250, filed May 29, 2025, the entirety of which is incorporated by reference herein.

FIELD OF THE INVENTION

The disclosure relates to methods of selectively treating Complex Regional Pain Syndrome ("CRPS") Type 1 using aminobisphosphonate.

BACKGROUND

Complex Regional Pain Syndrome (CRPS) is a painful condition characterized by spontaneous and evoked regional pain, usually beginning in a distal extremity, that is disproportionate in magnitude or duration to the typical course of pain after similar tissue trauma. Sec Bruchl S., 2015, BMJ 351:h2730. It is distinguished from other persistent pain conditions by the presence of signs indicating prominent autonomic and inflammatory changes in the affected region. Id. In its most severe form, patients may present with a limb displaying extreme hyperalgesia and allodynia; obvious skin color, skin temperature, and sweating changes relative to the unaffected side; edema and altered patterns of hair, skin, or nail growth in the affected region; diminished strength; tremors; and in some cases, dystonia Id. CRPS is frequently associated with significant impairments in ability to work and function in daily life. CRPS is typically categorized as either excluding nerve injury (CRPS-Type 1 (CRPS-1)) or including peripheral nerve injury (CRPS-Type 2 (CRPS-2)).

To date, there are no Food and Drug Administration (FDA) approved pharmaceutical treatments for CRPS specifically, and patients are underserved due to lack of evidence for effective treatments.

There are currently no clear models for predicting efficacy of a treatment such as a bisphosphonate (e.g., aminobisphosphonates) in CRPS. Moreover, there is no known way to date to determine which specific subset of CRPS patients would be most likely to respond to aminobisphosphonate treatment. Moreover, given the side effects present with the administration of bisphosphonates, it may not be advisable to administer an aminobisphosphonate (e.g., neridronate) to patients that are unlikely to respond to the treatment. Thus, there remains a clear need for a viable methodology to selectively treat a specific subset of CRPS patients who would be most likely to benefit from the treatment.

Embodiments of the present disclosure fulfill this need and provide further related advantages.

SUMMARY OF THE DISCLOSURE

One aspect of the disclose pertains to a method of selectively treating Complex Regional Pain Syndrome ("CRPS") Type 1 comprising: (A) identifying a patient that has been diagnosed as having CRPS Type 1 as a patient that is likely to have a positive therapeutic response to aminobisphosphonate treatment and selecting that patient to receive treatment by confirming that the patient (i) has warm phase CRPS Type 1 and (ii) exhibits active bone phase in an affected limb; and (B) administering to the selected patient an amount of neridronate needed to achieve the positive therapeutic response.

DETAILED DESCRIPTION

Figure 1:
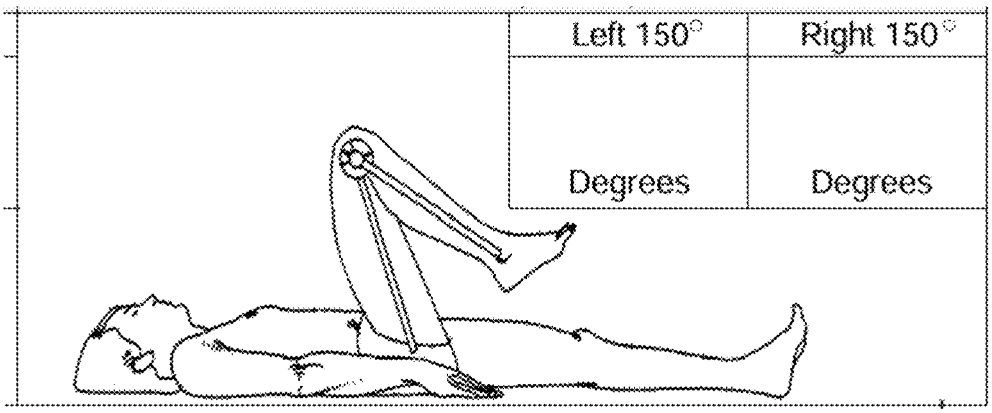
FIG. 1 is a graphical representation of knee flexion pertaining to Appendix 11 of Example 1.

This disclosure relates to methods of selectively treating Complex Regional Pain Syndrome ("CRPS") Type 1 comprising: (A) identifying a patient that has been diagnosed as having CRPS Type 1 as a patient that is likely to have a positive therapeutic response to aminobisphosphonate treatment and selecting that patient to receive treatment by confirming that the patient (i) has warm phase CRPS Type 1 and (ii) exhibits active bone phase in an affected limb; and (B) administering to the selected patient an amount of neridronate needed to achieve the positive therapeutic response.

In some embodiments, the positive therapeutic response is any one or more of a reduction in pain intensity, a reduction in the CRPS severity score, an increase in the Patient Global Impression of Change (PGI-C) in CRPS-Related Health score, an increase in the Short Form Health Survey (SF-36) Physical Functioning domain score, or an increase in active range of motion (AROM) of the affected limb compared to the contralateral limb.

In some embodiments, the positive therapeutic response is a reduction in pain intensity. In some embodiments, the positive therapeutic response is a reduction in pain intensity of 50% or more. In some embodiments, the positive therapeutic response is a reduction in pain intensity of 70% or more. In some embodiments, the positive therapeutic response is a reduction in pain intensity of 90% or more.

In some embodiments, the affected limb is an arm, hand, wrist, leg, ankle, or foot.

In some embodiments, confirming that the patient exhibits active bone phase in the affected limb is determined by a positive triple phase bone scan (TPBS). In some embodiments, the TPBS demonstrates increased uptake of a radiolabeled agent in the affected limb compared to the contralateral limb during Phase II and/or Phase III of the TPBS.

In some embodiments, confirming that the patient has warm phase CRPS Type 1 is done by observing moderate to severe edema in the affected limb and either color asymmetry in the affected limb relative to the contralateral limb or temperature asymmetry on the affected limb relative to the contralateral limb.

In some embodiments, confirming that the patient has warm phase CRPS Type 1 is done by observing edema in the affected limb and at least two of the following: 1) redness in the affected limb relative to the contralateral limb; 2) ≥1° C. increase in temperature on the affected limb relative to the contralateral limb; and 3) moderate to severe edema.

In some embodiments, confirming that the patient has warm phase CRPS Type 1 is done by observing edema and both redness and temperature increase in the affected limb compared to the contralateral limb.

Definitions

Unless defined otherwise, all technical and scientific terms used herein have the same meaning as is commonly understood by one of skill in the art to which this disclosure belongs.

As used herein, the singular forms "a," "an," and "the" include the plural reference unless the context clearly dictates otherwise.

As used herein, the term "and/or" includes any and all combinations of one or more of the associated listed items.

Except where otherwise indicated, all numbers expressing quantities of ingredients, time periods, and so forth used in the disclosure and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not to be considered as an attempt to limit the application of the doctrine of equivalents to the scope of the claims, each numerical parameter should be construed in light of the number of significant digits and ordinary rounding conventions.

Additionally, the disclosure of numerical ranges within this specification is considered to be a disclosure of all numerical values and ranges within that range. For example, if a range is from about 1 to about 50, it is deemed to include, for example, 1, 7, 34, 46.1, 23.7, 50 or any other value or range within the range. Moreover, as used herein, the term "at least" includes the stated number, e.g., "at least 50" includes 50.

All references cited herein, including patent applications and publications, are incorporated by reference in their entirety for any purpose.

As used herein, "patient" or "subject" refers to a human in need of treatment. In some embodiments, the patient is a human. In some embodiments, the patient is an adult human (i.e., ≥18 years of age). In some embodiments, the patient is less than 18 years old.

As used herein, "administering" and variants thereof (e.g., "administration") refers to prescribing a medicine to a human patient (i.e., selected patient), directing others to administer a medicine to a human patient (i.e., selected patient), directing a human patient (i.e., selected patient) to self-administer a medicine, and/or the act of physically injecting and/or ingesting the medicine. A medicine containing an aminobisphosphonate as its active pharmaceutical ingredient, can therefore be administered by a physician or other medical professional who writes prescriptions for a medicine(s) or otherwise directs a human patient (i.e., selected patient) to self-administer a prescription, and/or by the human patient (i.e., selected patient) who injects and/or ingests the medicine and/or by a human patient's caretaker who injects the medicine into a human patient or who provides the medicine to a human subject.

As used herein, "therapeutically effective amount" and similar descriptions such as "an amount efficacious for treatment" or "an effective dose" or "an amount needed to achieve a positive therapeutic response" refers to the amount necessary at the intended dosage to elicit the biological or medical response of a tissue, a system, animal or human that is being sought by a researcher, veterinarian, medical doctor or other clinician. The desired response may be, for example, the alleviation, amelioration, reduction or cessation of at least one symptom associated with the treated condition. In an embodiment, the term "therapeutically effective amount" means an amount of an aminobisphosphonate that alleviates at least one clinical symptom in a human patient. For example, a therapeutically effective amount can be an amount needed to achieve a positive therapeutic response. Amounts may vary, as a person of ordinary skill in the art will appreciate, according to various factors, including but not limited to the disease type and state, age, sex, and weight of the individual, the particular compound, the route of administration, and the frequency and/or duration of dosing. The response may be measured by one or more recognized techniques, for example, by in vitro assay, in vivo non-human animal studies, and/or further supported from clinical trials.

"Treat," "treatment," or "treating," as used herein refers to administering a therapeutic agent or pharmaceutical composition to a patient for therapeutic purposes. The terms "treat," "treating," and "treatment" and variants thereof are meant to include alleviating or abrogating a disorder, disease, or condition; or one or more of the symptoms associated with the disorder, disease, or condition; or preventing, alleviating or eradicating the cause(s) of the disorder, disease, or condition itself. As used herein, the term "alleviate" is meant to describe a process by which the severity of a sign or symptom of a disease or disorder is decreased. Importantly, a sign or symptom can be alleviated without being eliminated. In some embodiments, the administration disclosed herein leads to the elimination of a sign or symptom, however, elimination is not required.

For example, with respect to treating CRPS Type 1, such treatment includes, alleviation of at least one of the symptoms associated therewith, including, but not limited to, reduction in pain intensity, reduction in the severity of CRPS, improvement in physical functioning, hyperalgesia, allodynia, edema, skin color asymmetry (i.e., redness), temperature asymmetry, sweating asymmetry, dystrophic changes of nails, hair and/or skin, weakness, muscles tremors, dystonia, and/or myoclonus.

As used herein, the term "aminobisphosphonate treatment" refers to a treatment comprising administration of an aminobisphosphonate.

As used herein, the term "neridronate treatment" refers to a treatment comprising administration of neridonate.

As used herein, the term "pharmaceutically acceptable salt" refers to a salt of an active agent (e.g., neridronic acid) that is substantially non-toxic to living organisms, e.g., subjects in need of methods of treatment. Typical pharmaceutically acceptable salts include those salts prepared by reaction of the one or more active components of the disclosure with an inorganic or organic acid, or an organic base, depending on the substituents present on the one or more active components of the disclosure.

Inorganic acids which may be used to prepare pharmaceutically acceptable salts of the active components include, but are not limited to, hydrochloric acid, phosphoric acid, sulfuric acid, hydrobromic acid, hydroiodic acid, phosphorous acid and the like. Organic acids which may be used to prepare pharmaceutically acceptable salts include, without limitation, aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include, but are not limited to, hydrochloride, hydrobromide, nitrate, sulfate, pyrosulfate, bisulfate, sulfite, bisulfite, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, and maleate. Suitable pharmaceutically acceptable salts may also be formed by reacting the active components with an organic base such as methylamine, ethylamine, ethanolamine, lysine, ornithine and the like. Pharmaceutically acceptable salts include the salts formed between carboxylate or sulfonate groups that may be found on some of the active components and inorganic cations, such as sodium, potassium, ammonium, or calcium, or such organic cations as isopropylammonium, trimethylammonium, tetramethylammonium, and imidazolium.

As used herein, a "week" means seven consecutive days. As used herein, a "month" means 28-31 consecutive days or about four weeks.

The methods of the disclosure comprise (A) identifying a patient that has been diagnosed as having CRPS Type 1 as a patient that is likely to have a positive therapeutic response to aminobisphosphonate treatment and selecting that patient to receive treatment by confirming that the patient (i) has warm phase CRPS Type 1 and (ii) exhibits active bone phase in the affected limb; and (B) administering to the selected patient a therapeutically effective amount of aminobisphosphonate.

In some embodiments, the methods of the disclosure comprise (A) identifying a patient that has been diagnosed as having CRPS Type 1 as a patient that is likely to have a positive therapeutic response to aminobisphosphonate treatment and selecting that patient to receive treatment by confirming that the patient (i) has warm phase CRPS Type 1 and (ii) exhibits active bone phase in an affected limb; and (B) administering to the selected patient an amount of neridronate needed to achieve the positive therapeutic response.

In some embodiments, the patient is a human. In some embodiments, the patient is a human adult (e.g., being 18 years of age or older). In some embodiments, the patient is a human child (e.g., being less than 18 years of age). In some embodiments, the patient is a human child having an age ranging from 2 years to less than 18 years. In some embodiments, the patient is a human child having an age ranging from 5 years to less than 18 years. In some embodiments, the patient is a human child having an age ranging from 5 years to 17 years. In some embodiments, the patient is a human child having an age ranging from 7 years to 17 years. In some embodiments, the patient is a human child having an age ranging from 13 years to less than 18 years.

As used herein, the term "selected patient" is any patient within the meaning of the disclosure that has been or can be selected to receive aminobisphosphonate treatment (e.g., neridronate treatment). In some embodiments, a selected patient is a patient that is likely to have a positive therapeutic response to aminobisphosphonate treatment. In some embodiments, a selected patient is a patient that is likely to have a positive therapeutic response to neridronate treatment. In some embodiments, a selected patient is a patient that has been diagnosed or can be diagnosed as having CRPS Type 1 and identified or can be identified as a patient that is likely to have a positive therapeutic response to aminobisphosphonate treatment (e.g., neridronate treatment). A selected patient can be a patient that has already been diagnosed as having CRPS Type 1 (e.g., by a medical professional) or a patient has not yet been diagnosed for CRPS Type 1 but has the signs or symptoms necessary to receive a CRPS Type 1 diagnosis. In some embodiments, a selected patient is a patient that has already been diagnosed as having CRPS Type 1 (e.g., by a medical professional) or a patient has not yet been diagnosed for CRPS Type 1 but has the signs or symptoms necessary to receive a CRPS Type 1 diagnosis, wherein no other diagnosis can better explain the signs and symptoms. A selected patient can be a patient that has already been identified as a patient that is likely to have a positive therapeutic response to aminobisphosphonate treatment (e.g., neridronate treatment) or a patient that has not yet been identified by can be identified a patient that is likely to have a positive therapeutic response to aminobisphosphonate treatment (e.g., neridronate treatment) according to the disclosure.

In some embodiments, a selected patient is a patient that has been diagnosed or can be diagnosed as having CRPS Type 1 and has been identified as being likely to have a positive therapeutic response to aminobisphosphonate treatment (e.g., neridronate treatment) by confirming that the patient (i) has warm phase CRPS Type 1 and (ii) exhibits active bone phase in the affected limb. In some embodiments, a patient that is likely to have a positive therapeutic response to aminobisphosphonate treatment (e.g., neridronate treatment) is a patient that has been diagnosed with CRPS Type 1, has warm phase CRPS Type 1, and exhibits active bone phase in the affected limb.

CRPS can be diagnosed using systematically developed and validated diagnostic criteria often referred to as the Budapest Clinical Criteria. These diagnostic criteria are endorsed by the International Association for the Study of Pain (IASP) and have recently been incorporated into the latest version of the International Classification of Diseases (ICD-11). CRPS is intended to be a broad diagnosis designed to encompass the range of pain conditions which can be associated with vasomotor and sudomotor disturbances. As is evident from examining the Budapest Clinical Criteria listed in Table 1 below, patients experiencing unexplained disproportionate pain can meet the CRPS diagnostic criteria based on very different clinical phenotypes. For example, both a patient displaying warm, red skin in the affected area with prominent edema and weakness and a patient displaying severe allodynia with increased sweating, cold/bluish skin, and changes in skin texture in the affected area can meet the diagnostic criteria. Patients meeting the CRPS criteria are formally classified as having either CRPS Type 1 (CRPS-1) or CRPS Type 2 (CRPS-2), with the main difference being that patients with CRPS-2 display evidence of peripheral nerve injury in the affected area while patients with CRPS Type 1 do not. CRPS Type 1 is more common, representing up to 90% of all cases of CRPS. At present, there are no other official clinical CRPS subtypes designated to reflect distinct clinical presentations commonly seen in patients with CRPS although various subtypes beyond CRPS Type 1 and CRPS Type 2 are referenced in the medical literature.

A diagnosis of CRPS Type 1 can be made, for example, according to the Budapest Clinical Criteria along with a finding of no known peripheral nerve injury. Historically, a positive triple-phase bone scan (TPBS) was also used to make a diagnosis of CRPS, but the diagnostic performance of TPBS for CRPS Type 1 has been highly variable, including in relation to Budapest Clinical Criteria. (Kwon et. al 2011). After the establishment of the Budapest Clinical Criteria, a positive TPBS was no longer required or recommended for accurate diagnosis.

TABLE 1

| Budapest Clinical Diagnostic Criteria for CRPS. | |
|---|---|
| New IASP diagnostic criteria for complex regional pain syndrome ("Budapest criteria") (A-D must apply) | |
| A. The patient has continuing pain which is disproportionate to the inciting event | ☐ |
| B. The patient reports at least one symptom in 3 or more of the categories | ☐ |
| C. The patient displays at least one sign in 2 or more of the categories | ☐ |
| D. No other diagnosis can better explain the signs and symptoms | ☐ |

| Category | | Symptom (the patient reports a problem) | Sign (you can see or feel a problem on examination) |
|---|---|---|---|
| 1 "Sensory" | Allodynia (to light touch/brush stroke and/or temperature sensation and/or deep somatic pressure and/or joint movement), and/or hyperalgesia (to pinprick) | Reported hyperesthesia also qualifies as a symptom ☐ | ☐ |
| 2 "Vasomotor" | Temperature asymmetry and/or skin color changes and/or skin color asymmetry | ☐ | ☐ |
| 3 "Sudomotor/oedema" | Oedema and/or sweating changes and/or sweating asymmetry | ☐ | ☐ |
| 4 "Motor/trophic" | Decreased range of motion and/or motor dysfunction (weakness, tremor, dystonia) and/or trophic changes (hair/nail/skin) | ☐ | ☐ |

* Additionally, to be diagnosed as CRPS-1, there must be no known peripheral nerve injury.

As used herein, the terms "affected limb" or "affected region" or "involved limb" or "involved region" are used interchangeably and refer to the location of the body with CRPS Type 1. In some embodiments, the affected limb or region is an arm, hand, wrist, shoulder, finger, leg, ankle, foot, hip, and/or toe. In some embodiments, the affected limb or region is an arm, hand, wrist, leg, ankle, and/or foot. In some embodiments, a selected patient has only one affected limb. In some embodiments, a selected patient has more than one affected limb.

As used herein, the terms "contralateral limb" or "contralateral region" are used interchangeably and refer to the location (limb/region) that is healthy or normal and otherwise equivalent (e.g., symmetrically on the other side of the body) to the affected limb or region but without CRPS Type 1.

The methods of the disclosure comprise identifying a patient that has been diagnosed as having CRPS Type 1 as a patient that is likely to have a positive therapeutic response to aminobisphosphonate treatment (e.g., neridronate treatment) and selecting that patient to receive treatment (e.g., aminobisphosphonate treatment, e.g., neridronate treatment) for CRPS Type 1 by confirming that the patient has warm phase CRPS Type 1 and exhibits active bone phase in the affected limb.

"Warm phase CRPS Type 1" or "warm phase CRPS-1", as used herein, refers to a subtype of CRPS Type 1 which may be characterized by edema and asymmetrically warm and/or red skin as disclosed herein. When a patient is in the warm phase, the affected limb may show pathognomonic inflammation (i.e., red, warm, swollen, tender) and levels of proinflammatory cytokines such as interleukin-6 (IL-6) and tumor necrosis factor alpha (TNFα) may be elevated in the affected area.

In some embodiments, the methods of the disclosure comprise confirming that the selected patient has warm phase CRPS Type 1. Confirming that the selected patient has warm phase CRPS Type 1 can be done by observing certain signs or symptoms. It will be understood that the "observing" encompasses observing done by a medical professional (e.g., a medical professional who is performing the steps of "identifying" and/or "selecting" a patient in the methods of the disclosure). It will be understood that any method of "observing" is included within the meaning of the disclosure as would be understood by a person of ordinary skill in the art. For example, "observing" can be done by visual inspection and/or by means of relevant tools (e.g., the use of a thermometer for "observing" temperature asymmetry). In some embodiments, a single person performs the steps of "identifying", "selecting", and "confirming" (including by "observing") in the methods of the disclosure. In some embodiments, the steps of "identifying", "selecting", and/or "confirming" (including by "observing") in the methods of the disclosure are performed by different people (e.g., different medical professionals). In some embodiments, a single person performs the steps of "identifying", "selecting", and/or "confirming" (including by "observing") as well as "administering" in the methods of the disclosure. In some embodiments, the steps of "identifying", "selecting", and/or "confirming" (including by "observing") and "administering" in the methods of the disclosure are performed by different people (e.g., different medical professionals). For example, in an embodiment, one medical professional could perform the steps of "identifying", "selecting", and "confirming", while a second medical professional could perform the step of "administering".

In some embodiments, confirming that the selected patient has warm phase CRPS Type 1 is done by observing moderate to severe edema in the affected limb and either color asymmetry (i.e., redness) in the affected limb relative to the contralateral limb or temperature asymmetry (i.e., increase in temperature or warm skin) on the affected limb relative to the contralateral limb. In some embodiments, confirming that the selected patient has warm phase CRPS Type 1 is done by observing moderate to severe edema in the affected limb and color asymmetry (i.e., redness) in the affected limb relative to the contralateral limb. In some embodiments, confirming that the selected patient has warm phase CRPS Type 1 is done by observing moderate to severe edema in the affected limb and temperature asymmetry in the affected limb relative to the contralateral limb. In some embodiments, confirming that the selected patient has warm phase CRPS Type 1 is done by observing moderate to severe edema in the affected limb and both color asymmetry (i.e., redness) in the affected limb relative to the contralateral limb and temperature asymmetry on the affected limb relative to the contralateral limb.

In some embodiments, confirming that the selected patient has warm phase CRPS Type 1 is done by observing edema in the affected limb and at least two of the following: 1) redness in the affected limb relative to the contralateral limb; 2) ≥1° C. increase in temperature on the affected limb relative to the contralateral limb; and 3) moderate to severe edema. In some embodiments, confirming that the selected patient has warm phase CRPS Type 1 is done by observing edema in the affected limb and at least two of the following: 1) redness in the affected limb relative to the contralateral limb; 2) ≥1° C. increase in temperature on the affected limb relative to the contralateral limb; and 3) moderate to severe edema.

In some embodiments, warm phase CRPS Type 1 is present (i.e., as determined by confirming that the selected patient has warm phase CRPS Type 1) where at least two of the following are observed: (i) moderate to severe edema in the affected limb, (ii) color asymmetry (i.e., redness) in the affected limb relative to the contralateral limb, and (iii) temperature asymmetry on the affected limb relative to the contralateral limb. In some embodiments, warm phase CRPS Type 1 is present where at least two of the following are observed: (i) moderate to severe edema, (ii) color asymmetry (i.e., redness) in the affected limb relative to the contralateral limb, and (iii) ≥1° C. increase in temperature on the affected limb relative to the contralateral limb.

In some embodiments, confirming that a patient has warm phase CRPS Type 1 is done by observing edema and both redness (i.e., color asymmetry) and temperature increase (i.e., temperature asymmetry) compared to the contralateral limb.

In some embodiments, confirming that the selected patient has warm phase CRPS Type 1 is done by observing mild edema in the affected limb and either color asymmetry (i.e., redness) in the affected limb relative to the contralateral limb or temperature asymmetry (i.e., increase in temperature) on the affected limb relative to the contralateral limb. In some embodiments, confirming that the selected patient has warm phase CRPS Type 1 is done by observing mild edema in the affected limb and color asymmetry (i.e., redness) in the affected limb relative to the contralateral limb. In some embodiments, confirming that the selected patient has warm phase CRPS Type 1 is done by observing mild edema in the affected limb and temperature asymmetry in the affected limb relative to the contralateral limb.

In some embodiments, warm phase CRPS Type 1 is present where the following are observed: (i) mild edema in the affected limb, (ii) color asymmetry (i.e., redness) in the affected limb relative to the contralateral limb, and (iii) temperature asymmetry on the affected limb relative to the contralateral limb.

In some embodiments, warm phase CRPS Type 1 is present where the patient exhibits: (i) mild edema with both color asymmetry (e.g., red skin) and temperature asymmetry (i.e., warm skin) in the affected limb compared to the contralateral limb, (ii) moderate edema with color asymmetry (e.g., red skin) and/or temperature asymmetry (i.e., warm skin) in the affected limb compared to the contralateral limb, or (iii) severe edema with color asymmetry (e.g., red skin) and/or temperature asymmetry (i.e., warm skin) in the affected limb compared to the contralateral limb.

In some embodiments, temperature asymmetry (i.e., warm skin) is an increase in temperature on the affected limb of ≥0.5° C. to ≥5° C., or any amount or range therebetween, relative to the contralateral limb. In some embodiments, warm skin is an increase in temperature on the affected limb of ≥0.5° C., or ≥1° C., or ≥1.5° C., or ≥1.8° C., or ≥2° C., or ≥2.5° C., or ≥2.8° C., or ≥3° C., or ≥3.5° C., or ≥4° C., or ≥4.5° C., or ≥5° C. relative to the contralateral limb. In some embodiments, temperature asymmetry is an increase in temperature on the affected limb of ≥0.5° C. relative to the contralateral limb. In some embodiments, temperature asymmetry is an increase in temperature on the affected limb of ≥1.0° C. relative to the contralateral limb. In some embodiments, temperature asymmetry (i.e., warm skin) is an increase in temperature on the affected limb of ≥1.5° C. relative to the contralateral limb. In some embodiments, temperature asymmetry is an increase in temperature on the affected limb of ≥1.8° C. relative to the contralateral limb. In some embodiments, temperature asymmetry (i.e., warm skin) is an increase in temperature on the affected limb of ≥2° C. relative to the contralateral limb.

In some embodiments, warm phase CRPS Type 1 is present where the patient has moderate to severe edema in the affected limb, and at least one of the following: (i) color asymmetry (i.e., red skin) in the affected limb relative to the contralateral limb, and (ii) temperature asymmetry (i.e., warm skin) on the affected limb relative to the contralateral limb. In some embodiments, warm phase CRPS Type 1 is present where the patient has moderate to severe edema in the affected limb, and at least one of the following: (i) color asymmetry (i.e., redness) in the affected limb relative to the contralateral limb, and (ii) ≥1° C. increase in temperature on the affected limb relative to the contralateral limb.

Edema may be defined, for example, on a scale of 0-3, where: 0 (none) is defined as no visible edema; 1 (mild) is defined as visible edema but bony landmarks are clearly visible; 2 (moderate) is defined as visible edema but bony landmarks are obscured; and 3 (severe) is defined as very severe visible edema without visible bony landmarks and/or with notable skin tightness). Edema may also be assessed by comparing the circumference of the affected limb/region and to the circumference of the contralateral limb/region.

Temperature differences between an affected limb and a contralateral limb (i.e., temperature asymmetry) may be measured, for example, by a thermometer, including, for example, a digital infrared thermometer and/or by thermography. Temperature asymmetry may also be determined by touch (e.g., feeling the affected and contralateral limb with a hand).

In some embodiments, the selected patient has moderate to severe edema in the affected limb. In some embodiments, the selected patient has moderate edema in the affected limb. In some embodiments, the selected patient has severe edema in the affected limb.

In some embodiments, the selected patient has color asymmetry (i.e., redness) in the affected limb relative to the contralateral limb. Color asymmetry can be determined for example by visual inspection of the affected limb and the contralateral limb.

In some embodiments, the selected patient has temperature asymmetry (i.e., warm skin) on the affected limb relative to the contralateral limb. In some embodiments, the selected patient exhibits an increase in skin temperature on the affected limb relative to the contralateral limb. In some embodiments, the selected patient exhibits at least a 0.5° C., or at least a 0.75° C., or at least a 1° C. (i.e., ≥1° C.), or at least a 2° C., or at least a 3° C., or at least a 4° C. increase in temperature on the affected limb relative to the contralateral limb. In some embodiments, the selected patient exhibits at least a 1° C. (i.e., ≥1° C.) increase in temperature on the affected limb relative to the contralateral limb.

In some embodiments, the selected patient has moderate to severe edema in the affected limb and color asymmetry (i.e., redness) in the affected limb relative to the contralateral limb. In some embodiments, the selected patient has moderate to severe edema in the affected limb and temperature asymmetry on the affected limb relative to the contralateral limb. In some embodiments, the selected patient has moderate to severe edema in the affected limb and a ≥1° C. increase in temperature on the affected limb relative to the contralateral limb. In some embodiments, the selected patient has (i) moderate to severe edema in the affected limb, (ii) color asymmetry (i.e., redness) in the affected limb relative to the contralateral limb, and (iii) temperature asymmetry on the affected limb relative to the contralateral limb. In some embodiments, the selected patient has (i) moderate to severe edema in the affected limb, (ii) color asymmetry (i.e., redness) in the affected limb relative to the contralateral limb, and (iii) and a ≥1° C. increase in temperature on the affected limb relative to the contralateral limb.

In some embodiments, the selected patient exhibits active bone phase in an affected limb. In some embodiments, the selected patient exhibits greater bone resorption in the affected limb relative to the contralateral limb. In some embodiments, the selected patient exhibits increased bone metabolism in the affected limb relative to the contralateral limb. In some embodiments, the selected patient exhibits increased hydroxyapatite deposition in the affected limb relative to the contralateral limb. In some embodiments, the selected patient exhibits increased bone formation in the affected limb relative to the contralateral limb. In some embodiments, the selected patient exhibits bone marrow edema in the affected limb. In some embodiments, the selected patient exhibits active bone phase only in an affected limb. In some embodiments, the selected patient does not exhibit active bone phase in the contralateral limb. In some embodiments, the selected patient does not exhibit active bone resorption in the contralateral limb.

It is understood that any method of confirming that a patient exhibits active bone phase in an affected limb is within the scope of the disclosure.

As used herein, the term "exhibits active bone phase" or "in an active bone phase" is used to indicate some level of bone involvement or bone-related mechanisms. For example, "active bone phase" may be used to describe a patient or affected region/limb/bone that exhibits, e.g., increased metabolic activity including increased bone metabolism, increased bone resorption, increased bone formation, bone marrow edema, increased hydroxyapatite deposition at the zone of mineralization, or increased inflammatory activity.

In some embodiments, confirming that a patient exhibits active bone phase in an affected limb is determined by obtaining a positive triple-phase bone scan (TPBS).

It is understood that a triple-phase bone scan (TPBS) is a nuclear medicine imaging technique used to evaluate various bone conditions and diseases. It is a diagnostic imaging technique that uses radioactive tracers (i.e., radioactive agent) to capture images of bone activity at three different time points: blood flow (Phase I), blood pool (Phase II), and bone metabolism (Phase III). In some embodiments, the radiolabeled agent is injected into a vein and travels through blood to bones and organs. In some embodiments, images are taken at three different times, e.g., during or shortly after the injection of the radioactive tracer to evaluate blood flow in the vessels (Phase I), at a second time point several minutes after the injection of the radioactive tracer to assess soft tissue involvement and blood pooling outside the vasculature and in tissues, often indicative of local inflammation (Phase II), and at a third time point hours after the injection of the radioactive tracer to evaluate bone metabolism activity (i.e., enhanced hydroxyapatite deposition at the zone of mineralization) and uptake of the tracer in the bones (Phase III).

In some embodiments, the radiolabeled agent comprises [$^{153}$Sm]Sm-lexidronam. In some embodiments, the radiolabeled agent comprises a radiolabeled bisphosphonate derivative. In some embodiments, the radiolabeled agent comprises a radiolabeled bisphosphonate derivative, wherein the radiolabeled bisphosphonate derivative comprises $^{32}$P. In some embodiments, the radiolabeled bisphosphonate derivative comprises a complex comprising a bisphosphonate derivative and a radioactive isotope. In some embodiments, the radiolabeled bisphosphonate derivative comprises a complex comprising a bisphosphonate derivative and $^{18}$F, $^{89}$Sr, $^{186}$Re, $^{188}$Re, $^{58}$Ga, $^{177}$Lu, or $^{223}$Ra. In some embodiments, the radiolabeled bisphosphonate derivative comprises a complex comprising a bisphosphonate derivative and $^{186}$Re and $^{188}$Re. In some embodiments, the radiolabeled bisphosphonate derivative comprises methylene diphosphonate (MDP), butedronate, ethane-1-hydroxy-1,1-diphosphonate (EHDP), oxidronate, pyrophosphate, or methylene hydroxydiphosphonate (HDP) complexed with Technetium 99-m. In some embodiments, the radiolabeled bisphosphonate derivative comprises Tc99mmethylene diphosphonate [MDP]. In some embodiments, the radiolabeled bisphosphonate derivative is injected in an amount of about 20 to about 30 millicuries (mCi). Additional suitable techniques, radiolabeled bisphosphonate derivatives, and dosages thereof for TPBS are described in Thimothy Dinh et al. (Triple Phase Bone Scan. 2023 Aug. 8. In: StatPearls. StatPearls Publishing, Treasure Island (FL); 2023. PMID: 30571011).

It is understood that other bone scans (e.g., MRI and X-ray) do not use a radiolabeled bisphosphonate and have demonstrated limited utility in CRPS.

In some embodiments, the positive TPBS is determined by observing an increased uptake of the radiolabeled agent (e.g., the radiolabeled bisphosphonate derivative) in one or more regions (e.g., in the involved region or limb or affected region or limb) of the patient as compared to one or more otherwise equivalent regions (e.g., in a contralateral limb) of the subject, during Phase I, Phase II, Phase III, or any combination thereof, of the TPBS.

Without wishing to be bound by theory, it is understood that a positive TPBS is due to increased binding of the radiolabeled [tracer/agent] to hydroxyapatite in one or more bones.

In some embodiments, the positive TPBS is determined by observing an increased uptake of the radiolabeled agent (e.g., the radiolabeled bisphosphonate derivative) in one or more bones of the subject as compared to one or more contralateral bones of the subject, during Phase I, Phase II, Phase III, or any combination thereof, of the TPBS.

In some embodiments, the positive TPBS is determined by observing an increased uptake of the radiolabeled agent (e.g., the radiolabeled bisphosphonate derivative) in the affected limb of the subject, as compared to a contralateral limb of the patient, during Phase I, Phase II, Phase III, or any combination thereof, of the TPBS.

In some embodiments, the positive TPBS shows increased uptake of the radiolabeled agent (e.g., the radiolabeled bisphosphonate derivative) during Phase I. In some embodiments, the positive TPBS shows increased uptake of the radiolabeled agent (e.g., the radiolabeled bisphosphonate derivative) during Phase II. In some embodiments, the positive TPBS shows increased uptake of the radiolabeled agent (e.g., the radiolabeled bisphosphonate derivative) during Phase I and Phase II. In some embodiments, the positive TPBS shows increased uptake of the radiolabeled agent (e.g., the radiolabeled bisphosphonate derivative) during Phase II and Phase III. In some embodiments, the positive TPBS shows increased uptake of the radiolabeled agent (e.g., the radiolabeled bisphosphonate derivative) during Phase III. In some embodiments, the positive TPBS shows increased uptake of the radiolabeled agent (e.g., the radiolabeled bisphosphonate derivative) during Phase I, Phase II, and Phase III.

In some embodiments, confirming that a patient exhibits active bone phase is determined by obtaining a positive triple-phase bone scan (TPBS). In some embodiments, confirming that a patient exhibits active bone phase is determined by obtaining a positive triple-phase bone scan (TPBS) within about 12 months or less, or about 11 months or less, or about 10 months or less, or about 9 months or less, or about 8 months or less, or about 7 months or less, or about 6 months or less, or about 5 months or less, or about 4 months or less, or about 3 months or less, or about 2 months or less, or about 1 month or less of the onset of one or more symptoms of CRPS-I. In some embodiments, confirming that a patient exhibits active bone phase is determined by obtaining a positive triple-phase bone scan (TPBS) within about 12 months or less, or about 11 months or less, or about 10 months or less, or about 9 months or less, or about 8 months or less, or about 7 months or less, or about 6 months or less, or about 5 months or less, or about 4 months or less, or about 3 months or less, or about 2 months or less, or about 1 month or less of diagnosis of CRPS-I. In some embodiments, confirming that a patient exhibits active bone phase is determined by obtaining a positive triple-phase bone scan (TPBS) within about 12 months or less, or about 11 months or less, or about 10 months or less, or about 9 months or less, or about 8 months or less, or about 7 months or less, or about 6 months or less, or about 5 months or less, or about 4 months or less, or about 3 months or less, or about 2 months or less, or about 1 month or less of confirming that the patient has warm phase CRPS-I.

In some embodiments, confirming that a patient exhibits active bone phase is determined by demonstrating increased uptake of a radiolabeled bisphosphonate in the affected limb compared to the contralateral side.

In some embodiments, demonstrating increased uptake of a radiolabeled bisphosphonate in the affected limb compared to the contralateral side is achieved by a TBPS scan. In some embodiments, demonstrating increased uptake of a radiolabeled bisphosphonate in the affected limb compared to the contralateral limb is achieved by a TBPS scan showing asymmetrical increased uptake in any phase between the affected limb and the contralateral limb.

In some embodiments, the positive TPBS is used to predict a positive therapeutic response of the selected patient to the administration of a therapeutically effective amount of an aminobisphosphonate (e.g., neridronate (e.g., sodium neridronate)). In some embodiments, the positive TPBS in combination with a determination of warm phase CRPS Type 1 is used to predict a positive therapeutic response of the selected patient to the administration of a therapeutically effective amount of an aminobisphosphonate (e.g., neridronate (e.g., sodium neridronate)).

Without wishing to be bound by theory, it is understood that a "negative" TPBS may be determined by observing a decreased uptake of the radiolabeled bisphosphonate derivative in one or more limbs of the subject as compared to one or more otherwise equivalent limbs of the subject, e.g., during Phase I, Phase II, and Phase III of the TPBS.

In some embodiments, confirming that a patient exhibits active bone phase is determined by a positive triple phase bone scan (TPBS) demonstrating increased uptake of a radiolabeled agent in the affected limb compared to the contralateral limb during Phase II and/or Phase III of the TPBS.

Without wishing to be bound by theory, it is understood that a "negative" TPBS may be determined by observing a substantially similar uptake of the radiolabeled bisphosphonate derivative in one or more limbs of the subject as compared to one or more otherwise equivalent limbs of the subject, e.g., during Phase I, Phase II, and Phase III of the TPBS.

It is understood that Phase I of TPBS may also be referred to as "the blood-flow phase", "flow phase", or "angiographic phase". It is understood that Phase II of TPBS may also be referred to as "the blood-pool phase". It is understood that Phase III of TPBS may also be referred to as "the delayed phase". It is understood that TPBS may also be referred to as "three-phase bone scintigraphy".

The methods of the disclosure comprise administering to a selected patient a therapeutically effective amount of an aminobisphosphonate.

It is understood that the term "aminobisphosphonate," as used herein, refers to a bisphosphonate derivative of the following general formula:

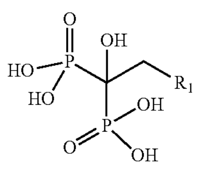

or a pharmaceutically acceptable salt thereof, wherein $R_1$ is an aliphatic or aromatic group containing at least one nitrogen atom. Examples of aminobisphosphonates include, but are not limited to, pamidronic acid; alendronic acid; 5-amino-1-hydroxy-1,1-pentanediphosphonic acid; neridronic acid; 7-amino-1-hydroxy-1,1-heptanediphosphonic acid; 8-amino-1-hydroxy-1,1-octanediphosphonic acid;

olpadronic acid; ibandronic acid; zoledronic acid; and risedronic acid; or a pharmaceutically acceptable salt thereof. It will be understood that the term "aminobisphosphonate" encompasses a solvate, hydrate, polymorph, stereoisomer, or prodrug thereof in any form.

In some embodiments, the aminobisphosphonate is pamidronic acid; alendronic acid; 5-amino-1-hydroxy-1,1-pentanediphosphonic acid; neridronic acid; 7-amino-1-hydroxy-1,1-heptanediphosphonic acid; 8-amino-1-hydroxy-1,1-octanediphosphonic acid; olpadronic acid; ibandronic acid; zoledronic acid; risedronic acid; or a pharmaceutically acceptable salt thereof.

In some embodiments, the aminobisphosphonate is pamidronic acid or a pharmaceutically acceptable salt thereof.

In some embodiments, the aminobisphosphonate is alendronic acid or a pharmaceutically acceptable salt thereof.

In some embodiments, the aminobisphosphonate is 5-amino-1-hydroxy-1,1-pentanediphosphonic acid or a pharmaceutically acceptable salt thereof.

In some embodiments, the aminobisphosphonate is 7-amino-1-hydroxy-1,1-heptanediphosphonic acid or a pharmaceutically acceptable salt thereof.

In some embodiments, the aminobisphosphonate is 8-amino-1-hydroxy-1,1-octanediphosphonic acid or a pharmaceutically acceptable salt thereof.

In some embodiments, the aminobisphosphonate is olpadronic acid or a pharmaceutically acceptable salt thereof.

In some embodiments, the aminobisphosphonate is ibandronic acid or a pharmaceutically acceptable salt thereof.

In some embodiments, the aminobisphosphonate is zoledronic acid or a pharmaceutically acceptable salt thereof.

In some embodiments, the aminobisphosphonate is risedronic acid or a pharmaceutically acceptable salt thereof.

In some embodiments, the aminobisphosphonate is neridronic acid or a pharmaceutically acceptable salt thereof.

In some embodiments, the methods of the disclosure comprise administering to the selected patient a therapeutically effective amount of neridronate. In some embodiments, the methods of the disclosure comprise administering to the selected patient a therapeutically effective amount of neridronic acid. In some embodiments, the methods of the disclosure comprise administering to the selected patient a therapeutically effective amount of a pharmaceutically acceptable salt of neridronic acid. In some embodiments, the neridronic acid or a pharmaceutically acceptable salt thereof is a lithium salt, a sodium salt, or a potassium salt of neridronic acid. In some embodiments, the neridronic acid or a pharmaceutically acceptable salt thereof is sodium neridronate.

In some embodiments, the methods of the disclosure comprise administering to the selected patient an amount of neridronate needed to achieve a positive therapeutic response. In some embodiments, the methods of the disclosure comprise administering to the selected patient an amount of neridronate needed to achieve a positive therapeutic response. In some embodiments, the methods of the disclosure comprise administering to the selected patient an amount of a pharmaceutically acceptable salt of neridronate needed to achieve a positive therapeutic response. In some embodiments, the neridronate or a pharmaceutically acceptable salt thereof is a lithium salt, a sodium salt, or a potassium salt of neridronic acid. In some embodiments, the neridronate or a pharmaceutically acceptable salt thereof is sodium neridronate.

It will be understood that the term "neridronate" encompasses neridronic acid as well as a pharmaceutically acceptable salt, solvate, hydrate, polymorph, stereoisomer, or prodrug thereof in any form. For example, the neridronic acid or a pharmaceutically acceptable salt thereof may be in a solid form, which may be in crystal or amorphous form, and includes solvates and hydrates thereof, all of which are encompassed within the scope of the disclosure. In some embodiments, the neridronate is sodium neridronate.

Neridronate is an alkyl-aminobisphosphonate that has been studied in patients with CRPS, Paget's disease of bone, osteogenesis imperfecta, hypercalcemia, and osteoporosis. Neridronate is considered to work in CRPS via several mechanisms. For example, neridronate may exhibit inhibitory effects on activated mononuclear cells, keratinocytes, dendritic cells and glial cells. Without wishing to be bound by theory, it is thought that this inhibition may result in decreased release of inflammatory mediators by these cells and inhibition of proinflammatory changes that sensitize nociceptors (leading to hyperalgesia) and contribute to inflammatory-related CRPS features. Neridronate's anticipated effects on preserving and improving bone architecture through stabilization of hydroxyapatite crystals and potential neurologic effects (e.g., by decreasing calcium influx, inhibiting activated glial cells, downregulating nociceptive signaling by inhibiting post-translations modification of GTPases) are also important. For these effects to occur, it is advantageous if neridronate (or another aminobisphosphonate) is preferentially distributed in the affected limb. In some embodiments, the distribution of neridronate (or another aminobisphosphonate) in the affected limb is predicted by a TPBS scan showing increased uptake of a radio-labeled bisphosphonate, when done within a short time period (e.g., ≤3 months) before administering neridronate.

It is understood that the term "neridronic acid", as used herein, refers to a bisphosphonate derivative having the following structure:

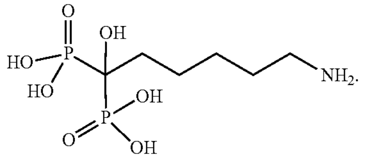 [SMILES: NCCCCCC(O)(P(=O)(O)O)P(=O)(O)O]

It is understood that the term "sodium neridronate", as used herein, refers to a bisphosphonate derivative having the following structure:

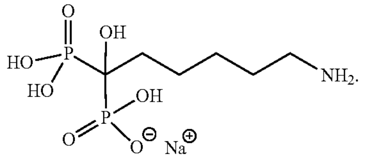 [SMILES: NCCCCCC(O)(P(=O)([O-])O)P(=O)(O)O ; [Na+]]

In some embodiments, the aminobisphosphonate (e.g., neridronate) is administered in any amount needed to treat at least one symptom. In some embodiments, the aminobisphosphonate (e.g., neridronate) is administered in any amount needed to treat at least one symptom of CRPS. In some embodiments, the aminobisphosphonate (e.g., neridronate) is administered in any amount needed to treat at least one symptom of CRPS Type 1. In some embodiments, the aminobisphosphonate (e.g., neridronate) is administered in any amount needed to treat at least one symptom of warm-phase CRPS Type 1.

In some embodiments, the aminobisphosphonate (e.g., neridronate) is administered in any safe amount.

In some embodiments, the aminobisphosphonate (e.g., neridronate) is administered in any amount needed to achieve a positive therapeutic response. In some embodiments, the aminobisphosphonate (e.g., neridronate) is administered in any amount needed to achieve a positive therapeutic response in a selected patient.

As used here in, a "positive therapeutic response" refers to a biological or medical response of a tissue, a system, animal or human that is being sought by a researcher, veterinarian, medical doctor or other clinician or medical professional. The positive therapeutic response may be, for example, the alleviation, amelioration, reduction or cessation of at least one symptom associated with the treated condition. In an embodiment, the term "positive therapeutic response" means the alleviation of at least one clinical symptom in a human patient. The response may be measured or observed by one or more recognized techniques, for example, by in vitro assay, in vivo non-human animal studies, by observation, through the use of recognized tools, and/or further supported from clinical trials. For example, with respect to treating CRPS Type 1, a positive therapeutic response includes alleviation of at least one of the symptoms associated therewith, including, but not limited to, reduction in pain intensity, reduction in severity of CRPS, improvement in physical functioning, edema, skin color asymmetry, and/or skin temperature asymmetry.

In some embodiments, the symptom of CRPS Type 1 comprises, in the affected region(s) pain (e.g., burning pain, throbbing pain), sensitivity to cold, sensitivity to touch, hyperalgesia, allodynia, pain with movement, skin color asymmetry (i.e., redness), skin temperature asymmetry, sweating asymmetry, edema (i.e., swelling), dystrophic changes of nails, hair and/or skin (e.g., a change in patterns of hair growth, a change in the skin texture, and/or a change in nail growth), a reduction in strength (i.e., weakness), muscle tremors, myoclonus, dystonia, joint stiffness, or any combination thereof.

In some embodiments, the positive therapeutic response is a reduction in pain intensity, a reduction in the CRPS severity score, an increase in the Patient Global Impression of Change (PGI-C) in CRPS-Related Health score, an increase in the Short Form Health Survey (SF-36) Physical Functioning domain score, and/or an increase in active range of motion (AROM) of the affected limb compared to the contralateral limb.

In some embodiments, the "positive therapeutic response" is a reduction in pain intensity. A reduction in pain intensity can be measured using any known technique as would be understood by a person of ordinary skill in the art. In some embodiments, the reduction in pain intensity is determined by using a 7-day average of twice-daily "pain now" assessments on the 11-point numeric rating scale (NRS). In some embodiments, the reduction in pain intensity is determined by using a 7-day average of the twice-daily "worst pain" assessments (over a half-day recall period) on the 11-point numeric rating scale (NRS). In some embodiments, the reduction in pain intensity is determined by measuring the change from baseline.

In some embodiments, the "positive therapeutic response" is a 20% or more, 30% or more, 40% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more reduction in pain intensity. In some embodiments, the "positive therapeutic response" is a 30% or more reduction in pain intensity. In some embodiments, the "positive therapeutic response" is a 50% or more reduction in pain intensity. In some embodiments, the "positive therapeutic response" is a 70% or more reduction in pain intensity. In some embodiments, the "positive therapeutic response" is a 90% or more reduction in pain intensity.

In some embodiments, the "positive therapeutic response" is a reduction in pain evoked by active motion. In some embodiments, the "positive therapeutic response" is a 20% or more, 30% or more, 40% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more reduction in pain evoked by active motion.

In some embodiments, the "positive therapeutic response" is a reduction in edema (i.e., swelling) of the affected limb. In some embodiments, the "positive therapeutic response" is a 20% or more, 30% or more, 40% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more reduction in edema.

In some embodiments, the "positive therapeutic response" is a reduction in the severity of CRPS. In some embodiments, the reduction in the severity of CRPS is determined by using a CRPS severity score (CSS). In some embodiments, the "positive therapeutic response" is a reduction in the CRPS severity score. In some embodiments, the reduction in in the CRPS severity score is determined by measuring the change from baseline.

In some embodiments, the "positive therapeutic response" is an increase in the Patient Global Impression of Change (PGI-C) in CRPS-Related Health score.

In some embodiments, the positive therapeutic response is an improvement in physical functioning. In some embodiments, the improvement in physical functioning is determined by using a Short Form Health Survey (SF-36) Physical Functioning domain. In some embodiments, the positive therapeutic response is an increase in the Short Form Health Survey (SF-36) Physical Functioning domain score. In some embodiments, the physical functioning is determined by measuring the change from baseline.

In some embodiments, the positive therapeutic response is an increase in active range of motion (AROM) of the affected limb compared to the contralateral limb. In some embodiments, the active range of motion (AROM) is determined by measuring the change from baseline. The active range of motion can be measured, for example, by goniometry.

In some embodiments, the "positive therapeutic response" is a reduction in hyperalgesia of the affected limb. In some embodiments, the "positive therapeutic response" is a reduction in allodynia of the affected limb. In some embodiments, the "positive therapeutic response" is a reduction in temperature asymmetry between the affected limb and the contralateral limb. In some embodiments, the "positive therapeutic response" is a reduction in color asymmetry between the affected limb and the contralateral limb. In some embodiments, the "positive therapeutic response" is a reduction in sweating asymmetry between the affected limb and the contralateral limb.

In some embodiments, a positive therapeutic response can occur one day, or two days, or three days, or four days, or five days, or six days, or seven days (i.e., one week), or 1.5 weeks, or 2 weeks, or 3 weeks, or 4 weeks, or 5 weeks, or 6 weeks, or 7 weeks, or 8 weeks, or 9 weeks, or 10 weeks, or 11 weeks, or 12 weeks, or 13 weeks, or 14 weeks, or 15 weeks after the administration.

"Amounts" and "concentrations" may vary, as a person of ordinary skill in the art will appreciate, according to various factors, including but not limited to the disease type and state, age, sex, and weight of the individual, the particular active compound (e.g., an aminobisphosphonate, e.g., neridronate), the route of administration, and the frequency and/or duration of dosing. The response may be measured by one or more recognized techniques, for example, by in vivo non-human animal studies and/or further supported from clinical trials.

The doses or dosages recited herein for neridronate are based on the molecular weight of the compound itself, rather than the molecular weight of the pharmaceutically acceptable salt thereof, or the hydrate or solvate thereof, or the co-crystal thereof, or any excipients in the composition, unless otherwise stated. For example, administration of neridronate or the pharmaceutically acceptable salt thereof at a dosage of 400 mg per day means administration of the equivalent of 400 mg of the compound itself per day, not 400 mg of the pharmaceutically acceptable salt thereof, or the hydrate or solvate thereof, or the co-crystal thereof, per day.

In some embodiments, the aminobisphosphonate (e.g., neridronate) is administered at a total dose amount of about 1000±50 mg, about 1000±50 mg, about 1000±40 mg, about 1000±30 mg, about 1000±20 mg, about 1000±10 mg, about 1000±5 mg, about 1000±4 mg, about 1000±3 mg, about 1000±2 mg, or about 1000±1 mg (e.g., about 1000 mg).

In some embodiments, the aminobisphosphonate (e.g., neridronate) is administered at a total dose amount of about 900±50 mg, about 900±50 mg, about 900±40 mg, about 900±30 mg, about 900±20 mg, about 900±10 mg, about 900±5 mg, about 900±4 mg, about 900±3 mg, about 900±2 mg, or about 900±1 mg (e.g., about 900 mg).

In some embodiments, the aminobisphosphonate (e.g., neridronate) is administered at a total dose amount of about 800±50 mg, about 800±50 mg, about 800±40 mg, about 800±30 mg, about 800±20 mg, about 800±10 mg, about 800±5 mg, about 800±4 mg, about 800±3 mg, about 800±2 mg, or about 800±1 mg (e.g., about 800 mg).

In some embodiments, the aminobisphosphonate (e.g., neridronate) is administered at a total dose amount of about 700±50 mg, about 700±50 mg, about 700±40 mg, about 700±30 mg, about 700±20 mg, about 700±10 mg, about 700±5 mg, about 700±4 mg, about 700±3 mg, about 700±2 mg, or about 700±1 mg (e.g., about 700 mg).

In some embodiments, the aminobisphosphonate (e.g., sodium neridronate) is administered at a total dose amount of about 600±50 mg, about 600±50 mg, about 600±40 mg, about 600±30 mg, about 600±20 mg, about 600±10 mg, about 600±5 mg, about 600±4 mg, about 600±3 mg, about 600±2 mg, or about 600±1 mg (e.g., about 600 mg).

In some embodiments, the aminobisphosphonate (e.g., neridronate) is administered at a total dose amount of about 500±50 mg, about 500±50 mg, about 500±40 mg, about 500±30 mg, about 500±20 mg, about 500±10 mg, about 500±5 mg, about 500±4 mg, about 500±3 mg, about 500±2 mg, or about 500±1 mg (e.g., about 500 mg).

In some embodiments, the aminobisphosphonate (e.g., neridronate) is administered at a total dose amount of about 400±50 mg, about 400±50 mg, about 400±40 mg, about 400±30 mg, about 400±20 mg, about 400±10 mg, about 400±5 mg, about 400±4 mg, about 400±3 mg, about 400±2 mg, or about 400±1 mg (e.g., about 400 mg).

In some embodiments, the aminobisphosphonate (e.g., neridronate) is administered at a total dose amount of about 300±20 mg, about 300±10 mg, about 300±5 mg, about 300±4 mg, about 300±3 mg, about 300±2 mg, or about 300±1 mg (e.g., about 300 mg).

In some embodiments, the aminobisphosphonate (e.g., neridronate) is administered at a total dose amount of about 200±20 mg, about 200±10 mg, about 200±5 mg, about 200±4 mg, about 200±3 mg, about 200±2 mg, or about 200±1 mg (e.g., about 200 mg).

In some embodiments, the aminobisphosphonate (e.g., neridronate) is administered at a total dose amount of about 100±20 mg, about 100±10 mg, about 100±5 mg, about 100±4 mg, about 100±3 mg, about 100±2 mg, or about 100±1 mg (e.g., about 100 mg).

In some embodiments, the aminobisphosphonate (e.g., neridronate) is administered at a total dose amount of about 50±10 mg, about 50±5 mg, about 50±4 mg, about 50±3 mg, about 50±2 mg, or about 50±1 mg (e.g., about 50 mg).

In some embodiments, the aminobisphosphonate (e.g., neridronate) is administered at a total dose amount of about 25±5 mg, about 25±4 mg, about 25±3 mg, about 25±2 mg, or about 25±1 mg (e.g., about 25 mg).

The aminobisphosphonate or a pharmaceutical composition comprising the aminobisphosphonate may be administered by any appropriate route of administration. Potential routes of administration include without limitation oral or parenteral (including for example, intramuscular, subcutaneous or intravenous).

In some embodiments, the aminobisphosphonate, or a pharmaceutical composition comprising the aminobisphosphonate, is administered to the patient orally, intravenously, and/or intramuscularly. In some embodiments, the administration is oral. In some embodiments, the administration is intravenous. In some embodiments, the administration is intramuscular. In some embodiments, the administration is oral and intravenous. In some embodiments, the administration is oral and intramuscular. In some embodiments, the administration is intravenous and intramuscular.

In some embodiments, the aminobisphosphonate (e.g., sodium neridronate) is administered orally, parenterally (i.e., intramuscularly or intravenously), or a combination thereof. In some embodiments, the aminobisphosphonate (e.g., sodium neridronate) is administered orally. In some embodiments, the aminobisphosphonate (e.g., sodium neridronate) is administered parenterally. In some embodiments, the aminobisphosphonate (e.g., sodium neridronate) is administered intramuscularly. In some embodiments, the aminobisphosphonate (e.g., sodium neridronate) is administered intravenously.

In some embodiments, the aminobisphosphonate (e.g., sodium neridronate) is administered in a single dose, or in two divided doses, or in three divided doses, or in four divided doses, or in five divided doses, or in six divided doses, or in seven divided doses, or in eight divided doses, or in nine divided doses, or in ten divided doses, or in eleven divided doses, or in twelve divided doses, or in thirteen divided doses, or in fourteen divided doses, or in fifteen, or in sixteen divided doses.

In some embodiments, the aminobisphosphonate (e.g., sodium neridronate) is administered parenterally in a single dose, or in two divided doses, or in three divided doses, or in four divided doses, or in five divided doses, or in six divided doses, or in seven divided doses, or in eight divided doses, or in nine divided doses, or in ten divided doses, or in eleven divided doses, or in twelve divided doses, or in thirteen divided doses, or in fourteen divided doses, or in fifteen, or in sixteen divided doses. In some embodiments, the aminobisphosphonate (e.g., sodium neridronate) is administered parenterally in two or more divided doses. In some embodiments, the aminobisphosphonate (e.g., sodium neridronate) is administered parenterally in three or more divided doses. In some embodiments, the aminobisphosphonate (e.g., sodium neridronate) is administered parenterally in four or more divided doses. In some embodiments, the aminobisphosphonate (e.g., sodium neridronate) is administered parenterally in eight divided doses. In some embodiments, the aminobisphosphonate (e.g., sodium neridronate) is administered parenterally in sixteen divided doses.

In some embodiments, the aminobisphosphonate (e.g., sodium neridronate) is administered intravenously in a single dose, or in two divided doses, or in three divided doses, or in four divided doses, or in eight divided doses. In some embodiments, the aminobisphosphonate (e.g., sodium neridronate) is administered intravenously in two or more divided doses. In some embodiments, the aminobisphosphonate (e.g., sodium neridronate) is administered intravenously in three or more divided doses. In some embodiments, the aminobisphosphonate (e.g., sodium neridronate) is administered intravenously in four or more divided doses. In some embodiments, the aminobisphosphonate (e.g., sodium neridronate) is administered intravenously in four divided doses.

In some embodiments, the aminobisphosphonate (e.g., sodium neridronate) is administered intramuscularly in a single dose, or in two divided doses, or in three divided doses, or in four divided doses, or in five divided doses, or in six divided doses, or in seven divided doses, or in eight divided doses, or in sixteen divided doses. In some embodiments, the aminobisphosphonate (e.g., sodium neridronate) is administered intramuscularly in two or more divided doses. In some embodiments, the aminobisphosphonate (e.g., sodium neridronate) is administered intramuscularly in three or more divided doses. In some embodiments, the aminobisphosphonate (e.g., sodium neridronate) is administered intramuscularly in four or more divided doses. In some embodiments, the aminobisphosphonate (e.g., sodium neridronate) is administered intramuscularly in four divided doses. In some embodiments, the aminobisphosphonate (e.g., sodium neridronate) is administered intramuscularly in sixteen divided doses.

In some embodiments, the aminobisphosphonate (e.g., sodium neridronate) is administered by injection (e.g., subcutaneous, intramuscular, or intravenous injection). In some embodiments, the aminobisphosphonate (e.g., sodium neridronate) is administered by two or more injections. In some embodiments, the aminobisphosphonate (e.g., sodium neridronate) is administered by 1, or 2, or 3, or 4, or 5, or 6, or 7, or 8, or 9, or 10, or 11, or 12, or 13, or 14, or 15, or 16, or 17, or 18, or 19, or 20 injections. In some embodiments, the aminobisphosphonate (e.g., sodium neridronate) is administered by 4 injections. In some embodiments, the aminobisphosphonate (e.g., sodium neridronate) is administered by 8 injections. In some embodiments, the aminobisphosphonate (e.g., sodium neridronate) is administered by 16 injections.

In some embodiments, the aminobisphosphonate (e.g., sodium neridronate) is administered by intravenous infusion. In some embodiments, the aminobisphosphonate (e.g., sodium neridronate) is administered by two or more intravenous infusions. In some embodiments, the aminobisphosphonate (e.g., sodium neridronate) is administered by 1, or 2, or 3, or 4, or 5, or 6, or 7, or 8, or 9, or 10, or 11, or 12, or 13, or 14, or 15, or 16, or 17, or 18, or 19, or 20 intravenous infusions. In some embodiments, the aminobisphosphonate (e.g., sodium neridronate) is administered by 2 intravenous infusions. In some embodiments, the aminobisphosphonate (e.g., sodium neridronate) is administered by 4 intravenous infusions. In some embodiments, the aminobisphosphonate (e.g., sodium neridronate) is administered by 8 intravenous infusions. In some embodiments, the aminobisphosphonate (e.g., sodium neridronate) is administered by 16 intravenous infusions.

In some embodiments, each intravenous infusion of the aminobisphosphonate (e.g., sodium neridronate) is administered for between 10 minutes to six hours, or 20 minutes to six hours, or 30 minutes to six hours, or 40 minutes to six hours, or 50 minutes to six hours, or one to six hours, or one to five hours, or one to four hours, or one to three hours, or one to two hours, or two to three hours, or 1.5 to 3 hours, or 1.5 to 2.5 hours, or 2 hours to 2.5 hours.

In some embodiments, each intravenous infusion of the aminobisphosphonate (e.g., sodium neridronate) is administered for at least one hour, or at least two hours, or at least three hours, or at least four hours, or at least five hours, or at least six hours, or at least seven hours, or at least eight hours.

In some embodiments, the aminobisphosphonate (e.g., sodium neridronate) is administered twice a day (i.e., twice daily), or daily, or every other day, or twice a week, or three times a week, or four times a week, or five times a week, or six times a week, or weekly, or bi-weekly, or three times in two weeks, or four times in two weeks, or five times in two weeks, or three times a month, or once a month (i.e., monthly), or once every other month, or once every three months, or once every four months. In some embodiments, the administration is daily. In some embodiments, the administration is four times in two weeks. In some embodiments, the administration is four times in 10 days.

In some embodiments, the (aminobisphosphonate (e.g., neridronate (e.g., sodium neridronate)) is administered over 12 weeks or less, or 11 weeks or less, or 10 weeks or less, or 9 weeks or less, or 8 weeks or less, or 7 weeks or less, or 6 weeks or less, or 5 weeks or less, or 4 weeks or less, or 3 weeks or less, or two weeks or less.

In some embodiments, the (aminobisphosphonate (e.g., neridronate (e.g., sodium neridronate)) is administered over between 5 days and 12 weeks, or between 10 days and 12 weeks, or between 10 days and 10 weeks, or between 10 days and 8 weeks, or between 10 days and 6 weeks, or between 10 days and 4 weeks, or between 10 days and 3 weeks, or between 10 days and 2 weeks, or any range therebetween.

In some embodiments, the (aminobisphosphonate (e.g., neridronate (e.g., sodium neridronate)) is administered over 20 days, or 19 days, or 18 days, or 17 days, or 16 days, or 15 days, or 14 days, or 13 days, or 12 days, or 11 days, or 10 days, or 9 days, or 8 days, or 7 days, or 6 days, or 5 days, or 4 days, or 3 days, or 2 days, or 1 day.

In some embodiments, the (aminobisphosphonate (e.g., neridronate (e.g., sodium neridronate)) is administered over 10 days. In some embodiments, the (aminobisphosphonate (e.g., neridronate (e.g., sodium neridronate)) is administered by two or more divided doses over 10 days. In some embodiments, the (aminobisphosphonate (e.g., neridronate (e.g., sodium neridronate)) is administered by two or more intravenous infusions over 10 days. In some embodiments, the (aminobisphosphonate (e.g., neridronate (e.g., sodium neridronate)) is administered by two divided doses over 10 days. In some embodiments, the (aminobisphosphonate (e.g., neridronate (e.g., sodium neridronate)) is administered by three divided doses over 10 days. In some embodiments, the (aminobisphosphonate (e.g., neridronate (e.g., sodium neridronate)) is administered by four divided doses over 10 days. In some embodiments, the (aminobisphosphonate (e.g., neridronate (e.g., sodium neridronate)) is administered by five divided doses over 10 days.

In some embodiments, the (aminobisphosphonate (e.g., neridronate (e.g., sodium neridronate)) is administered by four intravenous infusions over 10 days. In some embodiments, the (aminobisphosphonate (e.g., neridronate (e.g., sodium neridronate)) is administered over 10 days on days 1, 4, 7, and 10.

In some embodiments, the (aminobisphosphonate (e.g., neridronate (e.g., sodium neridronate)) is administered during a first administration cycle (e.g., 10 days (e.g., on days 1, 4, 7, and 10)), and then administered during a second administration cycle (e.g., 10 days (e.g., on days 1, 4, 7, and 10)).

In some embodiments, the second administration cycle starts after 8 weeks, or after 9 weeks, or after 10 weeks, or after 11 weeks, or after 12 weeks, or after 13 weeks, or after 14 weeks, or after 15 weeks, or after 16 weeks, or after 20 weeks from the end of the first administration cycle.

In some embodiments, a patient having a poor response or no response to the first administration cycle will receive a second administration cycle.

In some embodiments, the (aminobisphosphonate (e.g., neridronate (e.g., sodium neridronate)) is administered by intravenous infusion over 10 days on days 1, 4, 7, and 10, wherein each intravenous infusion is administered for about two hours.

In some embodiments, the (aminobisphosphonate (e.g., neridronate (e.g., sodium neridronate)) is administered by intravenous infusion over 10 days on days 1, 4, 7, and 10, wherein each intravenous infusion is administered for between about two and about three hours.

In some embodiments, the aminobisphosphonate (e.g., neridronate (e.g., sodium neridronate)) is administered by intravenous infusion during a first administration cycle of 10 days (e.g., on days 1, 4, 7, and 10), and then administered by intravenous infusion during a second administration cycle of 10 days (e.g., on days 1, 4, 7, and 10), wherein each intravenous infusion is administered for about two hours.

In some embodiments, the (aminobisphosphonate (e.g., neridronate (e.g., sodium neridronate)) is administered by intravenous infusion during a first administration cycle of 10 days (e.g., on days 1, 4, 7, and 10), and then administered by intravenous infusion during a second administration cycle of 10 days (e.g., on days 1, 4, 7, and 10), wherein each intravenous infusion is administered for between about two hours and about three hours.

In some embodiments, the administration is discontinued after the alleviation or reduction of at least one symptom. In some embodiments, the administration is intermittent. For example, in some embodiments, the administration may be discontinued temporarily and then the administration may be started again at a later time.

In some embodiments, the administration is according to a variable dosing regimen (e.g., the aminobisphosphonate (e.g. neridronate) may be administered daily for 1 or more weeks and then once daily or less for the duration of treatment). In some embodiments, the frequency of administration may be reduced. In some embodiments, the frequency of administration may be increased. In some embodiments, administration may be as needed (e.g., the aminobisphosphonate (e.g., sodium neridronate) may be administered when at least one symptom develops or worsens and use may be discontinued when at least one symptom is alleviated).

In some embodiments, the aminobisphosphonate (e.g., neridronate (e.g., sodium neridronate)) is administered within about 12 months, or 11 months, or 10 months, or 9 months, or 8 months, or 7 months, or 6 months, or 5 months, or 4 months, or 3 months, or 2 months, or 1 month of the onset of one or more symptoms of CRPS-I. In some embodiments, the aminobisphosphonate (e.g., neridronate (e.g., sodium neridronate) is administered within about 12 months, or 11 months, or 10 months, or 9 months, or 8 months, or 7 months, or 6 months, or 5 months, or 4 months, or 3 months, or 2 months, or 1 month of the onset of one or more symptoms of warm-phase CRPS Type 1.

In some embodiments, the aminobisphosphonate (e.g., neridronate (e.g., sodium neridronate)) is administered within between about 1 month and about 6 months, or between about 1 month and 5 months, or between about 1 month and 4 months, or between about 1 month and 3 months, or between about 1 month and 2 months, or between about 2 months and 6 months, or between about 2 months and 5 months, or between about 2 months and 4 months, or between about 2 months and 3 months, or between about 3 months and 6 months, or between about 3 months and 5 months, or between about 3 months and 4 months, or between about 4 months and 6 months, or between about 5 months and 6 months, or between about 6 months and 7 months, or between about 6 months and 8 months, or between about 6 months and 10 months, or between about 6 months and 12 months of the onset of one or more symptoms of CRPS-I.

Formulation of an aminobisphosphonate (e.g., neridronate) or a pharmaceutical composition comprising an aminobisphosphonate (e.g., neridronate) can take any suitable form for the desired route of administration. Proper formulation can depend on various factors, such as the mode of administration chosen.

Where the administration is oral, any suitable orally deliverable dosage form can be used. The oral dosage forms according to the disclosure can be solid, semi-solid or liquid. Such oral dosage forms include, but are not limited to, powders, dispersible granules, mini-tablets, and beads (which can be used, for example, for tableting, encapsulation, or direct administration), pills, tablets, lacquered tablets, sugar-coated tablets, hard and soft capsules including gelatin capsules, lozenges, rapidly dissolving tablets, aqueous, alcoholic or oily solutions, gels, syrups, emulsions or suspensions. The oral dosage forms according to the disclosure may comprise additionally one or more coatings which modify release properties, for example, coatings which impart delayed release or formulations which have extended release properties. Also included in the present disclosure are formulations which are intended to be converted, shortly before use, to a suspension or a solution; examples include, but are not limited to, freeze-dried formulations and liquid formulations adsorbed into a solid absorbent medium. including without limitation tablets, capsules (solid or liquid filled), powders, granules, syrups and other liquids, elixirs, troches, lozenges, gels, pastes, solutions or suspensions in an aqueous liquid or/and a non-aqueous liquid, or oil-in-water liquid emulsions or water-in-oil liquid emulsions.

Injectable compositions or i.v. infusions can be provided, for example, in the form of solutions, suspensions, and emulsions.

In some embodiments, the administration is subcutaneous. In some embodiments, the subcutaneous administration is made with an injection device.

In some embodiments, subcutaneous administration may be performed by injection using a syringe, or using other injection devices, injector pens, or needleless devices. An injection device is usually a device that introduces a substance into the body of a patient via a parenteral route, e.g., intramuscular, subcutaneous or intravenous. For example, an injection device may be a syringe (e.g., pre-filled with a pharmaceutical composition, such as an auto-injector) which, for example, includes a cylinder or barrel for holding fluid to be injected (e.g., aminobisphosphonate (e.g., sodium neridronate)), a needle for piecing skin and/or blood vessels for injection of the fluid; and a plunger for pushing the fluid out of the cylinder and through the needle bore. In an embodiment, an injection device is an autoinjector, a jet injector or an external infusion pump.

In some embodiments, the aminobisphosphonate (e.g., neridronate), or a pharmaceutical composition comprising the aminobisphosphonate (e.g., neridronate), can be formulated for parenteral administration by injection or infusion.

Advantages of intravenous administration include, for example, direct administration of a therapeutic agent into systemic circulation to achieve a rapid systemic effect, the ability to administer the agent continuously and/or in a large volume if desired, and less local tissue irritation than intramuscular or subcutaneous administration.

For intravenous administration, the aminobisphosphonate (e.g., neridronate), or a pharmaceutical composition comprising aminobisphosphonate (e.g., neridronate), may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In some embodiments, the pH of the final composition ranges from 2 to 8, or preferably from 4 to 7. Antioxidant excipients may include, for example, sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Antimicrobial agents may also be included to achieve a bacteriostatic or fungistatic solution, including but not limited to phenyl mercuric nitrate, thimerosal, benzethonium chloride, benzalkonium chloride, phenol, cresol, and chlorobutanol. In some embodiments, the aminobisphosphonate (e.g., neridronate (e.g., sodium neridronate)) is dissolved in sterile normal saline (0.9% NaCl, e.g., United States Pharmacopeia (USP) grade saline for injection).

In some embodiments, the aminobisphosphonate (e.g., neridronate), or a pharmaceutical composition comprising aminobisphosphonate (e.g., neridronate) for intravenous administration may be provided in the form of one more solids that are reconstituted with a suitable diluent such as sterile water, saline or dextrose in water shortly prior to administration. In some embodiments, the aminobisphosphonate (e.g., neridronate), or a pharmaceutical composition comprising the aminobisphosphonate (e.g., neridronate), is provided in solution ready to administer parenterally. In some embodiments, the aminobisphosphonate (e.g., neridronic acid), or a pharmaceutical composition comprising aminobisphosphonate (e.g., neridronic acid), or a pharmaceutically acceptable salt, solvate, polymorph, stereoisomer, or prodrug thereof, is provided in a solution that is further diluted prior to administration.

In some embodiments, one or more additional therapeutic agents may be administered in combination with the aminobisphosphonate (e.g., sodium neridronate). As used herein, an "additional therapeutic agent(s)" is intended to mean a pharmaceutically active agent(s) that is active in the body, including pro-drugs that convert to pharmaceutically active form after administration, which are different from the aminobisphosphonate compounds of the disclosure, and also includes pharmaceutically acceptable salts of the additional active agents. For example, the one or more additional therapeutic agents may comprise an analgesic (e.g., acetaminophen, oxycodone).

In embodiments that include administering a combination of aminobisphosphonate (e.g., neridronate) and additional therapeutic agent, the combination may be provided as a mixture.

In some embodiments, the aminobisphosphonate (e.g., neridronate), and an additional therapeutic agent may be mixed prior to administration or may be administered separately.

In some embodiments, the aminobisphosphonate (e.g., neridronate) may be administered in combination with a vitamin and/or a mineral. In some embodiments, the aminobisphosphonate (e.g., neridronate) may be administered in combination with vitamin D and/or calcium. It will be understood that vitamin D and calcium can be administered in any of their known forms as relevant.

Formulations for injection or infusion can be in the form of, e.g., solutions, suspensions or emulsions in oily or aqueous vehicles, and can contain excipients such as suspending agents, dispersing agents and/or stabilizing agents. For example, aqueous or non-aqueous (e.g., oily) sterile injection solutions can contain a compound of the disclosure, or a pharmaceutical composition comprising a compound of the disclosure, or a pharmaceutically acceptable salt, solvate, polymorph, stereoisomer, or prodrug thereof, along with excipients such as an antioxidant, a buffer, a bacteriostat and solutes that render the formulation isotonic with the blood of the subject. Aqueous or non-aqueous sterile suspensions can contain a compound of the disclosure, or a pharmaceutical composition comprising a compound of the disclosure, or a pharmaceutically acceptable salt, solvate, polymorph, stereoisomer, or prodrug thereof, along with excipients such as a suspending agent and a thickening agent, and optionally a stabilizer and an agent that increases the solubility of a compound of the disclosure, or a pharmaceutical composition comprising a compound of the disclosure, or a pharmaceutically acceptable salt, solvate, polymorph, stereoisomer, or prodrug thereof, to allow for the preparation of a more concentrated solution or suspension. As another example, a sterile aqueous solution for injection or infusion (e.g., subcutaneously or intravenously) can contain a compound of the disclosure, or a pharmaceutical composition comprising a compound of the disclosure, or a pharmaceutically acceptable salt, solvate, polymorph, stereoisomer, or prodrug thereof, along with NaCl, a buffering agent (e.g., sodium citrate), a preservative (e.g., meta-cresol), and optionally a base (e.g., NaOH) and/or an acid (e.g., HCl) to adjust pH.

The pharmaceutical compositions can be manufactured in any suitable manner known in the art, e.g., by means of conventional mixing, dissolving, suspending, granulating, dragee-making, levigating, emulsifying, encapsulating, entrapping or compressing processes.

A pharmaceutical composition can be presented in unit dosage form as a single dose wherein all active and inactive ingredients are combined in a suitable system, and components do not need to be mixed to form the composition to be administered. The unit dosage form can contain an effective dose, or an appropriate fraction thereof, of an active ingredient of the disclosure (e.g., aminobisphosphonate (e.g., neridronate)). Representative examples of a unit dosage form include a tablet, capsule or pill for oral administration, or a single use sterile vial or ampoule for intravenous administration.

In some embodiments, the active ingredient is administered under a dosing schedule in which a first dosage amount is administered, followed by one or more therapeutically effective subsequent dosage amounts. In some embodiments, a first dosage amount is larger (e.g., about 1.5, 2, 3, 4 or 5 or more times larger) than a subsequent dosage amount. In some embodiments, the first dosage amount is about 1.5 times, or about two times, or about three times, or about four times, or about five times greater than the subsequent dosage amount.

The therapeutically effective amount (e.g., the amount needed to achieve a positive therapeutic response), the frequency of administration of, and/or the duration of treatment with, an active ingredient of the disclosure (e.g., aminobisphosphonate (e.g., neridronate)) may vary based on various factors, including, but not limited to, the nature and severity of the disease and/or at least one symptom thereof, the subject to be treated, the general health of the subject, the age, weight, gender, and/or diet of the subject, route of administration, drug interaction(s), reaction sensitivities, and tolerance/response to therapy, all of which can be determined by one of ordinary skill in the art such as a medical professional. The dosage amount and/or duration may be adjusted by a medical professional, such as a physician or veterinarian, including in the event of any complication. Dosage amounts and/or duration can be adjusted to provide sufficient levels of the compounds of the disclosure or to maintain the desired effect. For example, the dosage amount may be increased or decreased. For example, the dosage amount of the aminobisphosphonate (e.g., neridronate) may be decreased for patients with decreased renal function.

The aminobisphosphonate (e.g., neridronate) may be administered alone or in the form of a composition (e.g., pharmaceutical composition or formulation). Pharmaceutical compositions may be conveniently presented as one or more unit dose forms containing a predetermined amount of an active agent per dose.

In some embodiments, a pharmaceutical composition comprises aminobisphosphonate (e.g., neridronate) and one or more pharmaceutically acceptable carriers or excipients. Pharmaceutically acceptable carriers and excipients include pharmaceutically acceptable materials, vehicles and substances, including for example any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included.

Non-limiting examples of excipients include liquid and solid fillers, diluents, binders, lubricants, glidants, solubilizers, surfactants, dispersing agents, disintegration agents, emulsifying agents, wetting agents, suspending agents, thickeners, solvents, isotonic agents, buffers, pH adjusters, stabilizers, preservatives, antioxidants, antimicrobial agents, antibacterial agents, antifungal agents, absorption-delaying agents, sweetening agents, flavoring agents, coloring agents, adjuvants, encapsulating materials and coating materials. For example, conventional vehicles and carriers include without limitation oils (e.g., vegetable oils, such as sesame oil), aqueous solvents (e.g., saline, phosphate-buffered saline [PBS] and isotonic solutions [e.g., Ringer's solution]), and solvents (e.g., dimethyl sulfoxide [DMSO] and alcohols [e.g., ethanol, glycerol and propylene glycol]). Except insofar as any conventional carrier or excipient is incompatible with the active ingredient, the disclosure encompasses the use of all conventional carriers and excipients in formulations containing a compound of the disclosure.

As will be appreciated by the ordinarily skilled artisan, a pharmaceutically acceptable excipient is any constituent which adapts the composition to a particular route of administration or aids the processing of a composition into a dosage form without itself exerting an active pharmaceutical effect. In general, compositions comprise more than one pharmaceutically acceptable excipient, and the pharmaceutically acceptable excipient(s) is selected based on the form of an oral dosage form. Examples of pharmaceutically acceptable excipients and methods of manufacture of oral dosage forms such as those mentioned above may be found in A. Gennaro (ed.), Remington: The Science and Practice of Pharmacy, 20th Edition, (2000), Lippincott Williams & Wilkins, Baltimore, MD.

Pharmaceutically acceptable excipients suitable for use in the present disclosure include, without limitation, carriers (such as lactose, starch, starch derivatives, talc, stearic acid or its salts for, e.g., pills, tablets, sugar-coated tablets and hard gelatin capsules; such as fats, waxes, semisolid and liquid polyols, natural or hardened oils, etc. for soft capsules; such as water, physiologically acceptable sodium chloride solution, alcohols, glycerol, polyols, sucrose, invert sugar, glucose, mannitol, vegetable oils, etc. for solutions, emulsions or syrups), fillers, disintegrants, binders, lubricants, pressing aids, wetting agents, stabilizers, emulsifiers, absorption enhancers, penetration enhancers, permeation enhancers, dispersants, preservatives, sweeteners, colorants, flavorings, aromatizers, thickeners, diluents, buffer substances, solvents, solubilizers, agents for achieving a depot effect, salts for altering the osmotic pressure, coating agents and/or antioxidants.

In some embodiments, a pharmaceutical composition can be presented as a kit, wherein the active ingredient, excipients and carriers (e.g., solvents) are provided in two or more separate containers (e.g., ampoules, vials, tubes, bottles or syringes) and need to be combined to form the composition to be administered. The kit can contain instructions for storing, preparing and administering the composition (e.g., a solution to be injected intravenously).

A kit can contain all active and inactive ingredients in unit dosage form or the active ingredient and inactive ingredients in two or more separate containers, and can contain instructions for using the pharmaceutical composition.

In an embodiment, the disclosure provides a method of selectively treating Complex Regional Pain Syndrome ("CRPS") Type 1 comprising: (A) identifying a patient that has been diagnosed as having CRPS Type 1 as a patient that is likely to have a positive therapeutic response to aminobisphosphonate treatment and selecting that patient to receive aminobisphosphonate treatment for CRPS Type 1 by confirming that the patient (i) has warm phase CRPS Type 1 and (ii) exhibits increased bone metabolic activity asymmetrically in the affected region; and (B) administering to the selected patient a therapeutically effective amount of an aminobisphosphonate. In an embodiment, the aminobisphosphonate is neridronate. In an embodiment, the neridronate is sodium neridronate. In an embodiment, the positive therapeutic response is a 20% or more reduction in pain intensity. In an embodiment, the positive therapeutic response is a 30% or more reduction in pain intensity. In an embodiment, the positive therapeutic response is a 50% or more reduction in pain intensity. In an embodiment, the positive therapeutic response is a 70% or more reduction in pain intensity. In an embodiment, the positive therapeutic response is a 90% or more reduction in pain intensity.

In an embodiment, the disclosure provides a method of selectively treating Complex Regional Pain Syndrome ("CRPS") Type 1 comprising: (A) identifying a patient that has been diagnosed as having CRPS Type 1 as a patient that is likely to have a positive therapeutic response to neridronate treatment and selecting that patient to receive neridronate treatment for CRPS Type 1 by confirming that the patient (i) has warm phase CRPS Type 1 and (ii) exhibits increased bone metabolic activity asymmetrically in the affected region; and (B) administering to the selected patient a therapeutically effective amount of neridronate. In an embodiment, the neridronate is sodium neridronate. In an embodiment, the positive therapeutic response is a 20% or more reduction in pain intensity. In an embodiment, the positive therapeutic response is a 30% or more reduction in pain intensity. In an embodiment, the positive therapeutic response is a 50% or more reduction in pain intensity. In an embodiment, the positive therapeutic response is a 70% or more reduction in pain intensity. In an embodiment, the positive therapeutic response is a 90% or more reduction in pain intensity.

In an embodiment, the disclosure provides a method of selectively treating Complex Regional Pain Syndrome ("CRPS") Type 1 comprising: (A) selecting a patient to receive aminobisphosphonate treatment by: (i) diagnosing the patient as having CRPS Type 1, and (ii) confirming that the patient (a) has warm phase CRPS Type 1 and (b) exhibits active bone phase in an affected limb; and (B) administering to the selected patient a therapeutically effective amount of an aminobisphosphonate. In an embodiment, the aminobisphosphonate is neridronate. In an embodiment, the neridronate is sodium neridronate. In an embodiment, the positive therapeutic response is a 20% or more reduction in pain intensity. In an embodiment, the positive therapeutic response is a 30% or more reduction in pain intensity. In an embodiment, the positive therapeutic response is a 50% or more reduction in pain intensity. In an embodiment, the positive therapeutic response is a 70% or more reduction in pain intensity. In an embodiment, the positive therapeutic response is a 90% or more reduction in pain intensity.

In an embodiment, the disclosure provides a method of selectively treating Complex Regional Pain Syndrome ("CRPS") Type 1 comprising: (A) identifying a patient that has been diagnosed as having CRPS Type 1 as a patient that is likely to have a positive therapeutic response to bisphosphonate treatment by confirming that the patient (i) has warm phase CRPS Type 1 and (ii) exhibits active bone phase in an affected limb; and (B) administering to the selected patient a therapeutically effective amount of neridronate, thereby achieving the positive therapeutic response.

In an embodiment, the disclosure provides a method of selectively treating Complex Regional Pain Syndrome ("CRPS") Type 1 comprising: administering a therapeutically effective amount of an aminobisphosphonate to a patient having CRPS Type 1, wherein the patient (a) has warm phase CRPS Type 1 and (b) exhibits active bone phase in an affected limb. In an embodiment, the aminobisphosphonate is neridronate. In an embodiment, the neridronate is sodium neridronate. In an embodiment, the positive therapeutic response is a 20% or more reduction in pain intensity. In an embodiment, the positive therapeutic response is a 30% or more reduction in pain intensity. In an embodiment, the positive therapeutic response is a 50% or more reduction in pain intensity. In an embodiment, the positive therapeutic response is a 70% or more reduction in pain intensity. In an embodiment, the positive therapeutic response is a 90% or more reduction in pain intensity.

In an embodiment, the disclosure provides a method of treating Complex Regional Pain Syndrome ("CRPS") Type 1 comprising: administering a therapeutically effective amount of an aminobisphosphonate to a patient in need thereof, wherein the patient (a) has warm phase CRPS Type 1 and (b) exhibits active bone phase in an affected limb. In an embodiment, the aminobisphosphonate is neridronate. In an embodiment, the neridronate is sodium neridronate. In an embodiment, the positive therapeutic response is a 20% or more reduction in pain intensity. In an embodiment, the positive therapeutic response is a 30% or more reduction in pain intensity. In an embodiment, the positive therapeutic response is a 50% or more reduction in pain intensity. In an embodiment, the positive therapeutic response is a 70% or more reduction in pain intensity. In an embodiment, the positive therapeutic response is a 90% or more reduction in pain intensity.

The following example is provided for the purpose of further illustration only and are not intended to be limitations on the disclosure.

EXAMPLES

Example 1

A Randomized, Triple-Blind, Placebo-Controlled, Phase 3 Trial to Evaluate the Efficacy, Safety, and Tolerability of Intravenous (IV) Neridronate for Treatment of Complex Regional Pain Syndrome (CRPS)-1

This is a multicenter, randomized, triple-blind, controlled trial, to assess the efficacy, safety, and tolerability of neridronate 400 mg IV in adult participants in the warm phase of CRPS Type 1 and a positive TPBS.

Eligible participants will be randomly assigned in a 1:1 ratio to receive neridronate, or matching placebo. A total dose of 400 mg neridronate will be administered as 4 IV infusions of 100 mg each on Days 1, 4, 7 and 10. Neridronate or matching placebo will be administered as a slow infusion (at least 2 hours). The dose will be adjusted as needed for participants with renal impairment.

Investigational product (IP) is supplied in glass vials, each containing 111.18 mg sodium neridronate hemihydrate (equivalent to 100 mg neridronate [12.5 mg/mL] neridronic acid hereafter known as neridronate) or matching placebo in a total volume of 8 mL.

The IP is supplied as a single-use sterile solution in a glass vial, each containing 111.2 mg sodium neridronate hemihydrate (equivalent to 100 mg neridronic acid) or matching placebo in a total volume of 8 mL. The IP will be aseptically compounded into an IV saline bag and infused by appropriately trained personnel in accordance with current United States Pharmacopeia (USP) <797> and appropriate institutional pharmacy standards. Instructions and additional details will be provided in the pharmacy manual.

For each infusion, the full contents of a single vial (8 mL) will be diluted in sterile, normal saline for injection (0.9% NaCl (sodium, chloride) USP grade in a volume of approximately 500 mL using a single-use IV bag.

For participants with moderately impaired renal function (<60 mL/min/1.73 $m^2$), the dose will be reduced to 62.5 mg at each of the 4 infusions for a total dose of 250 mg. For each infusion, 5 mL of solution from a single 8-mL vial (corresponding to neridronate 62.5 mg) will be diluted in 500 mL normal saline (sterile 0.9% NaCl, USP) and administered by slow IV infusion of at least 2 hours at each treatment visit, resulting in a total dose of 250 mg neridronate or matching placebo. If required, dose modifications will be based on the eGFR values prior to each IP infusion. Dose modification must be recorded in the participant's source document and eCRF.

This dose adjustment is based on a Phase 1 renal impairment study (HP7013-02; N=24) demonstrating an increase of 70% in AUC infinity in the moderate renal impaired function group compared with the normal renal function group. There were no meaningful differences in $C_{max}$. For additional details please refer to the IB.

The IP should not be diluted in solutions containing calcium and should not be infused in combination with any other medication. The time and volume of IP transferred to the infusion bag must be recorded in the participant's source documentation and eCRF.

The IP must be stored in a secure room with restricted access. IP should be maintained at room temperature, under controlled conditions, with the temperature monitored, according to the storage requirement specified in the label. The IP must not be frozen or refrigerated. Temperature must not go under 15° C. and must not exceed 30° C.

Controls will be implemented at the trial site to ensure documented compliance with these requirements.

The primary efficacy endpoint is change from baseline to Week 12 in pain intensity using the 7-day average of twice daily "pain now" scores on the 11-point numeric rating scale (NRS). A further list of trial objections and end points is provided in Table 2 below.

The total planned trial duration for each participant will be approximately up to 18 weeks and will include a screening period of up to 6 weeks to confirm eligibility including TPBS, a treatment period on Days 1, 4, 7, and 10, where participants will be infused with 100 mg IV neridronate for a total dose of 400 mg or matching placebo, and a post treatment follow-up period where participants will be evaluated at the sites for efficacy and safety on Weeks 3, 6, and 12.

Approximately 270 consenting adult participants meeting all eligibility criteria will be randomized. Randomization will be stratified by moderate (<7) vs. severe (≥7) pain (11-point NRS) at the Randomization Visit. Within each stratum, participants will be randomly allocated to receive either neridronate or matching placebo in a 1:1 ratio.

Diagnosis of CRPS according to the clinical diagnostic criteria in IASP ("Budapest clinical criteria"—Table 3 below) must be documented at the Screening and Randomization Visit upon examination of the participant. Evidence of asymmetrical signs and symptoms, relative to the contralateral (unaffected) limb, is a requirement for fulfilling the diagnostic criteria. A precise location of the CRPS, consistent with the location of signs and symptoms, must be documented.

Specific to this trial, beyond the clinical Budapest criteria other key limitations in enrollment include:

Only participants with CRPS Type 1 are eligible. As such, documentation that the inciting event did not involve damage to a peripheral nerve (e.g., through crush, stretch, laceration, severing) must be recorded in the participant's source documentation and eCRF.

Participants without a known inciting event are not eligible for this trial. The known inciting event (e.g., sprain, fracture, surgery, contusion) must be documented in the participant's source documentation and eCRF with its timing.

Participants with more than one limb affected by CRPS are not eligible for this trial.

Diagnosis of CRPS involving an atypical body part (e.g., trunk, breasts, pelvic region, lower back, face, shoulder, or hip) is not permitted in this trial; only hand, arm, foot or leg involvement is allowed.

The PCS (See Appendix 3 below) is a 13-item self-report measure designed to assess the extent to which individuals bring a "negative mental set" to their pain experience and comprises 3 subdomains related to rumination, magnification, and helplessness. Items are scored on a 0 to 4 scale ranging from "not at all" to "all the time" with the total score ranging from 0 to 52. Participants with a total score of 40 or greater are above the 92nd percentile of clinic samples of chronic pain participants and will not be eligible for the trial.

Contraindications to IV bisphosphonates and neridronate include hypersensitivity to the active substance or to any of the excipients or to other medicinal products in the bisphosphonates group: severely impaired renal function, pregnancy and lactation. Given known and potential risks of neridronate, candidates with severely impaired renal function, risk factors for QT prolongation, and pregnant or lactating women are excluded from the trial. Women of childbearing potential (WOCBP) will be advised that pregnancy should be avoided for 6 months after the cessation of treatment. Participants will be monitored with ECGs, assessment of renal function, and other laboratory parameters with IP paused or stopped based on stopping rules.

Bisphosphonates, including neridronate, can cause hypocalcemia. As such, all participants must have adequate vitamin D and calcium levels before neridronate treatment is started. In addition, participants will take calcium and vitamin D supplement, starting from the Screening Visit (Visit 1) and continuing through to the end of trial (EOT) to prophylactically prevent the development of hypocalcemia with neridronate treatment. Participants will be monitored for calcium levels with IP paused or stopped based on stopping rules.

To minimize risk to potential participants who may be less likely to benefit from neridronate therapy, other eligibility criteria are aimed at including only a subtype of CRPS Type 1 participants who are most likely to benefit from treatment (i.e., positive TPBS; warm stage).

Triple phase bone scan (TPBS) is a nuclear medicine (scintigraphy) study that makes use of IV injected technetium-99m bound to a bisphosphonate (commonly Tc99mmethylene diphosphonate [MDP]) as the active agent. About 50% of the injected dose will be absorbed by the bones after 2 to 6 hours. Participants should be well hydrated. The entire procedure will take approximately 4-6 hours.

The TPBS imaging has 3 phases that follow the IV tracer injection:

Phase 1 Flow: 2-5 second gamma images are obtained for 60 seconds to demonstrate perfusion.

Phase 2 Blood Pool: Obtained 5 minutes after injection to demonstrate blood pool in soft tissue (balance between plasma and interstitium).

Phase 3 Bone: Obtained 2-4 hours later, after urinary extraction has decreased the amount of radionuclide in soft tissue.

For purposes of this trial, phase 3 (bone) should be conducted at 3 hours±30 min. Only the CRPS regional area bilaterally needs to be scanned. This is a much shorter procedure, typically 5-10 minutes, as opposed to the ~30 min needed for the routine procedure of full body scan.

A distinct asymmetry in phase 2 (blood pool) and/or 3 (bone) between the CRPS region and the contralateral region is required for eligibility. A previous scan within 3 months prior to Randomization visit is acceptable, if available and of sufficient quality for central read. Scans will be performed in equipment meeting the American College of Radiology (ACR) standards. Scans will be read locally and may be read centrally to confirm eligibility (e.g., in case the local radiologist report is ambiguous or unclear). All scans will be uploaded to central storage and may be read centrally for other quantitative and qualitative assessments. Results of each of the 3 phases will be documented in the participant's source documentation and eCRF.

TABLE 2

Trial Objectives and Endpoints

| Trial Objectives | Trial Endpoints |
|---|---|
| Primary Objective: | Primary Endpoint: |
| To evaluate the efficacy of neridronate 400 mg compared to placebo based on pain intensity | Change from baseline to Week 12 in pain intensity using the 7-day average of twice-daily "pain now" assessments on the 11-point NRS |
| Secondary Efficacy Objective: | Secondary Endpoints: |
| To further evaluate the efficacy of neridronate 400 mg compared to placebo based on pain intensity as well as other measures of treatment effect | Key secondary endpoints:<br>1. At least a 50% reduction from baseline to Week 12 in pain intensity using the 7-day average of twice-daily "pain now" assessments on the 11-point NRS<br>2. Change from baseline to Week 12 in CRPS Severity Score (CSS)<br>3. Patient Global Impression of Change (PGI-C) in CRPS-Related Health at Week 12<br>4. Change from baseline to Week 12 in the Short Form Health Survey (SF-36) Physical Functioning domain<br>Supportive secondary endpoints:<br>Change from baseline to Weeks 1-11 in pain intensity using 7-day averages of twice-daily "pain now" assessments on the 11-point NRS<br>At least a 50% reduction from baseline to Weeks 1-11 in pain intensity using the 7-day average of twice-daily "pain now" assessments on the 11-point NRS.<br>At least a 30%, 70%, and 90% reduction from baseline to Weeks 1-12 in pain intensity using the 7-day average of twice-daily "pain now" assessments on the 11-point NRS.<br>Time to onset of analgesic improvement, defined as at least a 30% reduction from baseline in pain intensity using the 7-day average of twice-daily "pain now" assessments |

TABLE 2-continued

| | |
|---|---|
| | on the 11-point NRS that is maintained for at least 1 week.<br>Change from baseline to Weeks 1-12 in the 7 -day average of the twice -daily "worst pain" assessments (over a half-day recall period) on the 11-point NRS.<br>At least a 30%, 50%, 70% and 90% reduction from baseline to Weeks 1-12 in pain intensity using the 7-day average of twice-daily "worst pain" assessments (over a half-day recall period) on the 11-point NRS.<br>Change from baseline to Weeks 3, 6, and 12 in pain evoked by active motion on the 11-point NRS.<br>At least a 50% reduction from baseline to Weeks 3, 6, and 12 in pain evoked by active motion on the 11-point NRS.<br>Change from baseline to Weeks 3, 6, and 12 in active range of motion (AROM) (measured by goniometry) of affected limb vs. contralateral limb.<br>Change from baseline to Weeks 3 and 6 in the CSS and to Weeks 3, 6, and 12 in the individual elements of the CSS.<br>Change from baseline to Weeks 3, 6, and 12 in edema of affected limb on a 0 (none) to 3 (severe) scale.<br>Change from baseline to Weeks 3, 6, and 12 in temperature (° C.) of affected limb vs contralateral limb.<br>Use of rescue analgesic medications (acetaminophen, oxycodone, both) during the 7 days prior to Weeks 1-12.<br>Mean dose of rescue analgesic medicines (acetaminophen, oxycodone) during the 7 days prior to weeks 1-12.<br>Heavy use of rescue analgesic medications (acetaminophen, oxycodone, both) defined as > 3 g acetaminophen > 3 days/week and/or ≥ 15 mg oxycodone > 3 days/week, during the 7 days prior to Weeks 1-12.<br>PGI-C in CRPS-related health at Weeks 3 and 6.<br>Clinician Global Impression of Change (CGI-C) in CRPS-related health at Weeks 3, 6, and 12.<br>Patient Global Impression of Severity (PGI-S) in CRPS Severity at Weeks 3, 6, and 12.<br>Change from baseline to Weeks 3, 6, and 12 in Short-Form McGill Pain Questionnaire 2 (SF-MPQ-2) (a) Total Pain Score, (b) each of 4 domain scores, (c) single items.<br>Moderate (at least 30%) and substantial (at least 50%) improvement from baseline to Weeks 3, 6, and 12 in SF-MPQ-2 (a) Total Pain Score, and (b) each of 4 domain scores.<br>Change from baseline to Weeks 3, 6, and 12 in the 36-item SF-36 (a) 8 domain scores and (b) 2 component summary scores, excluding the Week 12 Physical Functioning domain (as captured as fourth key secondary endpoint).<br>Moderate (≥30%) and substantial (≥50%) improvement from baseline to Weeks 3, 6, and 12 in the SF-36 (a) 8 domain scores and (b) 2 component summary scores.<br>Change from baseline to Weeks 1-12 in the 7-day average of the Daily Sleep Interference Scale (DSIS) assessment on the 11-point NRS.<br>Moderate (≥30%) and substantial (≥50%) improvement from baseline to Weeks 1-12 in the DSIS assessment on the 11-point NRS. |

TABLE 2-continued

| | |
|---|---|
| | Time to moderate (≥30%) and substantial (≥50%) reduction from baseline in the 7-day average of the DSIS assessment on the 11-point NRS. |
| Exploratory Efficacy Objective | Exploratory Endpoints |
| To explore the efficacy of neridronate 400 mg compared to placebo based on photography, TPBS, and biomarkers. | Photography (data permitting).<br>Potential characterization of TPBS (phase, quantification).<br>High sensitivity C-reactive protein (hsCRP); complete blood count (CBC); and future biomarkers yet to be determined. |
| Safety Objectives: | Safety Endpoints: |
| To evaluate the safety and tolerability of neridronate 400 mg compared to placebo. | Incidence, seriousness, severity, and relatedness to IP of treatment emergent adverse events (TEAEs).<br>Incidence of TEAEs leading to early discontinuation of treatment (tolerability).<br>Observed values and changes from baseline in physical exams, vital signs, laboratory parameters, and cardiac monitoring parameters (12-lead electrocardiogram [ECG]). |
| To characterize acute phase reactions (APR). | Incidence, severity and time course of post infusion reactions (also known as APR). |
| To evaluate the risk of IV neridronate 400 mg infused over at least 2 hours on QT prolongation. | By-time analysis of neridronate pharmacokinetics (PK) plasma concentrations and associated Fredericia-corrected QT interval (QTcF) prolongation parameters evaluated within 30 minutes prior to each infusion and within 30 minutes after each infusion on Days 1, 4, 7, and 10. |
| Other Objectives | Endpoint |
| Characterization of population with and without positive TPBS. | Demographics.<br>Baseline CRPS-1 disease characteristics |

TABLE 2-continued

| |
|---|
| Further exploratory endpoints may be added and will be described in the finalized statistical analysis plan (SAP) prior to database lock. |
| Key Eligibility Criteria |
| Key inclusion criteria:<br>Adult participants diagnosed with CRPS-1 based on Clinical Budapest Criteria;<br>≤6 months from CRPS symptom onset at the Randomization Visit;<br>Positive TPBS (within 3 months of Randomization Visit);<br>Warm CRPS-1 subtype defined as:<br>Edema in the affected limb;<br>AND ≥ 2 of the following:<br>Obvious redness in the affected region relative to the same region on the contralateral limb on inspection<br>≥1° C. increase in temperature on the affected limb relative to the contralateral limb<br>Moderate-severe edema in the affected limb (score of 2 or 3 on the 0-3 edema scale)<br>Pain > 4 on the 11-point NRS as an average of "pain now" intensity using a 7-day twice-daily diary during the week before Randomization Visit.<br>Pain intensity > 4 on the 11-point NRS based on the 7-day average of twice-daily "pain now" assessments during the week before Randomization Visit and pain is not substantially improving, defined as less than a 30% improvement in 7-day average pain intensity from the first week of screening to the last week of screening. |
| Statistical Methods |
| The SAP will be developed and finalized prior to database lock and will describe in detail the statistical analysis methodology.<br>Sample Size:<br>Approximately 270 (135 neridronate, 135 placebo) participants will be randomized.<br>Assuming a medium-to-large effect size of 0.65, the trial will have > 90% power to reject the primary estimand null hypothesis. Assuming large effect sizes for key secondary endpoints 1-3 of 0.73, 0.75, and 1.57, respectively, and a small-to-medium effect size of 0.35 for the fourth key secondary endpoint, the trial will have > 80% power to reject the primary and all key secondary estimand null hypotheses. |

TABLE 3

Schedule of Assessments

| Trial Visit Assessments[2] | Screening[1] Visit 1 Day-42 Day-1 | Treatment Visit 2 Day 1 Randomization | Treatment Visit 3 Day 4 | Treatment Visit 4 Day 7 | Treatment Visit 5 Day 10 | Post-Treatment Follow-up Phase Visit 6 Day 13 | Visit 7 Week 3 | Visit 8 Week 6 | Visit 9 Week 9 | Visit 10 Week 12 EOT/ET |
|---|---|---|---|---|---|---|---|---|---|---|
| Visit type | IC | IC | IC | IC | IC | PC | IC | IC | PC | IC |
| Window | | | +1 day | +1 day | +1 day | +2 day | +4 days | +4 days | +4 days | +4 days |
| Informed Consent[1] | X | | | | | | | | | |
| Demographics | X | | | | | | | | | |
| Medical History including CRPS History[3] | X | X | | | | | | | | |
| Prior/Concomitant Medications[4] | X | X | X | X | X | X | X | X | X | X |
| Inclusion/Exclusion Criteria | X | X | | | | | | | | |
| Vital Signs[5] | X | X | X | X | X | | X | X | | X |
| 12-lead ECG[6] | X | X | X | X | X | | | | | X |

TABLE 3-continued

Schedule of Assessments

| Trial Visit Assessments[2] | Screen-ing[1] Visit 1 Day-42 Day-1 | Treatment: Visit 2 Day 1 Random-ization | Treatment: Visit 3 Day 4 | Treatment: Visit 4 Day 7 | Treatment: Visit 5 Day 10 | Post-Treatment Follow-up Phase: Visit 6 Day 13 | Post-Treatment Follow-up Phase: Visit 7 Week 3 | Post-Treatment Follow-up Phase: Visit 8 Week 6 | Post-Treatment Follow-up Phase: Visit 9 Week 9 | Post-Treatment Follow-up Phase: Visit 10 Week 12 EOT/ET |
|---|---|---|---|---|---|---|---|---|---|---|
| Physical Exam[7] | X | X | X* | X* | X | | X | X | | X |
| CRPS Assessments: | | | | | | | | | | |
| AROM8 | X | X | | | X | | X | X | | X |
| CSS | X | X | X | X | X | | X | X | | X |
| $Ca^{++}$ and Creatinine for pre-infusion eGFR evaluation[9] | | | X[9] | X[9] | X[9] | | | | | |
| WBC with differential, PK[10] | | X | X | X | X | | | | | |
| hsCRP | | X | X | X | X | | X | X | | X |
| Laboratory Tests[11] | X | X | | | X | | X | X | | X |
| Pregnancy test/FSH[12] | X | X | X | X | X | | | | | X |
| Alcohol and Drug screen[13] | X | X | | | | | | | | |
| Visit type | IC | IC | IC | IC | IC | PC | IC | IC | PC | IC |
| Blood, plasma, biomarker collection | | X | | | X | | | | | X |
| Participant training[14] | X | X | | ⟶ | ⟶ | ⟶ | ⟶ | ⟶ | ⟶ | |
| PROs: | | | | | | | | | | |
| PCS | X | | | | | | | | | |
| PGI-S | X | X | X | X | X | | X | X | | X |
| SF-MPQ-2 | X | X | X | X | X | | X | X | | X |
| SF-36v2 | | X | | | X | | X | X | | X |
| PGI-C | | | X | X | X | | X | X | | X |
| Clinician assessment: CGI-C | | | X | X | X | | X | X | | X |
| eDiary[15] | X | | ⟶ | ⟶ | ⟶ | ⟶ | ⟶ | ⟶ | | |
| TPBS[16] | X | | | | | | | | | |
| Photography[17] | | X | | | X | | | X | | X |
| AE/SAE collection and review[18] | X | | ⟶ | ⟶ | ⟶ | ⟶ | ⟶ | ⟶ | | |
| Randomization | | X | | | | | | | | |
| Prophylactic oral acetaminophen[19] | | X | | | | | | | | |
| Supplementation/ Rescue dispensing and accountability[20] | X | X | X | X | X | | X | X | | X[$] |
| IV infusion[21] | | X | X | X | X | | | | | |

Abbreviations:
AE = adverse event;
APR = acute phase reaction;
AROM = active range ofmotion;
Arrow = continuous activity in between and during visits;
$Ca^{++}$ = calcium;
CGI-C = Clinician Global Improvement of Change;
CRPS = complex regional pain syndrome;
CSS = CRPS Severity Score;
DSIS = daily sleep interference scale;
ECG = electrocardiogram;
eDiary = electronic diary;
eGFR = estimated glomerular filtration rate;
EOT = end of trial;
ET = early termination;
FSH = follicle-stimulating hormone;

TABLE 3-continued

Schedule of Assessments

| Trial Visit Assessments[2] | Screening[1] Visit 1 Day-42 Day-1 | Treatment Visit 2 Day 1 Randomization | Treatment Visit 3 Day 4 | Treatment Visit 4 Day 7 | Treatment Visit 5 Day 10 | Post-Treatment Follow-up Phase Visit 6 Day 13 | Post-Treatment Follow-up Phase Visit 7 Week 3 | Post-Treatment Follow-up Phase Visit 8 Week 6 | Post-Treatment Follow-up Phase Visit 9 Week 9 | Post-Treatment Follow-up Phase Visit 10 Week 12 EOT/ET |
|---|---|---|---|---|---|---|---|---|---|---|

IC = in clinic;
IP = investigational product;
IV = intravenous;
NRS = numerical rating scale;
OTC = over the counter;
PC = phone call;
PCS = Pain Catastrophizing Scale;
PGI-C = Patient Global Impression of Change;
PGI-S = Patient Global Impression of Severity;
PK = pharmacokinetics;
PRN = as needed;
PRO = patient reported outcome;
PTH = parathyroidhormone;
ROM = range of motion;
SAE = serious adverse event;
SF- MPQ-2 = Short Form McGill Pain Questionnaire 2;
SF-36v2 = Short Form 36-Item Health Survey Version 2;
TPBS = triple phase bone scan;
WBC= white blood cells;
WOCBP = women of child bearing potential.

[1]Informed consent must be obtained prior to any trial related activities.

[2]During visits the following order of assessments will be maintained, when possible: scheduled PROs should be filled out prior to any site assessments; laboratory sampling should be taken with sufficient interval so as to not impact vital signs and ECGs.

[3]Medical History includes all prior and concomitant medical conditions (including psychiatric history), prior surgeries and procedures, smoking history (never, past smoker, and current smoker; years smoked and daily packs), dental history (date of last dental visit, reason for visit, any of the following history in the 3 months prior to the Screening and/or Randomization Visits: dental extractions, invasive dental or jaw surgeries, dental or periodontal disease, gum injury due to dentures or other reasons, and dental history that may predispose to risk of medication related osteonecrosis of the jaw, including planned procedures), CRPS history (inciting event (type, date, treatment), date of symptom onset, date of diagnosis, diagnostic tests (including those done to rule out other diagnoses, e.g .; imaging modality, date, and results; procedure(s) type, date, and results), location of CRPS, prior CRPS, and family history of CRPS). Additional medical history that may be considered relevant should also be documented.

[4]Any medication (including OTC or prescription medicines, recreational drugs, vitamins, and/or herbal supplements), vaccines, procedures, treatment modalities (e.g., physiotherapy, psychological therapy, biofeedback) or other specific categories of interest that the participant received at any time for CRPS and within 3 months before Screening for any other condition should be recorded. During subsequent visits, participants should be asked about their use of alcohol, any recreational or illegal substance use, OTC, prescribed drugs, medication usage, and treatment modalities.

[5]Vital signs include systolic and diastolic blood pressure, heart rate, respiratory rate, and temperature. Vital signs will be measured at every clinic visit in a semi-supine position after > 5 minutes rest without distraction. On days of infusion, vital signs will be collected prior to dosing, twice during the first hour of infusion, once thereafter, or more frequently as required per clinical judgment, as well as for symptoms associated with APR, and immediately following each infusion.

[6]Triplicate 12-lead ECGs will be performed at all indicated visits. On Days 1, 4, 7, and 10, triplicate ECGs will be collected immediately prior to the PK assessments within 30 minutes prior to each infusion, and immediately prior to the PK assessments within 30 min after the completion of each infusion.

[7/*]A complete physical examination should include, at a minimum, assessments of alertness and orientation, general appearance, skin, head, eyes (including presence of ocular inflammation on examination such as redness, and sensitivity to light), ears, nose, mouth exam (for any unhealed or infected tooth extraction, significant dental/periodontal disease that may predispose for a need for tooth extraction or other invasive dental procedures, gum trauma, and overall dental hygiene), throat, chest, lungs, heart, abdomen, kidney, liver, lymphatics, musculoskeletal, and neurological systems. Hydration should be evaluated in particular prior to each IP infusion. Breast and genitourinary examinations are not required. Symptom-directed physical exams based on unsolicited symptomatology collected as part of participant's AE reporting and solicited APR AE reporting to be performed on Day 4 and 7 Visits (marked with * in the table), as necessary.

[8]AROM will be assessed followed by an assessment of pain with ROM (Appendix 11)

[9]Pre-infusion Ca and creatinine for eGFR evaluation on Days 4, 7, and 10, must be collected, preferably on the day of infusion. If not logistically feasible to obtain results on infusion day(s), these may be obtained within 36 hours prior to infusion. Results must be reviewed prior to infusion.

[10]WBC with differential will be obtained prior to each infusion and sent to the central lab. PK samples will be collected within 30 min prior to each of the 4 IP infusions and within 30 min after the completion of each of the four IP infusions and sent to central lab.

[11]Laboratory (Appendix 14) to be collected at specified time points. PTH, urine sample for albumin to creatinine ratio, serum pregnancy test for WOCBP, and FSH to confirm menopause, will only be collected at Screening Visit

[12]Negative serum pregnancy test at Screening for WOCBP. Negative urine pregnancy dipstick must be confirmed for WOCBP participants prior to each infusion. Female participants with ≥12 months of amenorrhea in the absence of other biological or physiological causes must have a serum FSH level >40 mIU/mL to confirm menopause at the Screening Visit. Otherwise, they must use contraception as described in Appendix 12

[13]Urine toxicology screen dipstick will be collected at Screening and Randomization Visits.

[14]Participant training on the eDiary, placebo response, importance of consistent and accurate response to eDiary and PROs, will occur at Screening with a refresher prior to infusion at Randomization Visit. Participants should be encouraged to contact the site with any questions regarding the conduct of the trial, eDiary, or to report AE, seek guidance on rescue medications, any new prescribed or OTC medication being contemplated. Training on any component of the trial may be repeated to ensure participant understanding and compliance throughout the trial.

[15]Collection of a twice-daily (morning and evening) NRS of "pain now", worst pain, rescue medication (type, dose, time), whether physical assistance was required to fill out the eDiary, and impact of pain on sleep by using the DSIS (morning only). Compliance with the eDiary will be reviewed at the Randomization Visit (prior to randomization); Participants who fall below 10 of 14 entries for "pain now" in the 7 days leading up to Randomization Visit will be considered screen failures. During the trial, participants who miss 2 consecutive days of eDiary entry will be contacted and reminded of the importance of daily completion.

[16]A TPBS will be performed as part of the Screening assessments prior to Randomization Visit. A previous scan within 3 months prior to Randomization Visit is acceptable, if available and of sufficient quality for central read.

[17]Up to 10 sites will be asked to participate in exploratory central photography. Anonymized photography of affected limb and contralateral limb per the photography manual should only be collected for participants who consent to photography.

[18]AE reporting will start at the time of consent. An AE occurring from the initiation of first dose will be considered as a TEAE. Assessment of APR should be conducted at Visits 2, 3, 4, 5, and 6.

[19]Participants will be prophylactically treated with acetaminophen 500 mg 1 hour prior to the first infusion (as APR is mostly associated with first infusion and absent or significantly reduced in subsequent infusions) and PRN thereafter for APR signs and symptoms. Note the total amount of acetaminophen for pain treatment, rescue medication, and APR treatment must not exceed 4 gram/day.

[20/$]Vitamin D, Calcium, and rescue medication will be dispensed per pharmacy manual. Accountability, by counting pills and documenting the reason for any discrepancy, will occur at every visit following Screening. Only accountability with no dispensation will occur at the EOT/ ET Visit (marked with $).

[21]IP will be administered on Days 1, 4, 7, and 10 as a slow infusion, (at least 2 hours). A window for the administration of IP is allowed, however the infusions should be a minimum of 48 hours apart.

Inclusion Criteria

Participants must satisfy ALL of the following criteria at Screening and before randomization.

1. Participants must be capable of understanding the trial requirements and be willing to provide informed consent prior to any trial-related procedures.
2. Participants must be willing and able to comply with all scheduled visits, treatment plan, laboratory tests, eDiary completion, participant questionnaires and other trial procedures. Participants must be able to differentiate and communicate with regard to location and intensity of pain. Physical assistance in filling out questionnaires is permitted only if required due to physical impairment.
3. Male or female participant≥18 years of age at time of Screening.
4. A diagnosis of CRPS-1 according to the clinical Budapest Criteria as recommended by the International Association for the Study of Pain (IASP), as well as no known peripheral nerve injury. Signs and symptoms of CRPS must apply to a single identified affected limb (i.e., arm, hand, wrist, leg, ankle or foot) and must demonstrate asymmetry with respect to the contralateral limb.
5. Single affected limb at the Screening and Randomization Visits meeting the following warm subtype criteria:
   a. Edema in the affected limb
      0-3 scale (0 [none] defined as no visible edema; 1 [mild] defined as visible edema but bony landmarks are clearly visible; 2 [moderate] defined as visible edema but bony landmarks are obscured; and 3 [severe] defined as very severe edema without visible bony landmarks and/or with notable skin tightness).
   b. AND ≥2 of the following:
      1) Obvious redness in the affected region relative to the same region on the contralateral limb on inspection
      2) ≥1° C. increase in temperature on the affected limb relative to the contralateral limb (See Appendix 2)
      3) Moderate-to-severe edema (score of 2 or 3 on the 0-3 edema scale)
6. An interval of ≤6 months since the onset of CRPS symptoms at the Randomization Visit.
7. A positive reading by a local radiologist or, if required, by a central reader, demonstrates increased uptake in the involved limb compared to the contralateral limb on TPBS (phase 2 and/or phase 3) during Screening. A historic scan not older than 3 months prior to Randomization visit is acceptable, if available and of sufficient quality for a central read.
8. An average of twice-daily "pain now" assessments of >4 on the 11-point NRS in the CRPS affected limb over the 7 days prior to Randomization as captured in the twice daily eDiary and pain is not substantially improving, defined as less than a 30% improvement in 7-day average pain intensity from the first week of screening to the last week of screening.
9. Adequate compliance with the eDiary in the 7 days prior to the Randomization Visit, defined as completion of at least 10 of the 14 entries for the measurement of "pain now"
10. Participant must have adequate venous access to enable blood sampling and 4 IV infusions.
11. Women of childbearing potential (WOCBP) must:
    a. Be nonpregnant as determined by a negative serum pregnancy test at Screening and negative highly sensitive urine pregnancy test on every visit before IP administration.
    b. Be nonlactating.
    c. Agree to use a highly effective method of contraception from at least 28 days prior to Randomization Visit for oral contraception (or at least 1 week longer than specified by the manufacturer for other contraceptives) and for at least 6 months following last IP administration.
    Exception: Women exclusively engaging in same-sex sexual activities are not required to meet this criterion.
    d. Willing to forego ova (egg) donation for at least the duration of the trial (Week 12 Visit)
12. Women of non-childbearing potential are defined as meeting at least 1 of the following criteria:
    a. Postmenopausal for at least 12 months without an alternative medical cause and has a follicle-stimulating hormone (FSH)>40 mIU/mL.
    b. Surgically sterile, defined as having a documented hysterectomy or bilateral oophorectomy or bilateral salpingectomy.

Exclusion Criteria

Participants who meet ANY of the following criteria during the Screening or Randomization Visit (as applicable) will be excluded.

1. A current or prior diagnosis of CRPS-2 or CRPS not otherwise specified (CRPS NOS), or whose CRPS has no known inciting event, or CRPS-1 without criteria of the warm subtype at the time of Screening.

≥40 points on the Pain Catastrophizing Scale (PCS-Signs of CRPS will be assessed by the Investigator and symptoms by the participant using the same methodology for both the Budapest clinical diagnostic criteria and the CRPS severity score, although different calculations are used to derive the criteria and the scale.

Please note that the following contains more details than are part of the criteria or scale; these details provide information on CRPS-related signs and symptoms for other elements of the trial.

The following assessments should be completed:

| Criteria | Yes/ No | Details of the finding on the affected side (unless otherwise specified), if criterion marked as "yes" |
|---|---|---|
| SYMPTOMS (as reported by or elicited from participants, in the past 48 hours) | | |
| 1. The pain is disproportionate to or continues longer than expected based on the clinician's experience as to what is usual and customary in this type of injury/lesion. | | NA |

-continued

| Criteria | Yes/ No | Details of the finding on the affected side (unless otherwise specified), if criterion marked as "yes" |
|---|---|---|
| 2a. Allodynia: a usually innocuous stimuli is now perceived as painful. | | NA |
| 2b. Hyperalgesia: Increased pain from a stimulus that normally provokes pain. The stimulus leads to a "great increase in the expected response". The participant reports that normally painful stimuli (e.g., stubbing the toe, hot bath water etc.) is now intensely painful and/or hurts for a prolonged time. | | NA |
| 3. Temperature asymmetry that is obvious to the participant. | | Affected side:<br>Warmer: Y/N<br>Colder: Y/N |
| 4. Color asymmetry that is obvious to the participant. | | Red: Y/N<br>Blue: Y/N<br>Pale: Y/N<br>Mottled: Y/N |
| 5. Sweating asymmetry that is obvious to the participant. | | NA |
| 6. Edema that is obvious to the participant (may be described as swelling). | | NA |
| 7. Dystrophic changes of nails, hair, or skin as described by the participant. | | Nails: Y/N<br>Hair: Y/N<br>Skin: Y/N |
| 8. Motor abnormalities such as weakness, tremor, dystonia (limb locked in unusual position) or myoclonus as described by the participant. Decreased range of motion as described by the participant. | | Weakness: Y/N<br>Dystonia: Y/N<br>Myoclonus: Y/N<br>Decreased ROM: Y/N |
| SIGNS (as observed by examiner on the exam date) | | |
| 9. Hyperalgesia: as tested by a single pinprick on the affected side (in center of most affected region) and same site of the contralateral limb using a new safety pin. Hyperalgesia is defined as increased pain from a stimulus that normally provokes pain. The stimulus leads to a great increase in the expected response. | | N/A |
| 10. Allodynia: reflects normally innocuous stimuli now being interpreted as painful. If any one of the following is positive on the affected side, it is not essential to complete all 4 of the following assessments:<br>to light touch as tested by light manual touch (or brush);<br>to deep joint pressure assessed by "firm" manual pressure to joint;<br>to vibration as assessed by 128 Hz tuning fork over bony prominence in affected limb;<br>to temperature as assessed by the blade of a tuning fork cooled under cold water (or cool water in a test tube) and heated under warm water (or warm water in a test tube). | | N/A |
| 11. Temperature asymmetry:* in the affected area compared to the comparable area on the contralateral limb.<br>Temperature of the affected and unaffected limbs will be measured using a digital infrared thermometer. Measurements across slightly different areas of the affected region and contralateral side may be required in order to identify the region with largest difference. Record the temperature at the warmest or coldest spot on the affected side and in a similar location on the contralateral side. | N/A | Temperature R side:<br>Temperature L side: |
| 12. Skin Color asymmetry: note region affected (i.e. hand, foot, knee or larger region). Please specify the color of the affected side as being red, blue, or pale, as well as being mottled or having a scar. This should be coded even if color difference is solely related to edema or scar tissue. If scar tissue is present and affecting the color of the area (as in a burn), please note. | | Red: Y/N<br>Blue: Y/N<br>Pale: Y/N<br>Mottled: Y/N<br>Scar presented and affecting color: Y/N |
| 13. Asymmetric edema: Rate edema on a scale of 0 (none); 1 (mild); 2 (moderate); 3 (severe) on the affected limb at the CRPS location where 0 (none) is defined as no visible edema; 1 (mild) is defined as visible edema but bony landmarks are clearly visible; 2 (moderate) is visible edema but bony landmarks are obscured and 3 (severe) defined as very severe edema without visible bony landmarks and/or with notable skin tightness. | | Affected limb edema:<br>R/L<br>0, 1, 2, 3 |

-continued

| Criteria | Yes/ No | Details of the finding on the affected side (unless otherwise specified), if criterion marked as "yes" |
|---|---|---|
| 14. Sweating asymmetry: If not obvious, this may be checked by running a smooth handled instrument (e.g., blade of turning fork) over the skin and noting if the instrument slides more easily on one side than the other, or by rate/degree of soaking (weight) of a facial tissue/sock etc., whatever is needed so that the categorical "yes/no" response may be marked. | | N/A |
| 15. Dystrophic changes: Note nails, hair or skin (shiny, thin, thick etc.) of the affected side. Please describe the nature of these changes. | | Nail: Y/N<br>Describe if Y:<br>Hair: Y/N<br>Describe if Y<br>Skin: Y/N<br>Describe if Y |
| 16. Motor abnormalities: Note weakness, myoclonus/tremor, or dystonia on the affected side. Weakness to be rated at most affected joint by the manual muscle testing, 0-5 (0 = no movement, 1 = flicker of movement, 2 = movement in absence of gravity, 3 = movement against gravity, 4 = weak, 5 = normal power). Note decreased active range of motion (AROM) of affected limb. | | Weakness: Y/N<br>If Y rate 0, 1, 2, 3, 4, 5<br>Myoclonus/Tremor: Y/N<br>Dystonia: Y/N<br>Decreased ROM: Y/N |

*For Budapest Criteria and CRPS Severity Score, at least a 0.5 degree C. difference will be considered temperature asymmetry. For inclusion criterion, a different threshold is used.

2. Appendix 3).
3. Prior use of neridronate or participation in a clinical study where the participant may have received neridronate.
4. The use of any of the following treatments within the timeframe specified from Randomization Visit:
   a. Within the last 12 months:
      IV bisphosphonates
      IV immunoglobulin
   b. Within the last 6 months:
      Any oral bisphosphonate, denosumab (Prolia®) or receptor activator of nuclear factor kappa B ligand (RANKL) inhibitors (e.g., denosumab biosimilar compounds)
      Calcitonin
      Ketamine
      Radiation therapy to the head or neck
   c. Within the last 3 months:
      Cinacalcet
      Use of blocks (e.g., nerve block, sympathetic nerve ablation or block, epidurals, local anesthetic blocks, spinal cord stimulation, peripheral nerve stimulation, dorsal root ganglion block, etc.)
      Monoclonal antibody peptides against CGRP (e.g., erenumab)
   d. Within the last 1 month:
      Any systemic corticosteroids (intranasal, inhaled, or topical corticosteroids are acceptable)
   e. Within the last 2 weeks:
      Lidocaine patch
5. Participants currently taking or planning to be treated with prohibited concomitant medications/therapies, or not likely able to follow the protocol restrictions for use of concomitant treatment.
6. Evidence of severely impaired renal function (estimated glomerular filtration rate [eGFR]<30 mL/min/1.73 $m^2$ using the 2021Chronic Kidney Disease Epidemiology Collaboration [CKD-EPI] creatinine equation, or a urinary albumin to creatinine ratio>150 mg/g), based on central laboratory data obtained prior to Randomization Visit.
7. Prior or planned renal transplant.
8. Hypocalcemia or high risk of hypocalcemia defined as serum calcium below the central laboratory's reference range at Screening and/or Randomization Visits; history of conditions leading to hypocalcemia or a metabolic disorder anticipated to increase risk for hypocalcemia (e.g., hypoparathyroidism); anticipated need for any new drug with known potential to cause hypocalcemia (e.g., aminoglycosides, new treatment with or dose adjustment of loop diuretics) during the trial. Participants on a stable dose of loop diuretics and/or aminoglycosides for ≥3 months may be included as long as no dosage increases are anticipated, and calcium levels are in the reference range.
9. Vitamin D deficiency, defined as a 25 (OH) D level<30 ng/ml based on central laboratory results obtained prior to Randomization. Participants with 25 (OH) D level<30 ng/mL may receive supplementation consistent with guidelines and/or local standards to ensure eligibility. Local laboratory results may be used to guide supplementation. A 25 (OH) D level of ≥30 ng/mL must be documented based on central laboratory results prior to allocation of IP. Participants who fail to meet this level will be screen failures.
10. Any of the following dental findings at Screening or Randomization Visits: (1) tooth extraction or other invasive dental procedure within 3 months prior to Randomization Visit (2) unhealed or infected tooth extraction site (3) significant dental/periodontal disease that may pre-dispose to need for tooth extraction or other invasive dental procedures (4) planned invasive dental procedure during the trial, (5) evidence of denture-related gum trauma or improperly fitting dentures causing injury.
11. Presence of ocular inflammation on examination including redness and sensitivity to light or based on symptomatic blurred vision or eye pain at Screening and/or Randomization Visit. An ophthalmologist may be consulted; documentation that no ocular inflammation is present would be required for enrollment.

12. History of malignancy in the past 5 years prior to Screening Visit except for basal cell or squamous cell skin carcinoma, Stage 0 cervical carcinoma in situ, and treated ductal carcinoma in situ of the breast.
13. Elevated aspartate aminotransferase, alanine aminotransferase, bilirubin (unless attributable to a known diagnosis of Gilbert's syndrome), or alkaline phosphatase (if hepatic) greater than 2-fold upper limit of normal, based on central laboratory data obtained at Screening, or evidence of current clinically significant liver disease.
14. History of regular alcohol consumption exceeding 14 standard drinks/week (for men) or 7 standard drinks/week (for women). One standard drink is equivalent to 14 g of ethanol or 5 US fluid ounces (fl oz) (150 mL) of wine (approximately 12% alcohol by volume), 12 fl oz (360 mL) of beer (approximately 5% alcohol by volume), or 1.5 fl oz (45 mL) of hard liquor (approximately 40% alcohol by volume) within 1 year prior to the Screening Visit
15. Any recreational or illegal substance use within 2 months prior to Screening or unwilling to refrain from such use for the duration of the trial that in the opinion of the Investigator may impact assessment of pain, other efficacy measures, reliability of eDiary completion, or safety of the participant.
16. Positive drug screen at the Screening or Randomization Visits for prohibited substances.
17. Serum potassium or magnesium outside of the central laboratory's reference range, based on central laboratory data.
18. Corrected QT interval (according to Fridericia's formula; QTcF) >450 msec for men/470 msec for women (average of 3 ECGs).
19. Clinically unstable cardiac disease, that in the opinion of the Investigator may impact the safety of the participant in this trial, which includes IV infusions, or may impact QTc prolongation (e.g., uncontrolled hypertension, clinically significant heart arrhythmia, symptomatic heart failure, stroke, myocardial event, coronary bypass, coronary revascularization procedure, or thromboembolic event) within the last 6 months of the Randomization Visit.
20. Any known conditions, from 3 months prior to Screening Visit or to the Randomization Visit, that may interfere with the assessment of CRPS, CRPS-related pain, safety, or other trial assessments (e.g., neuropathy, diabetic peripheral neuropathy, post-herpetic neuralgia, fibromyalgia, Lyme disease, rheumatoid arthritis, Raynaud phenomena, active gout in the affected limb, multiple sclerosis, severe depression etc.).
    Note: participants with conditions that may require additional time for diagnosis or that could temporarily impact trial evaluations (including APR evaluation) such as acute illness, infection, immunization, etc. within 7 days of Randomization Visit may be included by postponing treatment if this is within the allotted screening time frame.
21. History of an allergic or hypersensitivity reaction to any bisphosphonate, or to acetaminophen, vitamin D supplements, calcium supplements, or oxycodone.
22. Participation in another investigational drug study within 6 months of Randomization Visit, or planned participation in any other study prior to completing this trial.
23. Participant is engaged or plans to engage in litigation related to their CRPS in which monetary gain or loss, or other compensation is a factor as this may affect their objective participation in the trial.
24. Participant is directly or indirectly involved in the conduct and administration of this trial as an Investigator, sub-Investigator, trial coordinator, or other trial staff member, or the participant is a first-degree family member, significant other, or relative residing with one of the above persons involved directly or indirectly in the trial at this site.

Efficacy Assessments

Participant eDiary

Participants will be trained on all elements of the eDiary during the Screening Visit and a refresher will be provided at Randomization Visit. Continuous training may be provided throughout the trial. Collection of a twice-daily 11-point NRS of "pain now" (Appendix 4), 11-point NRS of worst pain over the past 12 hours (Appendix 4), rescue medication (type, dose, and time), and if assistance was required for completing the eDiary. Daily Sleep Interference Scale impact of pain on sleep (DSIS) on the 11-point NRS (Appendix 5) will be collected in the morning only.

Participants will be trained to fill out the eDiary at specific times, approximately 12 hours apart each day. If a participant requires rescue medication within 4 hours of the scheduled daily eDiary completion, they should either fill out the Diary prior to taking rescue or complete the eDiary 4 hours following the administration of rescue medication, whichever is closer in time to planned timing for completion.

Participants who fall below 10 of 14 entries for "pain now" in the 7 days leading up to Randomization Visit will be considered screen failures. During the treatment period, participants who miss 2 consecutive days of eDiary entry should be contacted and reminded of the importance of daily completion and provided guidance on means of improving compliance (e.g., using notification alarms).

Patient Global Impression Severity (PGI-S)

The PGI-S (Appendix 8) will be assessed at the trial site. The 6-point PGI-S is an overall assessment of the participant's perception of the severity of their CRPS condition at the time of the assessment. Participants will respond to the question "How would you rate the symptoms of your CPRS at this time." Possible responses are scored from 0 to 5 representing none, minimal, mild, moderate, severe, very severe.

Patient Global Impression of Change (PGI-C)

The PGI-C (Appendix 6) will be assessed at the trial site and is an overall assessment of the participant's perception of how their condition has changed. It is part of the COMPACT core outcome set for clinical trials in CRPS. Participants will be asked to select the statement that best describes the change (if any) in their CRPS-related health since just before they got the first IV dose as part of this study. Possible responses are scored from 1 to 7 representing very much improved, much improved, minimally improved, no change, minimally worse, much worse, very much worse.

Short-Form McGill Pain Questionnaire 2 (SF-MPQ-2)

The SF-MPQ-2 is a multidimensional pain scale that covers 22 descriptors of neuropathic and non-neuropathic aspects of pain intensity that are rated on an 11-point NRS (Appendix 9). The SF-MPQ-2 will provide a granular profile of pain outcomes beyond that of single-dimension pain intensity ratings. The SF-MPQ-2 assesses 4 core domains of pain: continuous pain, intermittent pain, neuropathic pain, and affective descriptors. Each item is scored on a 0-10 NRS, where 0=no pain and 10=worst possible pain, based on the participant's experience over the past week. Domain scores are calculated as the mean of item scores within each subscale, and a total score is derived by averaging all 22 items. The total and domain scores range from 0 to 10, with higher scores indicating greater pain severity. The instrument has demonstrated strong psychometric validity, including in populations with neuropathic and mixed-pain conditions such as CRPS. It is one of the core recommended outcome measures in international CRPS research (COMPACT). A 30% reduction from baseline in total score is commonly used in chronic pain trials to indicate clinically meaningful improvement.

Short Form Health Survey Acute Version 2.0 (SF-36 V2.0)

The SF-36 V2.0 (Appendix 10) is a widely used measure of general health status used in clinical trials across a broad range of disease areas. It yields 8 domain scores and a Physical Component Summary and Mental Component Summary. The eight domains include Physical Functioning, Role-Physical, Bodily Pain, General Health, Vitality, Social Functioning, Role-Emotional, and Mental Health. Each domain score is calculated by transforming raw responses to a 0-100 scale, where higher scores indicate better health status. The instrument has demonstrated strong psychometric validity, including in populations with chronic pain and demonstrated sensitivity to CRPS-related treatment differences in the NERIAS trial. Although the minimally clinically important difference varies by disease condition and domain, typically a change of 5-10 points (with norm-based scoring) is considered clinically meaningful. The recall period for the SF-36 for this trial is one week.

Complex Regional Pain Syndrome Severity Score (CSS)

The CSS was developed to be a continuous score that reflects the 16 features of CRPS (8 symptoms; 8 signs-Appendix 2) included in the Budapest Criteria. Each of the 8 symptoms in the diagnostic criteria as given by or elicited from the participant and documented by the Investigator, with a recall of 48 hours, as yes (scored 1) or no (scored 0). Participants will be assessed by the Investigator on physical examination for each of the 8 signs in the diagnostic criteria as either yes (scored 1) or no (scored 0). Theses scores of symptoms and signs are summed. The resulting score ranges from 0 to 16, with higher scores indicating greater CRPS severity. Instructions for assessing the 8 signs and 8 symptoms are identical to those used in assessing the Budapest clinical diagnostic criteria (Appendix 1).

Clinical Global Impression of Change (CGI-C)

The CGI-C (Appendix 7) will be assessed at the trial site. The 7-point CGI-C is an overall assessment of the Investigator's perception of how the participant's condition has changed (if any) since prior to dosing on the Randomization Visit. This assessment should consider pain severity, physical function of the affected limb, edema, skin changes, sensory abnormalities (e.g., allodynia), and other clinical features. This rating should reflect the investigator's overall clinical impression, integrating both patient-reported symptoms and the investigator's clinical assessment. Possible responses are scored from 1 to 7 representing very much improved, much improved, minimally improved, no change, minimally worse, much worse, very much worse.

Active Range of Motion (AROM) and Pain with Range of Motion (ROM)

AROM is the range of movement through which a participant can actively and without assistance (e.g., from a tool, surface, person or their other hand) move a joint using the adjacent muscles. Measuring the AROM does not involve any external stimulation; the participant is not touched and decides how far to move. Because this movement does not always isolate one joint, it can be a good measure of functional movement. To perform the procedure, the participant should be instructed that they will be asked to move in a specific manner as far as they can without causing severe pain; the Investigator will measure how far the participant moved but will not touch them while doing the measurement.

If the participant has CRPS in an upper limb, flexion in the unaffected elbow will be measured, followed by dorsiflexion and palmar flexion of the unaffected wrist. The participant will also be asked to make a tight first (no AROM measurement; for pain assessment only). Measures will be repeated on the affected side in the same order. Following measurements, the participant will immediately be asked to rate their pain with movement on a scale ranging from 0 (no pain) to 10 (worst possible pain).

If the participant has CRPS in a lower limb, flexion in the unaffected knee will be measured, followed by dorsiflexion and plantar flexion of the unaffected ankle. Measures will be repeated on the affected side in the same order. Following measurements, the participant will immediately be asked to rate their pain with movement on a scale ranging from 0 (no pain) to 10 (worst possible pain).

Appendix 11 provides instructions on how the movements should be performed and measured.

Known adverse reactions for neridronate are reported in Table 4 below.

TABLE 4

Known Adverse Drug Reactions for Neridronate April 2024 Summary of Product Characteristics—Reference Safety Information

| System Organ Class | Adverse Drug Reactions | Frequency* |
|---|---|---|
| Metabolism and nutrition disorders: | Hypocalcemia | Not known |
| | Hypophosphatemia | Not known |
| Musculoskeletal and connective tissue disorders | Atypical subtrochanteric and diaphyseal femoral fractures (adverse effects of bisphosphonates) | Rare |
| | Osteonecrosis of the jaw | Very rare |
| Eye disorders | Anterior uveitis | Not known |
| | Episcleritis | Not known |
| | Conjunctivitis | Not known |
| | Ocular pain | Not known |
| Ear and labyrinth disorders | Osteonecrosis of external auditory canal (adverse effects of bisphosphonates) | Very rare |
| | Vertigo | Very rare |
| Skin and subcutaneous tissue disorders | Rash, erythema | Very rare |
| General disorders and administration site conditions | Transient symptoms as per acute phase response (myalgia, malaise and rarely fever), typically associated with the start of treatment | Rare |
| | Pain at the injection site, which subsides after a few minutes | "Very rare" for the IV route of administration. Uncommon for intramuscular route of administration. |

IV = intravenous
*Frequency is defined as:
Uncommon (≥1/1000, <1/100)
Rare (≥1/10000, <1/1000)
Very rare (<1/10000)
Not known (cannot be defined from the available data).

Acetaminophen is included in the trial as prophylaxis of APR, to treat APR symptoms, as needed, and as rescue therapy for pain. High doses of acetaminophen may cause hepatotoxicity and can lead to liver failure. Participants who take acetaminophen for prevention or relief of symptoms of APR during the treatment periods will be reminded that the total dose must not exceed 4 g/day and that dose calculations should include acetaminophen present in many over-the-counter (OTC) drugs, particularly combination analgesics and cough and cold medications.

Oxycodone 5 mg (immediate release) is permitted as rescue medication if acetaminophen therapy does not suffice. The benefits and risks of opioids, including oxycodone, should be considered, including the more common risks of asthenia, constipation, dizziness, dry mouth, headache, nausea, pruritus, somnolence, sweating, and vomiting as well as less common but serious risks of addiction (even with short term use) and overdose (especially in combination with benzodiazepines, other opioids, alcohol or other CNS depressants). Oxycodone can also be associated with opioid-induced hyperalgesia with a paradoxical increase in pain and/or sensitivity to pain. Investigators should be familiar with the content of the approved prescribing information for oxycodone 5 mg prior to prescribing as a part of this trial. Participants prescribed oxycodone as a part of this trial should be counseled to never give anyone else their oxycodone and to store oxycodone securely, out of sight and reach of children, and in a location not accessible by others, including visitors to the home.

Recommended daily doses of calcium and vitamin D are lower than the tolerable upper intake level, at which there is no risk to healthy individuals. Higher doses may be needed to correct vitamin D or/and calcium deficiency. Short courses of high doses of vitamin D and/or calcium are anticipated to pose no significant risk to trial participants (Appendix 15 and 16).

Other supplementations (e.g., potassium, phosphate, magnesium, medications to treat specific adverse events (AEs) may be administered to address laboratory findings. The risks of each supplement will be explained to the participants by site personnel.

Appendix 1: Budapest Criteria

To make the clinical diagnosis of CRPS, the following criteria must be met:

| New IASP diagnostic criteria for complex regional pain syndrome ("Budapest criteria") (A-D must apply) | |
|---|---|
| E. The patient has continuing pain which is disproportionate to the inciting event | ☐ |
| F. The patient reports at least one symptom in 3 or more of the categories | ☐ |
| G. The patient displays at least one sign in 2 or more of the categories | ☐ |
| H. No other diagnosis can better explain the signs and symptoms | ☐ |

| Category | | Symptom (the patient reports a problem) | Sign (you can see or feel a problem on examination) |
|---|---|---|---|
| 1 "Sensory" | Allodynia (to light touch/brush stroke and/or temperature sensation and/or deep somatic pressure and/or joint movement), and/or hyperalgesia (to pinprick) | Reported hyperesthesia also qualifies as a symptom ☐ | ☐ |
| 2 "Vasomotor" | Temperature asymmetry and/or skin color changes and/or skin color asymmetry | ☐ | ☐ |
| 3 "Sudomotor/ oedema" | Oedema and/or sweating changes and/or sweating asymmetry | ☐ | ☐ |
| 4 "Motor/ trophic" | Decreased range of motion and/or motor dysfunction (weakness, tremor, dystonia) and/or trophic changes (hair/nail/skin) | ☐ | ☐ |

Additionally, to be diagnosed with CRPS-1, there must be no known peripheral nerve injury.

Appendix 2: Complex Regional Pain Syndrome Severity Score and Additional Complex Regional Pain Syndrome Characteristics Signs of CRPS will be assessed by the Investigator and symptoms by the participant using the same methodology for both the Budapest clinical diagnostic criteria and the CRPS severity score, although different calculations are used to derive the criteria and the scale. Please note that the following contains more details than are part of the criteria or scale; these details provide information on CRPS-related signs and symptoms for other elements of the trial.

The following assessments should be completed:

| Criteria | Yes/ No | Details of the finding on the affected side (unless otherwise specified), if criterion marked as "yes" |
|---|---|---|
| SYMPTOMS (as reported by or elicited from participants, in the past 48 hours) | | |
| 1. The pain is disproportionate to or continues longer than expected based on the clinician's experience as to what is usual and customary in this type of injury/lesion. | | NA |
| 2a. Allodynia: a usually innocuous stimuli is now perceived as painful. | | NA |
| 2b. Hyperalgesia: Increased pain from a stimulus that normally provokes pain. The stimulus leads to a "great increase in the expected response". The participant reports that normally painful stimuli (e.g., stubbing the toe, hot bath water etc.) is now intensely painful and/or hurts for a prolonged time. | | NA |
| 3. Temperature asymmetry that is obvious to the participant. | | Affected side:<br>Warmer: Y/N<br>Colder: Y/N |
| 4. Color asymmetry that is obvious to the participant. | | Red: Y/N<br>Blue: Y/N<br>Pale: Y/N<br>Mottled: Y/N |
| 5. Sweating asymmetry that is obvious to the participant. | | NA |
| 6. Edema that is obvious to the participant (may be described as swelling). | | NA |
| 7. Dystrophic changes of nails, hair, or skin as described by the participant. | | Nails: Y/N<br>Hair: Y/N<br>Skin: Y/N |
| 8. Motor abnormalities such as weakness, tremor, dystonia (limb locked in unusual position) or myoclonus as described by the participant. Decreased range of motion as described by the participant. | | Weakness: Y/N<br>Dystonia: Y/N<br>Myoclonus: Y/N<br>Decreased ROM: Y/N |
| SIGNS (as observed by examiner on the exam date) | | |
| 9. Hyperalgesia: as tested by a single pinprick on the affected side (in center of most affected region) and same site of the contralateral limb using a new safety pin. Hyperalgesia is defined as increased pain from a stimulus that normally provokes pain. The stimulus leads to a great increase in the expected response. | | N/A |
| 10. Allodynia: reflects normally innocuous stimuli now being interpreted as painful. If any one of the following is positive on the affected side, it is not essential to complete all 4 of the following assessments:<br>to light touch as tested by light manual touch (or brush);<br>to deep joint pressure assessed by "firm" manual pressure to joint;<br>to vibration as assessed by 128 Hz tuning fork over bony prominence in affected limb;<br>to temperature as assessed by the blade of a tuning fork cooled under cold water (or cool water in a test tube) and heated under warm water (or warm water in a test tube). | | N/A |
| 11. Temperature asymmetry:* in the affected area compared to the comparable area on the contralateral limb.<br>Temperature of the affected and unaffected limbs will be measured using a digital infrared thermometer. Measurements across slightly different areas of the affected region and contralateral side may be required in order to identify the region with largest difference. Record the temperature at the warmest or coldest spot on the affected side and in a similar location on the contralateral side. | N/A | Temperature R side:<br>Temperature L side: |
| 12. Skin Color asymmetry: note region affected (i.e. hand, foot, knee or larger region). Please specify the color of the affected side as being red, blue, or pale, as well as being mottled or having a scar. This should be coded even if color difference is solely related to edema or scar tissue. If scar tissue is present and affecting the color of the area (as in a burn), please note. | | Red: Y/N<br>Blue: Y/N<br>Pale: Y/N<br>Mottled: Y/N<br>Scar presented and affecting color: Y/N |

-continued

| Criteria | Yes/ No | Details of the finding on the affected side (unless otherwise specified), if criterion marked as "yes" |
|---|---|---|
| 13. Asymmetric edema: Rate edema on a scale of 0 (none); 1 (mild); 2 (moderate); 3 (severe) on the affected limb at the CRPS location where 0 (none) is defined as no visible edema; 1 (mild) is defined as visible edema but bony landmarks are clearly visible; 2 (moderate) is visible edema but bony landmarks are obscured and 3 (severe) defined as very severe edema without visible bony landmarks and/or with notable skin tightness. | | Affected limb edema: R/L 0, 1, 2, 3 |
| 14. Sweating asymmetry: If not obvious, this may be checked by running a smooth handled instrument (e.g., blade of turning fork) over the skin and noting if the instrument slides more easily on one side than the other, or by rate/degree of soaking (weight) of a facial tissue/sock etc., whatever is needed so that the categorical "yes/no" response may be marked. | | N/A |
| 15. Dystrophic changes: Note nails, hair or skin (shiny, thin, thick etc.) of the affected side. Please describe the nature of these changes. | | Nail: Y/N Describe if Y: Hair: Y/N Describe if Y Skin: Y/N Describe if Y |
| 16. Motor abnormalities: Note weakness, myoclonus/tremor, or dystonia on the affected side. Weakness to be rated at most affected joint by the manual muscle testing, 0-5 (0 = no movement, 1 = flicker of movement, 2 = movement in absence of gravity, 3 = movement against gravity, 4 = weak, 5 = normal power). Note decreased active range of motion (AROM) of affected limb. | | Weakness: Y/N If Y rate 0, 1, 2, 3, 4, 5 Myoclonus/Tremor: Y/N Dystonia: Y/N Decreased ROM: Y/N |

*For Budapest Criteria and CRPS Severity Score, at least a 0.5 degree C. difference will be considered temperature asymmetry. For inclusion criterion, a different threshold is used.

Appendix 3: Pain Catastrophizing Scale (PCS)

The PCS is a 13-item self-report measure designed to assess catastrophic thinking related to pain among adults with or without chronic pain.

Pain Catastrophizing Scale (Copyright 1995, 2001, 2004, 2006, 2009 Michael J L Sullivan, PhD) Everyone experiences painful situations at some point in their lives. Such experiences may include headaches, tooth pain, joint or muscle pain. People are often exposed to situations that may cause pain such as illness, injury, dental procedures or surgery.

We are interested in the types of thoughts and feeling that you have when you are in pain. Listed below are thirteen statements describing different thoughts and feelings that may be associated with pain. Using the scale, please indicate the degree to which you have these thoughts and feelings when you are experiencing pain.

| | Not at all | To a slight degree | To a moderate degree | To a great degree | All the time |
|---|---|---|---|---|---|
| I worry all the time about whether the pain will end | 0 | 1 | 2 | 3 | 4 |
| I feel I can't go on | 0 | 1 | 2 | 3 | 4 |
| It's temible and I think it's never going to get any better | 0 | 1 | 2 | 3 | 4 |
| It's awful and I feel that it overwhelms me | 0 | 1 | 2 | 3 | 4 |
| I feel I can't stand it anymore | 0 | 1 | 2 | 3 | 4 |
| I become afraid that the pain will get worse | 0 | 1 | 2 | 3 | 4 |

-continued

| | Not at all | To a slight degree | To a moderate degree | To a great degree | All the time |
|---|---|---|---|---|---|
| I keep thinking of other painful events | 0 | 1 | 2 | 3 | 4 |
| I anxiously want the pain to go away | 0 | 1 | 2 | 3 | 4 |
| I can't seem to keep it out of my mind | 0 | 1 | 2 | 3 | 4 |
| I keep thinking about how much it hurts | 0 | 1 | 2 | 3 | 4 |
| I keep thinking about how badly I want the pain to stop | 0 | 1 | 2 | 3 | 4 |
| There's nothing I can do to reduce the intensity of the pain | 0 | 1 | 2 | 3 | 4 |
| I wonder whether something serious may happen | 0 | 1 | 2 | 3 | 4 |

Appendix 4: Patient eDiary: 11-Point Numeric Rating Scale (NRS) Current and Worst Pain Administration: Twice daily eDiary.

Pain Now Assessment

The participants will be asked to record their current CRPS-related pain intensity using the following question:

Please rate your CRPS pain by selecting the one number that best describes your pain right now.

| 0 | 1 | 2 | 3 | 4 | 5 | 6 | 7 | 8 | 9 | 10 |
|---|---|---|---|---|---|---|---|---|---|---|
| No pain | | | | | | | | | | Worst possible pain |

Worst Pain Assessment

The participants will be asked to record their worst CRPS-related pain intensity using the following question:

Please rate your pain by selecting the one number that best describes your pain at its worst during the last 12 hours.

| 0 | 1 | 2 | 3 | 4 | 5 | 6 | 7 | 8 | 9 | 10 |
|---|---|---|---|---|---|---|---|---|---|---|
| No pain | | | | | | | | | | Worst possible pain |

Appendix 5: Patient eDiary: Daily Sleep Interference Scale (DSIS)

Administration: Once daily eDiary completed in the morning.

Sleep Interference Assessment

The participants will be asked to record CRPS-related pain interference on sleep using the following question:

Please rate by selecting the one number that best describes how much your CRPS pain has interfered with your sleep over the past 24 hours.

| 0 | 1 | 2 | 3 | 4 | 5 | 6 | 7 | 8 | 9 | 10 |
|---|---|---|---|---|---|---|---|---|---|---|
| Did not interfere with sleep | | | | | | | | | | Completely interfered with sleep-unable to sleep due to CRPS pain |

Appendix 6: Patient Global Impression of Change (PGIC)

Select the statement that best describes the change (if any) in your CRPS-related health since just before your first trial infusion

| Rating | Level of Improvement |
|---|---|
| 1 | Very much improved |
| 2 | Much improved |
| 3 | Minimally improved |
| 4 | No change |
| 5 | Minimally worse |
| 6 | Much worse |
| 7 | Very much worse |

Appendix 7: Clinician Global Impression of Change (CGI-C)

Select the statement that best describes the change (if any) in the participant's CRPS related health since just before the first trial infusion.

| Rating | Level of Improvement |
|---|---|
| 1 | Very much improved |
| 2 | Much improved |
| 3 | Minimally improved |
| 4 | No change |
| 5 | Minimally worse |
| 6 | Much worse |
| 7 | Very much worse |

Appendix 8: Patient Global Impression of Severity (PGIS)

Select the statement that best describes the severity of your CRPS symptoms at this time

| Rating | CRPS Symptoms |
|---|---|
| 0 | None |
| 1 | Minimal |
| 2 | Mild |
| 3 | Moderate |
| 4 | Severe |
| 5 | Very Severe |

Appendix 9: Short-Form McGill Pain Questionnaire-2 (SF-MPQ-2)

For this questionnaire, you will be presented with a list of words that describe some of the different qualities of pain and related symptoms. Please rate the intensity for each of the pain and related symptoms you felt during the past week on 0 to 10 scale, with 0 being no pain and 10 being the worst possible pain. Use 0 if the word does not describe your pain or related symptoms and limit yourself to a description of the pain related to your CRPS.

| Item Domain | Item Text | Response Format |
|---|---|---|
| Continuous Pain | Throbbing pain | 0 = No pain to 10 = Worst possible pain |
| Continuous Pain | Cramping pain | 0 = No pain to 10 = Worst possible pain |
| Continuous Pain | Gnawing pain | 0 = No pain to 10 = Worst possible pain |
| Continuous Pain | Aching pain | 0 = No pain to 10 = Worst possible pain |
| Continuous Pain | Heavy pain | 0 = No pain to 10 = Worst possible pain |
| Continuous Pain | Tender | 0 = No pain to 10 = Worst possible pain |
| Intermittent Pain | Shooting pain | 0 = No pain to 10 = Worst possible pain |
| Intermittent Pain | Stabbing pain | 0 = No pain to 10 = Worst possible pain |
| Intermittent Pain | Sharp pain | 0 = No pain to 10 = Worst possible pain |

| Item Domain | Item Text | Response Format |
|---|---|---|
| Intermittent Pain | Splitting pain | 0 = No pain to 10 = Worst possible pain |
| Intermittent Pain | Piercing pain | 0 = No pain to 10 = Worst possible pain |
| Intermittent Pain | Lancing pain | 0 = No pain to 10 = Worst possible pain |
| Neuropathic Pain | Electric-shock pain | 0 = No pain to 10 = Worst possible pain |
| Neuropathic Pain | Tingling or pins and needles | 0 = No pain to 10 = Worst possible pain |
| Neuropathic Pain | Pain caused by light touch | 0 = No pain to 10 = Worst possible pain |
| Neuropathic Pain | Cold-freezing pain | 0 = No pain to 10 = Worst possible pain |
| Neuropathic Pain | Pain caused by slight pressure | 0 = No pain to 10 = Worst possible pain |
| Neuropathic Pain | Hot-burning pain | 0 = No pain to 10 = Worst possible pain |
| Affective | Tiring-exhausting | 0 = No pain to 10 = Worst possible pain |
| Affective | Sickening | 0 = No pain to 10 = Worst possible pain |
| Affective | Fearful | 0 = No pain to 10 = Worst possible pain |
| Affective | Punishing-cruel | 0 = No pain to 10 = Worst possible pain |

Appendix 10: Short Form Health Survey Version 2.0 (SF-36 V2.0)

For this questionnaire you will be asked about how well you are able to do your usual activities, and how you rate your own health over the last week. Please be sure to complete all questions

| Item Domain | Item Text | Response Format |
|---|---|---|
| Physical Functioning | Vigorous activities, such as running, lifting heavy objects, participating in strenuous sports | Yes, limited a lot/ Yes, limited a little/ No, not limited at all |
| Physical Functioning | Moderate activities, such as moving a table, pushing a vacuum cleaner, bowling, or playing golf | Yes, limited a lot/ Yes, limited a little/ No, not limited at all |
| Physical Functioning | Lifting or carrying groceries | Yes, limited a lot/ Yes, limited a little/ No, not limited at all |
| Physical Functioning | Climbing several flights of stairs | Yes, limited a lot/ Yes, limited a little/ No, not limited at all |
| Physical Functioning | Climbing one flight of stairs | Yes, limited a lot/ Yes, limited a little/ No, not limited at all |
| Physical Functioning | Bending, kneeling, or stooping | Yes, limited a lot/ Yes, limited a little/ No, not limited at all |
| Physical Functioning | Walking more than a mile | Yes, limited a lot/ Yes, limited a little/ No, not limited at all |
| Physical Functioning | Walking several blocks | Yes, limited a lot/ Yes, limited a little/ No, not limited at all |
| Physical Functioning | Walking one block | Yes, limited a lot/ Yes, limited a little/ No, not limited at all |
| Physical Functioning | Bathing or dressing yourself | Yes, limited a lot/ Yes, limited a little/ No, not limited at all |
| Role Physical | Cut down the amount of time you spent on work or other activities | Yes/No |
| Role Physical | Accomplished less than you would like | Yes/No |
| Role Physical | Were limited in the kind of work or other activities | Yes/No |
| Role Physical | Had difficulty performing the work or other activities (e.g., took extra effort) | Yes/No |
| Bodily Pain | How much bodily pain have you had during the past week? | None/Very mild/Mild/ Moderate/Severe/Very severe |

-continued

| Item Domain | Item Text | Response Format |
|---|---|---|
| Bodily Pain | During the past week, how much did pain interfere with your normal work? | Not at all/A little bit/ Moderately/Quite a bit/ Extremely |
| General Health | In general, would you say your health is: | Excellent/Very good/ Good/Fair/Poor |
| General Health | I seem to get sick a little easier than other people | Definitely true/Mostly true/ Don't know/Mostly false/ Definitely false |
| General Health | I am as healthy as anybody I know | Definitely true/Mostly true/ Don't know/Mostly false/ Definitely false |
| General Health | I expect my health to get worse | Definitely true/Mostly true/ Don't know/Mostly false/ Definitely false |
| General Health | My health is excellent | Definitely true/Mostly true/ Don't know/Mostly false/ Definitely false |
| Vitality | Did you feel full of life? | All of the time/Most of the time/A good bit of the time/ Some of the time/A little of the time/None of the time |
| Vitality | Did you have a lot of energy? | All of the time/Most of the time/A good bit of the time/ Some of the time/A little of the time/None of the time |
| Vitality | Did you feel worn out? | All of the time/Most of the time/A good bit of the time Some of the time/A little of the time/None of the time |
| Vitality | Did you feel tired? | All of the time/Most of the time/A good bit of the time/ Some of the time/A little of the time/None of the time |
| Social Functioning | To what extent has your physical health or emotional problems interfered with your normal social activities with family, friends, neighbors, or groups? | Extremely Not at all/Slightly/ Moderately/Quite a bit/ |
| Social Functioning | During the past week, how much of the time has your physical health or emotional problems interfered with your social activities? | All of the time/Most of the time/Some of the time/A little of the time/None of the time |
| Role Emotional | Cut down the amount of time you spent on work or other activities | Yes/No |
| Role Emotional | Accomplished less than you would like | Yes/No |
| Role Emotional | Did work or other activities less carefully than usual | Yes/No |

-continued

| Item Domain | Item Text | Response Format |
|---|---|---|
| Mental Health | Have you been a very nervous person? | All of the time/Most of the time/A good bit of the time/Some of the time/A little of the time/None of the time |
| Mental Health | Have you felt so down in the dumps that nothing could cheer you up? | All of the time/Most of the time/A good bit of the time/Some of the time/A little of the time/None of the time |
| Mental Health | Have you felt calm and peaceful? | All of the time/Most of the time/A good bit of the time/Some of the time/A little of the time/None of the time |
| Mental Health | Did you feel downhearted and blue? | All of the time/Most of the time/A good bit of the time/Some of the time/A little of the time/None of the time |
| Mental Health | Have you been a happy person? | All of the time/Most of the time/A good bit of the time/Some of the time/A little of the time/None of the time |

Appendix 11: Assessing Active Range of Motion and Pain with Range of Motion

Active range of motion and pain with AROM will be measured in 2 joints of the affected limb and the same 2 joints on the contralateral limb (i.e., wrist and elbow; knee and ankle) using a goniometer. It is important to assure that the same Investigator assesses AROM at each visit to minimize between-rater variability, to the extent possible.

Inform the participant that to measure how well their limbs bend, they will be bending slowly as fully as they can, but the movement should not cause intolerable pain. The participant will also be asked to rate their pain with movement on a scale of 0-10, where 0 is no pain and 10 is the worst possible pain. Inform the participant that the Investigator will be close to the limb to take measurements but will not touch the limb so that the participant can rate their pain with movement, not pain caused by being touched. To case into the exercise, each measurement will start with the side that doesn't have CRPS and the joint closest to the trunk before moving to more distal joints and to the side that does have CRPS.

Participants with CRPS of the Lower Limb:

1) Knee:

Start by measuring the knee of the leg that is not affected with CRPS, then proceed to the knee of the leg that is affected by CRPS. Next move to the ankle of the leg that is not affected by CRPS and finally to the ankle of the leg that is affected by CRPS.

The participant should be in a supine position on the examination table, with a small pillow or similar elevating the head and neck.

The participant should be instructed to keep the leg/thigh that is not being assessed fully on the examination table. The leg that is being assessed should be straightened as fully as possible, with no rotation, ie, the great toe should be pointing toward the ceiling.

The Investigator should line up the goniometer so that the central hinge element is at the lateral knee joint line of the leg being assessed, about halfway between the kneecap and popliteal fossa. Line up one arm of the goniometer so that it is pointing towards greater trochanter and the other end pointing towards the lateral malleolus. If the leg straightens fully, the goniometer should read 0°.

The participant should be instructed to move their foot slowly towards their buttocks, keeping their knee pointed straight towards the ceiling. Instruct the participant to bend the knee as fully as possible without causing intolerable pain.

See FIG. 1.

When the knee is fully flexed, align the goniometer as per prior, measure the flexion angle, and record the measurement.

Repeat 3 times and record each measurement in the participant's source documentation and/or eCRF. (An average calculation will be derived.)

Repeat this procedure on the side that is affected with CRPS.

Immediately after completing the 3 knee flexions on the CRPS affected side, ask the participant to rate their leg pain with movement on a scale of 0 (no pain) to 10 (most severe pain you can imagine), and record their assessment.

After both knees are assessed, proceed to the ankle.

2) Ankle:

Start by measuring the ankle of the leg that is not affected with CRPS, then proceed to the knee of the ankle that is affected by CRPS.

Participant should be in a sitting position with legs handing freely off of the exam table. The feet/heel should not be touching a surface (ie, not resting on the floor or with the heel resting again the examination table).

The participant should be instructed to keep both thighs on the exam table and keep both knees and great toes pointing straightforward. Knees should be flexed about 90°.

The participant should be instructed to slow move their great toe towards the ceiling while leaving their knee bent and heel pointing straight towards the floor (ie, upper leg is parallel to the floor and lower leg is perpendicular to the floor). Instruct the participant to bend the ankle as fully as possible without causing intolerable pain.

Figure 2:
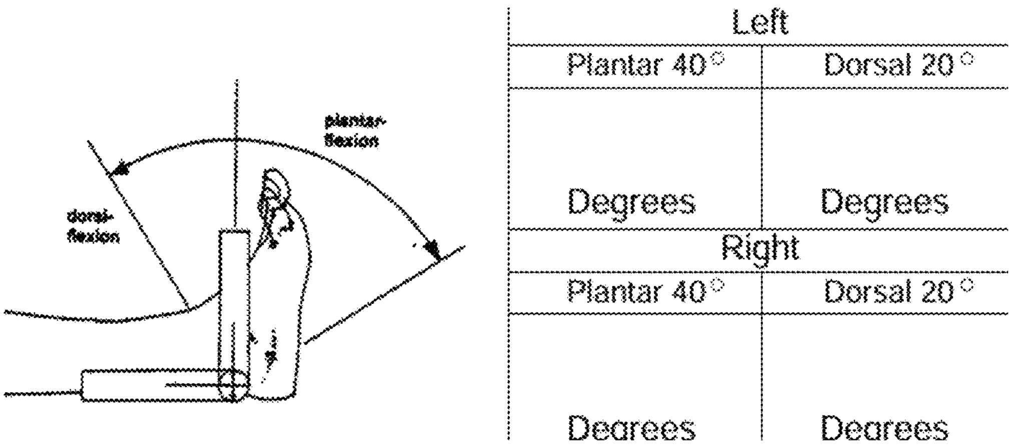
FIG. 2 is a graphical representation of ankle flexion-extension pertaining to Appendix 11 of Example 1.

See FIG. 2.

When the ankle is fully flexed, align the goniometer so that the central hinge element is at the lateral malleolus of the leg being assessed. Line up one arm of the goniometer pointing towards the knee about midpoint between the kneecap and popliteal fossa and the other arm of the goniometer pointing towards the great toe and record the measurement of ankle dorsiflexion.

Next have the participant slowly point their toes towards the floor as fully as possible without causing intolerable pain. Measure plantar flexion using the goniometer as previously described.

Repeat 3 times and record each measure in the participant's source documentation and/or eCRF as plantar flexion. (An average calculation will be derived.)

Repeat this procedure on the side that is affected with CRPS.

Immediately after completing the 3 replicate ankle dorsiflexion/plantar flexions on the CRPS affected side, ask the participant to rate their ankle pain with movement on a scale of 0 (no pain) to 10 (Worst possible pain).

Only for Participants with CRPS of the Upper Limb:

1) Elbow:

Start by measuring the elbow of the arm that is not affected with CRPS, then proceed to the elbow of the arm that is affected by CRPS. Next move to the wrist of the arm that is not affected by CRPS and finally to the wrist of the arm that is affected by CRPS.

Participant should be standing, but if not feasible, can be in a sitting position that allows the arms to straighten fully by their sides unimpeded. Start by measuring the arm that is not affected with CRPS.

The arm being assessed should be as fully straight as possible, with the palm facing forward and the pinkie finger lateral to the thigh.

Line up the goniometer so that the central hinge element is at the lateral epicondyle of the elbow of the arm being assessed. Line up one goniometer arm pointing towards the acromion process (lateral shoulder protuberance) and the other end pointing towards the radial styloid at the base of the thumb. If the participants arm straightens fully, the goniometer should read 0°.

The participant should be instructed to move their hand towards their shoulder, keeping their proximal arm at their side and their elbow pointing straight towards the floor.

Instruct the participant to slowly bend the elbow as fully as possible without causing intolerable pain. When the elbow is fully flexed, align the goniometer as per prior and measure the flexion angle.

Figure 3:
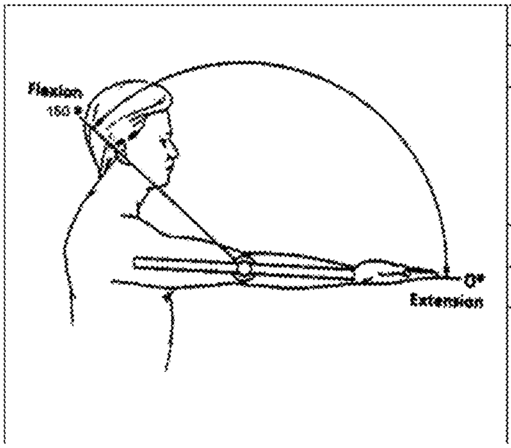
FIG. 3 is a graphical representation of elbow flexion pertaining to Appendix 11 of Example 1.

See FIG. 3.

Repeat 3 times and record each measure in the participant's source documentation and/or eCRF as elbow flexion. (An average calculation will be derived.)

Repeat this procedure on the side that is affected with CRPS.

Immediately after completing the 3 elbow flexions on the CRPS affected side, ask the participant to rate their arm pain with movement on a scale of 0 (no pain) to 10 (most severe pain you can imagine) and record their response in the participant's source documentation and/or eCRF.

After both elbows are assessed, proceed to the wrist.

2) Wrist:

Start by measuring the wrist that is not affected with CRPS.

Start by measuring the wrist of the leg that is not affected with CRPS, then proceed to the wrist of the leg that is affected by CRPS.

The participant should be in a seated position with their palm resting on their thigh. The arm being assessed should be bent around 90° at the elbow with the elbow resting on or just lateral to the thigh.

Line up the goniometer so that the central element is just distal to the at ulnar styloid process (bony protuberance at the wrist on the medial/pinkie side) of the wrist being assessed. Line up one arm pointing towards the lateral epicondyle and the other end pointing towards the base (i.e., metacarpal phalangeal joint—MCP) of the pinkie finger. If the wrist straightens fully, the goniometer should read 0°.

The participant should be instructed to keep their elbow at their side and flex their elbow about 20° so their hand, palm side down, is about 6-10" off of their thigh.

Instruct the participant to bend the wrist back so their fingers are pointing towards the ceiling without appreciably moving their forearm. They should move as fully as possible without causing tolerable pain.

Figure 4:
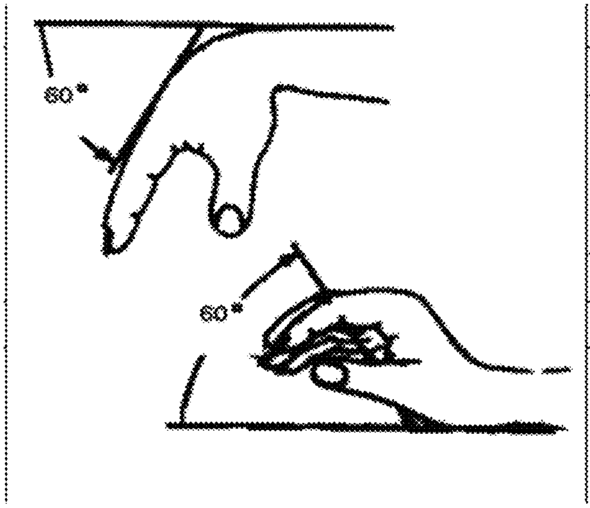
FIG. 4 is a graphical representation of wrist flexion pertaining to Appendix 11 of Example 1.

See FIG. 4.

When the wrist is fully dorsiflexed, align the goniometer as per prior and measure the flexion angle.

Repeat 3 times and record each measure in the participant's source documentation and/or eCRF as dorisflexion. (An average calculation will be derived.)

Next, have the participant slowly lower their hand so their fingers are pointing towards the floor as fully as possible without causing intolerable pain, while not appreciably moving their forearm. Measure palmar flexion using the goniometer as previously described.

Repeat 3 times and record each measure in the participant's source documentation and/or eCRF as palmar flexion. (An average calculation will be derived.)

Repeat this procedure on the side that is affected with CRPS.

Immediately after completing the 3 replicate wrist dorsiflexion/palmar flexions on the CRPS affected side, ask the participant to rate their wrist pain with movement on a scale of 0 (no pain) to 10 (most severe pain you can imagine) in the participant's source documentation and/or eCRF.

Next, ask the participant to make a tight first of their unaffected hand 3 times, followed by a tight first of their affected hand 3 times, and record any pain with movement on a scale of 0 (no pain) to 10 (worst possible pain) in the participant's source documentation and/or eCRF.

Appendix 14: Laboratory Tests

| Laboratory Tests | |
|---|---|
| Hematology | hematocrit (HCT) |
| | hemoglobin (HB) |
| | mean corpuscular hemoglobin (MCH) |
| | mean corpuscular hemoglobin concentration (MCHC) |
| | Mean cell volume (MCV) |
| | platelet count (PLT) |
| | red blood cell (RBC) |
| | RBC indices |
| | white blood cell (WBC) count with differential |
| | high sensitivity C-reactive protein (hsCRP)—prior to each IV infusion, Week 3, 6, and 12 |
| Serum Chemistry | alanine aminotransferase (ALT) |
| | albumin (ALB) |
| | alkaline phosphate (ALP); fractionate if ≥2 × ULN |
| | aspartate aminotransferase (AST) |
| | bicarbonate (HCO3) |
| | total bilirubin (Bil)/Reflex Direct Bilirubin if total bilirubin is > 1.5 × ULN |
| | blood urea nitrogen (BUN) |
| | calcium (Ca) |
| | chloride (Cl) |
| | creatine phosphokinase (CPK) |
| | creatinine serum (Cr) |
| | estimated glomerular filtration rate (eGFR) |
| | gamma-glutamyl transferase (GGT) |
| | glucose (Glc) |
| | lactic acid dehydrogenase (LDH) |
| | lipase (LPS) |
| | magnesium (Mg) |
| | parathyroid hormone (PTH)—Screening only |
| | phosphorus (P) |
| | potassium (K) |
| | total protein (Prot) |
| | sodium (Na) |
| | uric acid (urate) |
| | 25-hydroxy vitamin D (25(OH)D) |
| Urinalysis (dipstick) | bilirubin (Bilur) |
| | blood (Hematuria) |
| | glucose (UG) |
| | ketones (UR-KET) |
| | leukocyte esterase (LE) |
| | nitrite (NT) |
| | potential of hydrogen (pH) |
| | protein (PROT) |
| | specific gravity (SG) |
| | total protein (TPU) |
| | urobilinogen (UBG) |
| Urinalysis quantitative analysis—Screening only | albumin (microalbumin) |
| | Creatinine (CR) |
| | calculated urinary albumin and creatinine (ACR) |
| WOCBP | Serum Beta-human chorionic gonadotropin (β-HCG)—Screening only |
| | Urine dipstick—All other visits |

-continued

| Laboratory Tests | |
|---|---|
| Women of non-childbearing potential | FSH—Screening only |
| Drug (dipstick) | Marijuana (THC)<br>Amphetamines (AMP)<br>Cocaine (COC)<br>Methadone (MTD)<br>Benzodiazepines (BZO)<br>Phencyclidine (PCP)<br>Buprenorphine (BUP)<br>Fentanyl (FYL)<br>Oxycodone (OXY)<br>Propoxyphene (PPX)<br>Tramadol (TRA)<br>Secobarbital (BAR)<br>2-etheylidene-1,5-dimethyl-3,3-diphenylpyrrolidine (EDDP)<br>Methamphetamine (MET)<br>Methylenedioxymethamphetamine (MDMA)<br>Morphine (MOP/OPI)<br>Nortriptyline (TCA)<br>6-monacetylmorophine (6-MAM) |
| Pre-infusion Day 1, 4, 7, and 10 Results must be reviewed prior to each infusion | Serum calcium<br>Serum creatinine for estimated glomerular filtration rate (eGFR) |
| PK | PK—within 30 minutes prior to each infusion and within 30 minutes following each infusion on Day 1, 4, 7, and 10 |

Appendix 15. Vitamin D Supplementation and Replenishment of Vitamin D Levels

All participants will take supplemental vitamin D3 (1000 IU/day; e.g., cholecalciferol) starting from the Screening Visit and continuing throughout to the EOT, or different dosage if already on supplementation of similar dosage when entering the trial. During the course of the study/post infusions, if vitamin D levels are high, supplementation may be decreased or stopped.

General guidance is provided below for replenishment vitamin D3. However, replacement is decided based on clinical judgment and guided by repeated local laboratory values.

1. For participants with a baseline mean value below 10 ng/ml, a loading dose of 300,000 IU divided into daily doses over 4 weeks, followed by 1600-2000 IU per day for the overall duration of the trial period is suggested.
2. For participants with a baseline mean value between 10 ng/ml and 20 ng/ml, a loading dose of 150,000 IU divided into daily doses over 2 weeks, followed by 1600 IU per day for the overall duration of the trial period is suggested.
3. For participants with a baseline mean value between 20 ng/ml and 30 ng/ml, a loading dose of 100,000 IU divided into daily doses over 2 weeks, followed by 1000 IU per day for the overall duration of the trial period is suggested.
4. For participants with a baseline mean value above the limit of 30 ng/ml, a daily dose of 1,000 IU per day is suggested.

Note that rechecking vitamin D levels can occur approximately weekly during the screening period. For many people, some improvements will be seen in a week but full replenishment may take a month or more.

Appendix 16. Calcium Supplementation and Treatment of Hypocalcemia

All participants will take supplemental calcium citrate (500-1000 mg/day) or calcium carbonate (500-100 mg/day with food to improve absorption) starting from the Screening Visit and continuing throughout to the EOT, or different dosage if already on supplementation of similar dosage when entering the trial. Please note that participants with low stomach acid (i.e., on a proton pump inhibitor) should use calcium citrate, and, due to its better bioavailability, this is the preferred calcium supplement in this study. During the study post-infusions, if calcium levels are high, supplementation may be decreased or stopped. Hypocalcemia (below lower level of normal as per the central laboratory) will lead to IP being temporarily or permanently discontinued.

General guidance is provided below for replenishment of calcium. However, replacement is decided based on clinical judgment and guided by repeated local laboratory values.

1. Mild hypocalcemia: serum calcium<LLN for the central lab and >7.6 mg/dl and asymptomatic:
   - Supplement with calcium citrate 2000 mg/day. Calcium carbonate may be used if calcium citrate is not well tolerated (see above).
   - Assure participant is compliant with Vitamin D supplement (0).
   - If temporarily suspending IP infusion for hypocalcemia, re-check in 1-3 days; sometimes improvement in serum calcium may take several weeks.
   - IV calcium gluconate may be given (1-2 g IV over 2 hours), however, the risks of IV calcium administration while uncommon, should be considered (local thrombophlebitis, cardiotoxicity, hypotension, calcium taste, flushing, nausea, vomiting, sweating). Note that participants with cardiac arrhythmia or on digoxin therapy need continuous ECG monitoring during IV calcium replacement.
2. Severe hypocalcemia: serum calcium≤7.6 mg/dl and/or symptomatic at any level below reference range:
   - Symptoms may include: peri-oral and digital paresthesia; positive Trousseau's and Chvostek's signs; tetany and carpopedal spasm; laryngospasm; ECG changes (prolonged QT interval) and arrhythmia; seizures, etc.
   - Severe hypocalcemia is a medical emergency
   - Hospitalize the participant
   - Administer IV calcium gluconate
     - Initially, give 10-20 mL 10% calcium gluconate in 50-100 mL of 5% dextrose IV over 10 min with ECG monitoring.
       - This can be repeated until the participant is asymptomatic.
         - It should be followed up with a calcium gluconate infusion as follows: Dilute 100 mL of 10% calcium gluconate (10 vials) in 1 L of Normal saline or 5% dextrose and infuse at 50-100 mL/h.
         - Calcium chloride can be used as an alternative to calcium gluconate, but it is more irritant to veins and should only be given via a central line
         - Titrate the rate of infusion to achieve normocalcaemia
         - Oral calcium citrate supplements should be given concurrently
   - Risks of IV calcium administration are uncommon, but include local thrombophlebitis, cardiotoxicity, hypotension, calcium taste, flushing, nausea, vomiting and sweating. participants with cardiac arrhythmia or on digoxin therapy need continuous ECG monitoring during IV calcium replacement.

The investigator will record the SAE in the participant record and eCRF.

If hypocalcemia does not readily correct OR if it occurs >1 week following last IP infusion, evaluation for a cause should be undertaken and appropriate corrections of the underlying cause should be undertaken.

While the disclosure has been described above with reference to specific embodiments thereof, it is apparent that many changes, modification, and variations can be made without departing from the concept disclosed herein. Accordingly, it is intended to embrace all such changes, modifications, and variations that fall within the spirit and broad scope of the appended claims.

We claim:

1. A method of selectively treating CRPS Type 1 comprising:

(A) identifying a patient that has been diagnosed as having CRPS Type 1 as a patient that is likely to have reduction in pain intensity of 50% or more in response to aminobisphosphonate treatment and selecting that patient to receive treatment by confirming that the patient has:

(i) edema in the affected limb and at least two of the following:

1) redness in the affected limb relative to the contralateral limb,

2) ≥1° C. increase in temperature on the affected limb relative to the contralateral limb, and 3) moderate to severe edema, and (ii) increased uptake of a radiolabeled agent in the affected limb relative to the contralateral limb in a triple phase bone scan (TPBS);

wherein the patient is experiencing a pain intensity greater than 4 on the 11-point numeric rating scale (NRS); and (B) administering to the selected patient a 400 mg total dose of neridronate, wherein the selected patient achieves a reduction in pain intensity of 50% or more.

2. The method of claim 1, wherein the patient has 1) redness in the affected limb relative to the contralateral limb, 2) ≥1° C. increase in temperature on the affected limb relative to the contralateral limb, and 3) moderate to severe edema.

* * * * *